US011672869B2

(12) United States Patent
Lu et al.

(10) Patent No.: US 11,672,869 B2
(45) Date of Patent: Jun. 13, 2023

(54) FUNCTIONALIZATION OF BACTERIAL EFFECTOR TRANSLOCASE PROTEIN BY CHEMICAL CONJUGATION

(71) Applicant: Massachusetts Institute of Technology, Cambridge, MA (US)

(72) Inventors: Zeyu Lu, Cambridge, MA (US); Bradley L. Pentelute, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 16/550,036

(22) Filed: Aug. 23, 2019

(65) Prior Publication Data

US 2020/0061201 A1 Feb. 27, 2020

Related U.S. Application Data

(60) Provisional application No. 62/721,772, filed on Aug. 23, 2018.

(51) Int. Cl.
| | |
|---|---|
| *A61K 47/64* | (2017.01) |
| *C07K 16/18* | (2006.01) |
| *A61K 47/68* | (2017.01) |
| *C07K 14/195* | (2006.01) |
| *C12N 9/54* | (2006.01) |
| *A61K 47/66* | (2017.01) |

(52) U.S. Cl.
CPC .......... *A61K 47/6415* (2017.08); *A61K 47/66* (2017.08); *A61K 47/6815* (2017.08); *A61K 47/6829* (2017.08); *A61K 47/6843* (2017.08); *A61K 47/6851* (2017.08); *C07K 14/195* (2013.01); *C07K 16/18* (2013.01); *C12N 9/54* (2013.01); *C12Y 304/2207* (2013.01)

(58) Field of Classification Search

CPC .................. A61K 39/00; A61K 39/395; A61K 39/39558

USPC .......... 424/130.1, 134.1, 138.1, 178.1, 179.1
See application file for complete search history.

(56) References Cited

U.S. PATENT DOCUMENTS 9,708,374 B2 * 7/2017 Mechaly ................ C07K 14/32

OTHER PUBLICATIONS

VanVught et al (Computational and Structural Biotechnology Journal, 9(14):2014).*
Agarwal et al (Bioconjugate chemistry, 26:1746-192, 2015).*
Akbari et al., Immunotoxins in cancer therapy: Review and update. Int Rev Immunol. Jul. 4, 2017;36(4):207-219. doi: 10.1080/08830185.2017.1284211. Epub Mar. 1, 2017.
Akishiba et al., Cytosolic antibody delivery by lipid-sensitive endosomolytic peptide. Nat Chem. Aug. 2017;9(8):751-761. doi: 10.1038/nchem.2779. Epub May 22, 2017.
Carter et al., Next generation antibody drugs: Pursuit of the 'high-hanging fruit'. Nat Rev Drug Discov. Mar. 2018;17(3):197-223. doi: 10.1038/nrd.2017.227. Epub Dec. 1, 2017.
Guidotti et al., Cell-Penetrating Peptides: From Basic Research to Clinics. Trends Pharmacol Sci. Apr. 2017;38(4):406-424. doi: 10.1016/j.tips.2017.01.003. Epub Feb. 14, 2017.
Kaplon et al., Antibodies to watch in 2018. MAbs. Feb./Mar. 2018;10(2):183-203. doi: 10.1080/19420862.2018.1415671. Epub Jan. 16, 2018.
Lagasse et al., Recent advances in (therapeutic protein) drug development. F1000Res. Feb. 7, 2017;6:113, 17 pages. doi: 10.12688/f1000research.9970.1. eCollection 2017.
Leader et al., Protein therapeutics: A summary and pharmacological classification. Nat Rev Drug Discov. Jan. 2008;7(1):21-39.
Mout et al., General Strategy for Direct Cytosolic Protein Delivery via Protein-Nanoparticle Co-engineering. ACS Nano. Jun. 27, 2017;11(6):6416-21. doi: 10.1021/acsnano.7b02884. Epub Jun. 15, 2017.
Ng et al., Constructing hybrid protein zymogens through protective dendritic assembly. Angew Chemie—Int Ed. Jan. 3, 2014;53(1):324-8.
Scaletti et al., Protein delivery into cells using inorganic nanoparticle-protein supramolecular assemblies. Chem Soc Rev. May 21, 2018;47(10):3421-32. doi: 10.1039/c8cs00008e.
Scott et al., Antibody therapy of cancer. Nat Rev Cancer. Mar. 22, 2012;12(4):278-87. doi: 10.1038/nrc3236.
Sliwkowski et al., Antibody therapeutics in cancer. Science. Sep. 13, 2013;341(6151):1192-8. doi: 10.1126/science.1241145.
Weiner et al., Building better monoclonal antibody-based therapeutics. Nat Rev Immunol. May 2010;10(5):317-27. doi: 10.1038/nri2744.
Weiner et al., Monoclonal antibodies: versatile platforms for cancer immunotherapy. Nat Rev Immunol. May 2010;10(5):317-27. doi: 10.1038/nri2744.
Zhang et al., The fluorination effect of fluoroamphiphiles in cytosolic protein delivery. Nat Commun. Apr. 10, 2018;9:1377, 8 pages.
Zuris et al., Cationic lipid-mediated delivery of proteins enables efficient protein-based genome editing in vitro and in vivo. Nat Biotechnol. Jan. 2015;33(1):73-80. doi: 10.1038/nbt.3081. Epub Oct. 30, 2014.
Abi-Habib et al., A urokinase-activated recombinant anthrax toxin is selectively cytotoxic to many human tumor cell types. Mol Cancer Ther. 2006;5(10):2556-2562.
Alewine et al., Advances in anticancer immunotoxin therapy. Oncologist. 2015;20(2):176-185.
Alley et al., Contribution of linker stability to the activities of anticancer immunoconjugates. Bioconjug Chem. 2008;19(3):759-765.

(Continued)

*Primary Examiner* — Patricia Duffy
(74) *Attorney, Agent, or Firm* — Wolf, Greenfield & Sacks, P.C.

(57) ABSTRACT

The present invention relates to compositions and methods associated with antibody-bacterial effector translocase protein conjugates. Some aspects of the present invention relate to preventing or treating diseases using the antibody-protective antigen conjugates. Further aspects of the present invention relate to methods of chemically conjugating and synthesizing the antibody-bacterial effector translocase protein conjugates.

9 Claims, 20 Drawing Sheets

Specification includes a Sequence Listing.

(56) References Cited

OTHER PUBLICATIONS

Antic et al., Site-specific processing of Ras and Rap1 Switch I by a MARTX toxin effector domain. Nat Commun. 2015;6:7396.
Arora et al., Fusions of anthrax toxin lethal factor to the ADP-ribosylation domain of Pseudomonas exotoxin A are potent cytotoxins which are translocated to the cytosol of mammalian cells. J Biol Chem. 1992;267(22):15542-15548.
Arteaga et al., Treatment of HER2-positive breast cancer: current status and future perspectives. Nat Rev Clin Oncol. 2011;9(1):16-32.
Beck et al., Strategies and challenges for the next generation of antibody-drug conjugates. Nat Rev Drug Discov. 2017;16(5):315-337.
Berchuck et al., Overexpression of HER-2/neu is associated with poor survival in advanced epithelial ovarian cancer. Cancer Res. 1990;50(13):4087-4091.
Brand et al., Molecular mechanisms of resistance to the EGFR monoclonal antibody cetuximab. Cancer Biol Ther. 2011;11(9):777-792.
Chalouni et al., Fate of Antibody-Drug Conjugates in Cancer Cells. J Exp Clin Cancer Res. 2018;37(1):20.
Chen et al., A general strategy for the evolution of bond-forming enzymes using yeast display. Proc Natl Acad Sci USA. 2011; 108(28):11399-11404.
Ciarddiello et al., EGFR antagonists in cancer treatment [published correction appears in N Engl J Med. Apr. 9, 2009;360(15):1579]. N Engl J Med. 2008;358(11):1160-1174.
Corkery et al., Epidermal growth factor receptor as a potential therapeutic target in triple-negative breast cancer. Ann Oncol. 2009;20(5):862-867.
Feld et al., Structural basis for the unfolding of anthrax lethal factor by protective antigen oligomers. Nat Struct Mol Biol. 2010;17(11):1383-1390.
Graham et al., Cetuximab. Nat Rev Drug Discov. 2004;3(7):549-550.
Gravalos et al., HER2 in gastric cancer: a new prognostic factor and a novel therapeutic target. Ann Oncol. 2008;19(9):1523-1529.
Hu et al., Anthrax toxin uptake by primary immune cells as determined with a lethal factor-beta-lactamase fusion protein. PLoS One. 2009;4(11):e7946.
Huang et al., Urokinase plasminogen activator/urokinase-specific surface receptor expression and matrix invasion by breast cancer cells requires constitutive p38alpha mitogen-activated protein kinase activity. J Biol Chem. 2000;275(16):12266-12272.
Kalim et al., Intracellular trafficking of new anticancer therapeutics: antibody-drug conjugates. Drug Des Devel Ther. 2017;11:2265-2276.
Kintzer et al. The protective antigen component of anthrax toxin forms functional octameric complexes. J Mol Biol. 2009;392(3):614-629.
Kishimoto et al., Improving the efficacy and safety of biologic drugs with tolerogenic nanoparticles. Nat Nanotechnol. 2016;11(10):890-899.
Klimpel et al., Anthrax toxin protective antigen is activated by a cell surface protease with the sequence specificity and catalytic properties of furin. Proc Natl Acad Sci U S A. 1992;89(21):10277-10281.
Lacy et al., Structure of heptameric protective antigen bound to an anthrax toxin receptor: a role for receptor in pH-dependent pore formation. Proc Natl Acad Sci U S A. 2004;101(36):13147-13151.
Leppla, Anthrax toxin edema factor: a bacterial adenylate cyclase that increases cyclic AMP concentrations of eukaryotic cells. Proc Natl Acad Sci U S A. 1982;79(10):3162-3166.
Liao et al., Delivery of antibody mimics into mammalian cells via anthrax toxin protective antigen. Chembiochem. 2014;15(16):2458-2466.
Liu et al., Anti-tumor activity of anthrax toxin variants that form a functional translocation pore by intermolecular complementation. Oncotarget. 2017;8(39):65123-65131.
Liu et al., Solid tumor therapy by selectively targeting stromal endothelial cells. Proc Natl Acad Sci U S A. 2016;113(28):E4079-E4087.
Liu et al., Targeting of tumor cells by cell surface urokinase plasminogen activator-dependent anthrax toxin. J Biol Chem. 2001;276(21):17976-17984.
Liu et al., Tumor cell-selective cytotoxicity of matrix metalloproteinase-activated anthrax toxin. Cancer Res. 2000;60(21):6061-6067.
Lyon et al., Self-hydrolyzing maleimides improve the stability and pharmacological properties of antibody-drug conjugates. Nat Biotechnol. 2014;32(10):1059-1062.
Mazor et al., Tolerogenic nanoparticles restore the antitumor activity of recombinant immunotoxins by mitigating immunogenicity. Proc Natl Acad Sci U S A. 2018;115(4):E733-E742.
Mccluskey et al., Targeting HER2-positive cancer cells with receptor-redirected anthrax protective antigen. Mol Oncol. 2013;7(3):440-451.
Mechaly et al., Changing the receptor specificity of anthrax toxin. mBio. 2012;3(3):e00088-12.
Mehner et al., Tumor cell-produced matrix metalloproteinase 9 (MMP-9) drives malignant progression and metastasis of basal-like triple negative breast cancer. Oncotarget. 2014;5(9):2736-2749.
Mijalis et al., A fully automated flow-based approach for accelerated peptide synthesis. Nat Chem Biol. 2017;13(5):464-466.
Miller et al., Anthrax protective antigen: prepore-to-pore conversion. Biochemistry. 1999;38(32):10432-10441.
Milne et al., Anthrax protective antigen forms oligomers during intoxication of mammalian cells. J Biol Chem. 1994;269(32):20607-20612.
Milne et al., Protective antigen-binding domain of anthrax lethal factor mediates translocation of a heterologous protein fused to its amino- or carboxy-terminus. Mol Microbiol. 1995;15(4):661-666.
Misale et al., Emergence of KRAS mutations and acquired resistance to anti-EGFR therapy in colorectal cancer. Nature. 2012;486(7404):532-536.
Mogridge et al., Stoichiometry of anthrax toxin complexes. Biochemistry. 2002;41(3):1079-1082.
Mourez et al., Mapping dominant-negative mutations of anthrax protective antigen by scanning mutagenesis. Proc Natl Acad Sci U S A. 2003;100(24):13803-13808.
Mukohara et al., Differential effects of gefitinib and cetuximab on non-small-cell lung cancers bearing epidermal growth factor receptor mutations. J Natl Cancer Inst. 2005;97(16):1185-1194.
Nahta et al., Insulin-like growth factor-I receptor/human epidermal growth factor receptor 2 heterodimerization contributes to trastuzumab resistance of breast cancer cells [published correction appears in Cancer Res. Nov. 15, 2008;68(22):9566]. Cancer Res. 2005;65(23):11118-11128.
Napolitano et al., Primary and Acquired Resistance of Colorectal Cancer to Anti-EGFR Monoclonal Antibody Can Be Overcome by Combined Treatment of Regorafenib with Cetuximab. Clin Cancer Res. 2015;21(13):2975-2983.
Nassi et al., PA63 channel of anthrax toxin: an extended beta-barrel. Biochemistry. 2002;41(5):1445-1450.
Nozaki et al., Targeting urokinase-type plasminogen activator and its receptor for cancer therapy. Anticancer Drugs. 2006;17(10):1109-1117.
Pannifer et al., Crystal structure of the anthrax lethal factor. Nature. 2001;414(6860):229-233.
Pastan et al., Immunotoxin therapy of cancer. Nat Rev Cancer. 2006;6(7):559-565.
Pohlmann et al., Resistance to Trastuzumab in Breast Cancer. Clin Cancer Res. 2009;15(24):7479-7491.
Press et al., Expression of the HER-2/neu proto-oncogene in normal human adult and fetal tissues. Oncogene. 1990;5(7):953-962.
Rabideau et al., Delivery of mirror image polypeptides into cells. Chem Sci. 2015;6(1):648-653.
Rabideau et al., Delivery of Non-Native Cargo into Mammalian Cells Using Anthrax Lethal Toxin. ACS Chem Biol. 2016;11(6):1490-1501.
Raker et al., The cAMP Pathway as Therapeutic Target in Autoimmune and Inflammatory Diseases. Front Immunol. 2016;7:123.

(56) References Cited

OTHER PUBLICATIONS

Ritter et al., Human breast cancer cells selected for resistance to trastuzumab in vivo overexpress epidermal growth factor receptor and ErbB ligands and remain dependent on the ErbB receptor network. Clin Cancer Res. 2007;13(16):4909-4919.

Rosovitz et al., Alanine-scanning mutations in domain 4 of anthrax toxin protective antigen reveal residues important for binding to the cellular receptor and to a neutralizing monoclonal antibody. J Biol Chem. 2003;278(33):30936-30944.

Sellman et al., Point mutations in anthrax protective antigen that block translocation. J Biol Chem. 2001;276(11):8371-8376.

Serezani et al., Cyclic AMP: master regulator of innate immune cell function. Am J Respir Cell Mol Biol. 2008;39(2):127-132.

Simon et al., Rapid flow-based peptide synthesis. Chembiochem. 2014;15(5):713-720.

Stetler-Stevenson et al., Tumor cell interactions with the extracellular matrix during invasion and metastasis. Annu Rev Cell Biol. 1993;9:541-573.

Subik et al., The Expression Patterns of ER, PR, HER2, CK5/6, EGFR, Ki-67 and AR by Immunohistochemical Analysis in Breast Cancer Cell Lines [published correction appears in Breast Cancer (Auckl). Oct. 16, 2018;12:1178223418806626]. Breast Cancer (Auckl). 2010;4:35-41.

Van Emburgh et al., Acquired resistance to EGFR-targeted therapies in colorectal cancer. Mol Oncol. 2014;8(6):1084-1094.

Vu et al., Trastuzumab: updated mechanisms of action and resistance in breast cancer. Front Oncol. 2012;2:62.

Ware et al., A mechanism of resistance to gefitinib mediated by cellular reprogramming and the acquisition of an FGF2-FGFR1 autocrine growth loop. Oncogenesis. 2013;2(3):e39.

Weigelt et al., HER2 signaling pathway activation and response of breast cancer cells to HER2-targeting agents is dependent strongly on the 3D microenvironment. Breast Cancer Res Treat. 2010;122(1):35-43.

Wilson et al., Diphtheria toxin and Pseudomonas aeruginosa exotoxin A: active-site structure and enzymic mechanism. Curr Top Microbiol Immunol. 1992;175:27-41.

Yamaizumi et al., One molecule of diphtheria toxin fragment A introduced into a cell can kill the cell. Cell. 1978;15(1):245-250.

Yamashiro et al., Trastuzumab treatment for breast cancer. The New England Journal of Medicine. 2006; 354, 2186.

Yano et al., Distribution and function of EGFR in human tissue and the effect of EGFR tyrosine kinase inhibition. Anticancer Res. 2003;23(5A):3639-3650.

Yewale et al., Epidermal growth factor receptor targeting in cancer: a review of trends and strategies. Biomaterials. 2013;34(34):8690-8707.

\* cited by examiner

SEQUENCE LISTING

```
<160> NUMBER OF SEQ ID NOS: 90

<210> SEQ ID NO 1
<211> LENGTH: 736
<212> TYPE: PRT
<213> ORGANISM: Bacillus anthracis

<400> SEQUENCE: 1

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
                20                  25                  30

Pro Met Val Val Thr Ser Ser Thr Gly Asp Leu Ser Ile Pro Ser
            35                  40                  45

Ser Glu Leu Glu Asn Ile Pro Ser Glu Asn Gln Tyr Phe Gln Ser Ala
        50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
    130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
            180                 185                 190

Tyr Thr Val Asp Val Lys Asn Lys Arg Thr Phe Leu Ser Pro Trp Ile
        195                 200                 205

Ser Asn Ile His Glu Lys Lys Gly Leu Thr Lys Tyr Lys Ser Ser Pro
    210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
                245                 250                 255
```

-continued

Val Ala Ala Tyr Pro Ile Val His Val Asp Met Glu Asn Ile Ile Leu
            260                 265                 270

Ser Lys Asn Glu Asp Gln Ser Thr Gln Asn Thr Asp Ser Glu Thr Arg
        275                 280                 285

Thr Ile Ser Lys Asn Thr Ser Thr Ser Arg Thr His Thr Ser Glu Val
    290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
        355                 360                 365

Asn Thr Gly Thr Ala Pro Ile Tyr Asn Val Leu Pro Thr Thr Ser Leu
    370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Asn Tyr Tyr Pro Ser Lys Asn
                405                 410                 415

Leu Ala Pro Ile Ala Leu Asn Ala Gln Asp Asp Phe Ser Ser Thr Pro
            420                 425                 430

Ile Thr Met Asn Tyr Asn Gln Phe Leu Glu Leu Glu Lys Thr Lys Gln
        435                 440                 445

Leu Arg Leu Asp Thr Asp Gln Val Tyr Gly Asn Ile Ala Thr Tyr Asn
    450                 455                 460

Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
                485                 490                 495

Lys Asp Leu Asn Leu Val Glu Arg Arg Ile Ala Ala Val Asn Pro Ser
            500                 505                 510

Asp Pro Leu Glu Thr Thr Lys Pro Asp Met Thr Leu Lys Glu Ala Leu
        515                 520                 525

Lys Ile Ala Phe Gly Phe Asn Glu Pro Asn Gly Asn Leu Gln Tyr Gln
    530                 535                 540

Gly Lys Asp Ile Thr Glu Phe Asp Phe Asn Phe Asp Gln Gln Thr Ser
545                 550                 555                 560

Gln Asn Ile Lys Asn Gln Leu Ala Glu Leu Asn Ala Thr Asn Ile Tyr
                565                 570                 575

Thr Val Leu Asp Lys Ile Lys Leu Asn Ala Lys Met Asn Ile Leu Ile
            580                 585                 590

Arg Asp Lys Arg Phe His Tyr Asp Arg Asn Asn Ile Ala Val Gly Ala
        595                 600                 605

Asp Glu Ser Val Val Lys Glu Ala His Arg Glu Val Ile Asn Ser Ser
    610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
                645                 650                 655

Ile Asn Asp Arg Tyr Asp Met Leu Asn Ile Ser Ser Leu Arg Gln Asp
            660                 665                 670

```
Gly Lys Thr Phe Ile Asp Phe Lys Tyr Asn Asp Lys Leu Pro Leu
            675                 680                 685
Tyr Ile Ser Asn Pro Asn Tyr Lys Val Asn Val Tyr Ala Val Thr Lys
    690                 695                 700
Glu Asn Thr Ile Ile Asn Pro Ser Glu Asn Gly Asp Thr Ser Thr Asn
705                 710                 715                 720
Gly Ile Lys Lys Ile Leu Ile Phe Ser Lys Lys Gly Tyr Glu Ile Gly
                725                 730                 735

<210> SEQ ID NO 2
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 2

Met Glu Val Lys Gln Glu Asn Arg Leu Leu Asn Glu Ser Glu Ser Ser
1               5                   10                  15
Ser Gln Gly Leu Leu Gly Tyr Tyr Phe Ser Asp Leu Asn Phe Gln Ala
            20                  25                  30
Pro Met Val Val Thr Ser Ser Thr Thr Gly Asp Leu Ser Ile Pro Ser
        35                  40                  45
Ser Glu Leu Glu Asn Ile Pro Ser Glu Asn Gln Tyr Phe Gln Ser Ala
    50                  55                  60
Ile Trp Ser Gly Phe Ile Lys Val Lys Lys Ser Asp Glu Tyr Thr Phe
65                  70                  75                  80
Ala Thr Ser Ala Asp Asn His Val Thr Met Trp Val Asp Asp Gln Glu
                85                  90                  95
Val Ile Asn Lys Ala Ser Asn Ser Asn Lys Ile Arg Leu Glu Lys Gly
            100                 105                 110
Arg Leu Tyr Gln Ile Lys Ile Gln Tyr Gln Arg Glu Asn Pro Thr Glu
        115                 120                 125
Lys Gly Leu Asp Phe Lys Leu Tyr Trp Thr Asp Ser Gln Asn Lys Lys
    130                 135                 140
Glu Val Ile Ser Ser Asp Asn Leu Gln Leu Pro Glu Leu Lys Gln Lys
145                 150                 155                 160
Ser Ser Asn Ser Arg Lys Lys Arg Ser Thr Ser Ala Gly Pro Thr Val
                165                 170                 175
Pro Asp Arg Asp Asn Asp Gly Ile Pro Asp Ser Leu Glu Val Glu Gly
            180                 185                 190
Tyr Thr Val Asp Val Lys Asn Lys Arg Thr Phe Leu Ser Pro Trp Ile
        195                 200                 205
Ser Asn Ile His Glu Lys Lys Gly Leu Thr Lys Tyr Lys Ser Ser Pro
    210                 215                 220
Glu Lys Trp Ser Thr Ala Ser Asp Pro Tyr Ser Asp Phe Glu Lys Val
225                 230                 235                 240
Thr Gly Arg Ile Asp Lys Asn Val Ser Pro Glu Ala Arg His Pro Leu
                245                 250                 255
Val Ala Ala Tyr Pro Ile Val His Val Asp Met Glu Asn Ile Ile Leu
            260                 265                 270
Ser Lys Asn Glu Asp Gln Ser Thr Gln Asn Thr Asp Ser Glu Thr Arg
        275                 280                 285
Thr Ile Ser Lys Asn Thr Ser Thr Ser Arg Thr His Thr Ser Glu Val
    290                 295                 300
```

-continued

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
        355                 360                 365

Asn Thr Gly Thr Ala Pro Ile Tyr Asn Val Leu Pro Thr Thr Ser Leu
    370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Tyr Tyr Pro Ser Lys Asn
                405                 410                 415

Leu Ala Pro Ile Ala Leu Asn Ala Gln Asp Asp Phe Ser Ser Thr Pro
                420                 425                 430

Ile Thr Met Asn Tyr Asn Gln Phe Leu Glu Leu Glu Lys Thr Lys Gln
            435                 440                 445

Leu Arg Leu Asp Thr Asp Gln Val Tyr Gly Asn Ile Ala Thr Tyr Asn
    450                 455                 460

Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
                485                 490                 495

Lys Asp Leu Asn Leu Val Glu Arg Arg Ile Ala Ala Val Asn Pro Ser
            500                 505                 510

Asp Pro Leu Glu Thr Thr Lys Pro Asp Met Thr Leu Lys Glu Ala Leu
    515                 520                 525

Lys Ile Ala Phe Gly Phe Asn Glu Pro Asn Gly Asn Leu Gln Tyr Gln
530                 535                 540

Gly Lys Asp Ile Thr Glu Phe Asp Phe Asn Phe Asp Gln Gln Thr Ser
545                 550                 555                 560

Gln Asn Ile Lys Asn Gln Leu Ala Glu Leu Asn Ala Thr Asn Ile Tyr
            565                 570                 575

Thr Val Leu Asp Lys Ile Lys Leu Asn Ala Lys Met Asn Ile Leu Ile
        580                 585                 590

Arg Asp Lys Arg Phe His Tyr Asp Arg Asn Asn Ile Ala Val Gly Ala
    595                 600                 605

Asp Glu Ser Val Val Lys Glu Ala His Arg Glu Val Ile Asn Ser Ser
610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
            645                 650                 655

Ile Asn Asp Arg Tyr Asp Met Leu Asn Ile Ser Ser Leu Arg Gln Asp
        660                 665                 670

Gly Lys Thr Phe Ile Asp Phe Lys Lys Tyr Ala Ala Lys Leu Pro Leu
    675                 680                 685

Tyr Ile Ser Asn Pro Asn Tyr Lys Val Asn Val Tyr Ala Val Thr Lys
    690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly

-continued

```
                    725                 730                 735
```

<210> SEQ ID NO 3
<211> LENGTH: 736
<212> TYPE: PRT
<213> ORGANISM: Artificial Sequence
<220> FEATURE:
<223> OTHER INFORMATION: Synthetic polypeptide

<400> SEQUENCE: 3

```
Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30

Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
    130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
            180                 185                 190

Tyr Thr Val Asp Val Lys Asn Lys Arg Thr Phe Leu Ser Pro Trp Ile
        195                 200                 205

Ser Asn Ile His Glu Lys Lys Gly Leu Thr Lys Tyr Lys Ser Ser Pro
    210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
                245                 250                 255

Val Ala Ala Tyr Pro Ile Val His Val Asp Met Glu Asn Ile Ile Leu
            260                 265                 270

Ser Lys Asn Glu Asp Gln Ser Thr Gln Asn Thr Asp Ser Glu Thr Arg
        275                 280                 285

Thr Ile Ser Lys Asn Thr Ser Thr Ser Arg Thr His Thr Ser Glu Val
    290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
```

```
                355                 360                 365
Asn Thr Gly Thr Ala Pro Ile Tyr Asn Val Leu Pro Thr Thr Ser Leu
370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Tyr Tyr Pro Ser Lys Asn
            405                 410                 415

Leu Ala Pro Ile Ala Leu Asn Ala Gln Asp Asp Phe Ser Ser Thr Pro
            420                 425                 430

Ile Thr Met Asn Tyr Asn Gln Phe Leu Glu Leu Lys Thr Lys Gln
        435                 440                 445

Leu Arg Leu Asp Thr Asp Gln Val Tyr Gly Asn Ile Ala Thr Tyr Asn
    450                 455                 460

Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
                485                 490                 495

Lys Asp Leu Asn Leu Val Glu Arg Arg Ile Ala Ala Val Asn Pro Ser
            500                 505                 510

Asp Pro Leu Glu Thr Thr Lys Pro Asp Met Thr Leu Lys Glu Ala Leu
        515                 520                 525

Lys Ile Ala Phe Gly Phe Asn Glu Pro Asn Gly Asn Leu Gln Tyr Gln
    530                 535                 540

Gly Lys Asp Ile Thr Glu Phe Asp Phe Asn Phe Asp Gln Gln Thr Ser
545                 550                 555                 560

Gln Asn Ile Cys Asn Gln Leu Ala Glu Leu Asn Ala Thr Asn Ile Tyr
                565                 570                 575

Thr Val Leu Asp Lys Ile Lys Leu Asn Ala Lys Met Asn Ile Leu Ile
            580                 585                 590

Arg Asp Lys Arg Phe His Tyr Asp Arg Asn Asn Ile Ala Val Gly Ala
        595                 600                 605

Asp Glu Ser Val Val Lys Glu Ala His Arg Glu Val Ile Asn Ser Ser
    610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
                645                 650                 655

Ile Asn Asp Arg Tyr Asp Met Leu Asn Ile Ser Ser Leu Arg Gln Asp
            660                 665                 670

Gly Lys Thr Phe Ile Asp Phe Lys Lys Tyr Ala Ala Lys Leu Pro Leu
        675                 680                 685

Tyr Ile Ser Asn Pro Asn Tyr Lys Val Asn Val Tyr Ala Val Thr Lys
    690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly
                725                 730                 735

<210> SEQ ID NO 4
<211> LENGTH: 736
<212> TYPE: PRT
<213> ORGANISM: Artificial Sequence
<220> FEATURE:
<223> OTHER INFORMATION: Synthetic polypeptide
```

<400> SEQUENCE: 4

```
Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30

Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
            115                 120                 125

Lys Gly Leu Asp Phe Lys Leu Tyr Trp Thr Asp Ser Gln Asn Lys Lys
130                 135                 140

Glu Val Ile Ser Ser Asp Asn Leu Gln Leu Pro Glu Leu Lys Gln Lys
145                 150                 155                 160

Ser Ser Asn Ser Arg Lys Lys Arg Ser Thr Ser Ala Gly Pro Thr Val
                165                 170                 175

Pro Asp Arg Asp Asn Asp Gly Ile Pro Asp Ser Leu Glu Val Glu Gly
            180                 185                 190

Tyr Thr Val Asp Val Lys Asn Lys Arg Thr Phe Leu Ser Pro Trp Ile
            195                 200                 205

Ser Asn Ile His Glu Lys Lys Gly Leu Thr Lys Tyr Lys Ser Ser Pro
210                 215                 220

Glu Lys Trp Ser Thr Ala Ser Asp Pro Tyr Ser Asp Phe Glu Lys Val
225                 230                 235                 240

Thr Gly Arg Ile Asp Lys Asn Val Ser Pro Glu Ala Arg His Pro Leu
                245                 250                 255

Val Ala Ala Tyr Pro Ile Val His Val Asp Met Glu Asn Ile Ile Leu
            260                 265                 270

Ser Lys Asn Glu Asp Gln Ser Thr Gln Asn Thr Asp Ser Glu Thr Arg
            275                 280                 285

Thr Ile Ser Lys Asn Thr Ser Thr Ser Arg Thr His Thr Ser Glu Val
290                 295                 300

His Gly Asn Ala Glu Val His Ala Ser Phe Phe Asp Ile Gly Gly Ser
305                 310                 315                 320

Val Ser Ala Gly Phe Ser Asn Ser Asn Ser Ser Thr Val Ala Ile Asp
                325                 330                 335

His Ser Leu Ser Leu Ala Gly Glu Arg Thr Trp Ala Glu Thr Met Gly
            340                 345                 350

Leu Asn Thr Ala Asp Thr Ala Arg Leu Asn Ala Asn Ile Arg Tyr Val
            355                 360                 365

Asn Thr Gly Thr Ala Pro Ile Tyr Asn Val Leu Pro Thr Thr Ser Leu
370                 375                 380

Val Leu Gly Lys Asn Gln Thr Leu Ala Thr Ile Lys Ala Lys Glu Asn
385                 390                 395                 400

Gln Leu Ser Gln Ile Leu Ala Pro Asn Asn Tyr Tyr Pro Ser Lys Asn
                405                 410                 415
```

```
Leu Ala Pro Ile Ala Leu Asn Ala Gln Asp Ala Ser Ser Thr Pro
            420                 425                 430

Ile Thr Met Asn Tyr Asn Gln Phe Leu Glu Leu Lys Thr Lys Gln
        435                 440                 445

Leu Arg Leu Asp Thr Asp Gln Val Tyr Gly Asn Ile Ala Thr Tyr Asn
450                 455                 460

Phe Glu Asn Gly Arg Val Arg Val Asp Thr Gly Ser Asn Trp Ser Glu
465                 470                 475                 480

Val Leu Pro Gln Ile Gln Glu Thr Thr Ala Arg Ile Ile Phe Asn Gly
                    485                 490                 495

Lys Asp Leu Asn Leu Val Glu Arg Arg Ile Ala Ala Val Asn Pro Ser
                500                 505                 510

Asp Pro Leu Glu Thr Thr Lys Pro Asp Met Thr Leu Lys Glu Ala Leu
            515                 520                 525

Lys Ile Ala Phe Gly Phe Asn Glu Pro Asn Gly Asn Leu Gln Tyr Gln
        530                 535                 540

Gly Lys Asp Ile Thr Glu Phe Asp Phe Asn Phe Asp Gln Gln Thr Ser
545                 550                 555                 560

Gln Asn Ile Cys Asn Gln Leu Ala Glu Leu Asn Ala Thr Asn Ile Tyr
                    565                 570                 575

Thr Val Leu Asp Lys Ile Lys Leu Asn Ala Lys Met Asn Ile Leu Ile
                580                 585                 590

Arg Asp Lys Arg Phe His Tyr Asp Arg Asn Asn Ile Ala Val Gly Ala
            595                 600                 605

Asp Glu Ser Val Val Lys Glu Ala His Arg Glu Val Ile Asn Ser Ser
        610                 615                 620

Thr Glu Gly Leu Leu Leu Asn Ile Asp Lys Asp Ile Arg Lys Ile Leu
625                 630                 635                 640

Ser Gly Tyr Ile Val Glu Ile Glu Asp Thr Glu Gly Leu Lys Glu Val
                    645                 650                 655

Ile Asn Asp Arg Tyr Asp Met Leu Asn Ile Ser Ser Leu Arg Gln Asp
                660                 665                 670

Gly Lys Thr Phe Ile Asp Phe Lys Lys Tyr Ala Ala Lys Leu Pro Leu
            675                 680                 685

Tyr Ile Ser Asn Pro Asn Tyr Lys Val Asn Val Tyr Ala Val Thr Lys
        690                 695                 700

Glu Asn Thr Ile Ile Asn Pro Ser Glu Asn Gly Asp Thr Ser Thr Asn
705                 710                 715                 720

Gly Ile Lys Lys Ile Leu Ile Phe Ser Lys Lys Gly Tyr Glu Ile Gly
                    725                 730                 735
```

<210> SEQ ID NO 5
<211> LENGTH: 192
<212> TYPE: PRT
<213> ORGANISM: Artificial Sequence
<220> FEATURE:
<223> OTHER INFORMATION: Synthetic polypeptide

<400> SEQUENCE: 5

```
Ala Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45
```

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

<210> SEQ ID NO 6
<211> LENGTH: 450
<212> TYPE: PRT
<213> ORGANISM: Artificial Sequence
<220> FEATURE:
<223> OTHER INFORMATION: Synthetic polypeptide

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
    450

<210> SEQ ID NO 7
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 7

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
            85                  90                  95

Thr Phe Gly Ala Gly Thr Lys Leu Glu Leu Lys Arg Thr Val Ala Ala
        100                 105                 110

Pro Ser Val Phe Ile Phe Pro Pro Ser Asp Glu Gln Leu Lys Ser Gly
    115                 120                 125

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 8
<211> LENGTH: 449
<212> TYPE: PRT
<213> ORGANISM: Artificial Sequence
<220> FEATURE:
<223> OTHER INFORMATION: Synthetic polypeptide

<400> SEQUENCE: 8

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270
```

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 9
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Leu Pro Ser Thr Gly Gly Lys
    450                 455

<210> SEQ ID NO 10
<211> LENGTH: 454
<212> TYPE: PRT
<213> ORGANISM: Artificial Sequence
<220> FEATURE:
<223> OTHER INFORMATION: Synthetic polypeptide

<400> SEQUENCE: 10

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

```
Lys Met Asn Ser Leu Gln Ser Asn Asp Thr Ala Ile Tyr Tyr Cys Ala
             85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Leu
            435                 440                 445

Pro Ser Thr Gly Gly Lys
    450

<210> SEQ ID NO 11
<211> LENGTH: 739
<212> TYPE: PRT
<213> ORGANISM: Artificial Sequence
<220> FEATURE:
<223> OTHER INFORMATION: Synthetic polypeptide
```

<400> SEQUENCE: 11

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30

Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
            100                 105                 110

Arg Leu Tyr Gln Ile Lys Ile Gln Tyr Gln Arg Glu Asn Pro Thr Glu
        115                 120                 125

Lys Gly Leu Asp Phe Lys Leu Tyr Trp Thr Asp Ser Gln Asn Lys Lys
    130                 135                 140

Glu Val Ile Ser Ser Asp Asn Leu Gln Leu Pro Glu Leu Lys Gln Lys
145                 150                 155                 160

Ser Ser Asn Ser Pro Gly Ser Gly Arg Ser Ala Ser Thr Ser Ala Gly
                165                 170                 175

Pro Thr Val Pro Asp Arg Asp Asn Asp Gly Ile Pro Asp Ser Leu Glu
        180                 185                 190

Val Glu Gly Tyr Thr Val Asp Val Lys Asn Lys Arg Thr Phe Leu Ser
    195                 200                 205

Pro Trp Ile Ser Asn Ile His Glu Lys Lys Gly Leu Thr Lys Tyr Lys
210                 215                 220

Ser Ser Pro Glu Lys Trp Ser Thr Ala Ser Asp Pro Tyr Ser Asp Phe
225                 230                 235                 240

Glu Lys Val Thr Gly Arg Ile Asp Lys Asn Val Ser Pro Glu Ala Arg
                245                 250                 255

His Pro Leu Val Ala Ala Tyr Pro Ile Val His Val Asp Met Glu Asn
        260                 265                 270

Ile Ile Leu Ser Lys Asn Glu Asp Gln Ser Thr Gln Asn Thr Asp Ser
    275                 280                 285

Glu Thr Arg Thr Ile Ser Lys Asn Thr Ser Thr Ser Arg Thr His Thr
290                 295                 300

Ser Glu Val His Gly Asn Ala Glu Val His Ala Ser Phe Phe Asp Ile
305                 310                 315                 320

Gly Gly Ser Val Ser Ala Gly Phe Ser Asn Ser Asn Ser Ser Thr Val
                325                 330                 335

Ala Ile Asp His Ser Leu Ser Leu Ala Gly Glu Arg Thr Trp Ala Glu
        340                 345                 350

Thr Met Gly Leu Asn Thr Ala Asp Thr Ala Arg Leu Asn Ala Asn Ile
    355                 360                 365

Arg Tyr Val Asn Thr Gly Thr Ala Pro Ile Tyr Asn Val Leu Pro Thr
    370                 375                 380

Thr Ser Leu Val Leu Gly Lys Asn Gln Thr Leu Ala Thr Ile Lys Ala
385                 390                 395                 400

Lys Glu Asn Gln Leu Ser Gln Ile Leu Ala Pro Asn Asn Tyr Tyr Pro

```
            405                 410                 415
Ser Lys Asn Leu Ala Pro Ile Ala Leu Asn Ala Gln Asp Asp Phe Ser
        420                 425                 430

Ser Thr Pro Ile Thr Met Asn Tyr Asn Gln Phe Leu Glu Leu Glu Lys
    435                 440                 445

Thr Lys Gln Leu Arg Leu Asp Thr Asp Gln Val Tyr Gly Asn Ile Ala
450                 455                 460

Thr Tyr Asn Phe Glu Asn Gly Arg Val Arg Val Asp Thr Gly Ser Asn
465                 470                 475                 480

Trp Ser Glu Val Leu Pro Gln Ile Gln Glu Thr Thr Ala Arg Ile Ile
                485                 490                 495

Phe Asn Gly Lys Asp Leu Asn Leu Val Glu Arg Arg Ile Ala Ala Val
            500                 505                 510

Asn Pro Ser Asp Pro Leu Glu Thr Lys Pro Asp Met Thr Leu Lys
        515                 520                 525

Glu Ala Leu Lys Ile Ala Phe Gly Phe Asn Glu Pro Asn Gly Asn Leu
    530                 535                 540

Gln Tyr Gln Gly Lys Asp Ile Thr Glu Phe Asp Phe Asn Phe Asp Gln
545                 550                 555                 560

Gln Thr Ser Gln Asn Ile Cys Asn Gln Leu Ala Glu Leu Asn Ala Thr
                565                 570                 575

Asn Ile Tyr Thr Val Leu Asp Lys Ile Lys Leu Asn Ala Lys Met Asn
            580                 585                 590

Ile Leu Ile Arg Asp Lys Arg Phe His Tyr Asp Arg Asn Asn Ile Ala
        595                 600                 605

Val Gly Ala Asp Glu Ser Val Val Lys Glu Ala His Arg Glu Val Ile
    610                 615                 620

Asn Ser Ser Thr Glu Gly Leu Leu Leu Asn Ile Asp Lys Asp Ile Arg
625                 630                 635                 640

Lys Ile Leu Ser Gly Tyr Ile Val Glu Ile Glu Asp Thr Glu Gly Leu
                645                 650                 655

Lys Glu Val Ile Asn Asp Arg Tyr Asp Met Leu Asn Ile Ser Ser Leu
            660                 665                 670

Arg Gln Asp Gly Lys Thr Phe Ile Asp Phe Lys Lys Tyr Ala Ala Lys
        675                 680                 685

Leu Pro Leu Tyr Ile Ser Asn Pro Asn Tyr Lys Val Asn Val Tyr Ala
    690                 695                 700

Val Thr Lys Glu Asn Thr Ile Ile Asn Pro Ser Glu Asn Gly Asp Thr
705                 710                 715                 720

Ser Thr Asn Gly Ile Lys Lys Ile Leu Ile Phe Ser Lys Lys Gly Tyr
                725                 730                 735

Glu Ile Gly

<210> SEQ ID NO 12
<211> LENGTH: 740
<212> TYPE: PRT
<213> ORGANISM: Artificial Sequence
<220> FEATURE:
<223> OTHER INFORMATION: Synthetic polypeptide

<400> SEQUENCE: 12

Met Glu Val Lys Gln Glu Asn Arg Leu Leu Asn Glu Ser Glu Ser Ser
1               5                   10                  15

Ser Gln Gly Leu Leu Gly Tyr Tyr Phe Ser Asp Leu Asn Phe Gln Ala
            20                  25                  30
```

```
Pro Met Val Val Thr Ser Ser Thr Gly Asp Leu Ser Ile Pro Ser
        35                  40                  45

Ser Glu Leu Glu Asn Ile Pro Ser Glu Asn Gln Tyr Phe Gln Ser Ala
    50                  55                  60

Ile Trp Ser Gly Phe Ile Lys Val Lys Lys Ser Asp Glu Tyr Thr Phe
65                  70                  75                  80

Ala Thr Ser Ala Asp Asn His Val Thr Met Trp Val Asp Asp Gln Glu
                85                  90                  95

Val Ile Asn Lys Ala Ser Asn Ser Asn Lys Ile Arg Leu Glu Lys Gly
                100                 105                 110

Arg Leu Tyr Gln Ile Lys Ile Gln Tyr Gln Arg Glu Asn Pro Thr Glu
            115                 120                 125

Lys Gly Leu Asp Phe Lys Leu Tyr Trp Thr Asp Ser Gln Asn Lys Lys
        130                 135                 140

Glu Val Ile Ser Ser Asp Asn Leu Gln Leu Pro Glu Leu Lys Gln Lys
145                 150                 155                 160

Ser Ser Asn Ser Gly Pro Leu Gly Met Leu Ser Gln Ser Thr Ser Ala
                165                 170                 175

Gly Pro Thr Val Pro Asp Arg Asp Asn Asp Gly Ile Pro Asp Ser Leu
            180                 185                 190

Glu Val Glu Gly Tyr Thr Val Asp Val Lys Asn Lys Arg Thr Phe Leu
        195                 200                 205

Ser Pro Trp Ile Ser Asn Ile His Glu Lys Lys Gly Leu Thr Lys Tyr
    210                 215                 220

Lys Ser Ser Pro Glu Lys Trp Ser Thr Ala Ser Asp Pro Tyr Ser Asp
225                 230                 235                 240

Phe Glu Lys Val Thr Gly Arg Ile Asp Lys Asn Val Ser Pro Glu Ala
                245                 250                 255

Arg His Pro Leu Val Ala Ala Tyr Pro Ile Val His Val Asp Met Glu
            260                 265                 270

Asn Ile Ile Leu Ser Lys Asn Glu Asp Gln Ser Thr Gln Asn Thr Asp
        275                 280                 285

Ser Glu Thr Arg Thr Ile Ser Lys Asn Thr Ser Thr Ser Arg Thr His
    290                 295                 300

Thr Ser Glu Val His Gly Asn Ala Glu Val His Ala Ser Phe Phe Asp
305                 310                 315                 320

Ile Gly Gly Ser Val Ser Ala Gly Phe Ser Asn Ser Asn Ser Ser Thr
                325                 330                 335

Val Ala Ile Asp His Ser Leu Ser Leu Ala Gly Glu Arg Thr Trp Ala
            340                 345                 350

Glu Thr Met Gly Leu Asn Thr Ala Asp Thr Ala Arg Leu Asn Ala Asn
        355                 360                 365

Ile Arg Tyr Val Asn Thr Gly Thr Ala Pro Ile Tyr Asn Val Leu Pro
    370                 375                 380

Thr Thr Ser Leu Val Leu Gly Lys Asn Gln Thr Leu Ala Thr Ile Lys
385                 390                 395                 400

Ala Lys Glu Asn Gln Leu Ser Gln Ile Leu Ala Pro Asn Asn Tyr Tyr
                405                 410                 415

Pro Ser Lys Asn Leu Ala Pro Ile Ala Leu Asn Ala Gln Asp Asp Phe
            420                 425                 430

Ser Ser Thr Pro Ile Thr Met Asn Tyr Asn Gln Phe Leu Glu Leu Glu
        435                 440                 445
```

```
Lys Thr Lys Gln Leu Arg Leu Asp Thr Asp Gln Val Tyr Gly Asn Ile
    450                 455                 460

Ala Thr Tyr Asn Phe Glu Asn Gly Arg Val Arg Val Asp Thr Gly Ser
465                 470                 475                 480

Asn Trp Ser Glu Val Leu Pro Gln Ile Gln Glu Thr Thr Ala Arg Ile
                485                 490                 495

Ile Phe Asn Gly Lys Asp Leu Asn Leu Val Glu Arg Arg Ile Ala Ala
                500                 505                 510

Val Asn Pro Ser Asp Pro Leu Glu Thr Thr Lys Pro Asp Met Thr Leu
                515                 520                 525

Lys Glu Ala Leu Lys Ile Ala Phe Gly Phe Asn Glu Pro Asn Gly Asn
530                 535                 540

Leu Gln Tyr Gln Gly Lys Asp Ile Thr Glu Phe Asp Phe Asn Phe Asp
545                 550                 555                 560

Gln Gln Thr Ser Gln Asn Ile Cys Asn Gln Leu Ala Glu Leu Asn Ala
                565                 570                 575

Thr Asn Ile Tyr Thr Val Leu Asp Lys Ile Lys Leu Asn Ala Lys Met
                580                 585                 590

Asn Ile Leu Ile Arg Asp Lys Arg Phe His Tyr Asp Arg Asn Asn Ile
                595                 600                 605

Ala Val Gly Ala Asp Glu Ser Val Val Lys Glu Ala His Arg Glu Val
610                 615                 620

Ile Asn Ser Ser Thr Glu Gly Leu Leu Leu Asn Ile Asp Lys Asp Ile
625                 630                 635                 640

Arg Lys Ile Leu Ser Gly Tyr Ile Val Glu Ile Glu Asp Thr Glu Gly
                645                 650                 655

Leu Lys Glu Val Ile Asn Asp Arg Tyr Asp Met Leu Asn Ile Ser Ser
                660                 665                 670

Leu Arg Gln Asp Gly Lys Thr Phe Ile Asp Phe Lys Lys Tyr Ala Ala
                675                 680                 685

Lys Leu Pro Leu Tyr Ile Ser Asn Pro Asn Tyr Lys Val Asn Val Tyr
                690                 695                 700

Ala Val Thr Lys Glu Asn Thr Ile Ile Asn Pro Ser Glu Asn Gly Asp
705                 710                 715                 720

Thr Ser Thr Asn Gly Ile Lys Lys Ile Leu Ile Phe Ser Lys Lys Gly
                725                 730                 735

Tyr Glu Ile Gly
            740

<210> SEQ ID NO 13
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 13

Arg Lys Lys Arg
1

<210> SEQ ID NO 14
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
```

```
<222> LOCATION: (3)..(3)
<223> OTHER INFORMATION: Xaa can be any naturally occurring amino acid

<400> SEQUENCE: 14

Leu Pro Xaa Thr Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 15

Leu Pro Lys Thr Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 16

Leu Pro Ala Thr Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 17

Leu Pro Asn Thr Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 18

Leu Pro Glu Thr Gly
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 19

Leu Pro Xaa Ala Gly
1               5

<210> SEQ ID NO 20
```

```
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 20

Leu Pro Asn Ala Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 21

Leu Pro Xaa Thr Ala
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Leu Pro Asn Thr Ala
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 23

Leu Gly Xaa Thr Gly
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 24

Leu Gly Ala Thr Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polypeptide
<220> FEATURE:
```

```
<221> NAME/KEY: misc_feature
<222> LOCATION: (3)..(3)
<223> OTHER INFORMATION: Xaa can be any naturally occurring amino acid

<400> SEQUENCE: 25

Ile Pro Xaa Thr Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 26

Ile Pro Asn Thr Gly
1               5

<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 27

Ile Pro Glu Thr Gly
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Xaa can be Gln or Lys
<220> FEATURE:
<221> NAME/KEY: MISC_FEATURE
<222> LOCATION: (5)..(5)
<223> OTHER INFORMATION: Xaa can be Ala or Ser

<400> SEQUENCE: 28

Leu Pro Xaa Thr Xaa Thr
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Ala or Ser

<400> SEQUENCE: 29

Leu Pro Xaa Thr Xaa Thr
1               5

<210> SEQ ID NO 30
```

```
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 30

Leu Pro Ser Thr Ser
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 31

Leu Pro Ile Thr Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 32

Leu Pro Asp Thr Ala
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 33

Ser Pro Lys Thr Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 34

Leu Ala Glu Thr Gly
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 35

Leu Ala Ala Thr Gly
1               5

<210> SEQ ID NO 36
<211> LENGTH: 5
```

```
<212> TYPE: PRT
<213> ORGANISM: Artificial Sequence
<220> FEATURE:
<223> OTHER INFORMATION: Synthetic polypeptide

<400> SEQUENCE: 36

Leu Ala His Thr Gly
1               5

<210> SEQ ID NO 37
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 37

Leu Ala Ser Thr Gly
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 38

Leu Pro Leu Thr Gly
1               5

<210> SEQ ID NO 39
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 39

Leu Ser Arg Thr Gly
1               5

<210> SEQ ID NO 40
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 40

Val Pro Asp Thr Gly
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 41

Ile Pro Gln Thr Gly
1               5

<210> SEQ ID NO 42
<211> LENGTH: 5
<212> TYPE: PRT
```

```
<213> ORGANISM: Artificial Sequence
<220> FEATURE:
<223> OTHER INFORMATION: Synthetic polypeptide

<400> SEQUENCE: 42

Tyr Pro Arg Arg Gly
1               5

<210> SEQ ID NO 43
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 43

Leu Pro Met Thr Gly
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 44

Leu Ala Phe Thr Gly
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 45

Leu Pro Gln Thr Ser
1               5

<210> SEQ ID NO 46
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 46

Asn Pro Gln Ser
1

<210> SEQ ID NO 47
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 47

Leu Pro Ser Thr
1

<210> SEQ ID NO 48
<211> LENGTH: 4
<212> TYPE: PRT
<213> ORGANISM: Artificial Sequence
```

```
<220> FEATURE:
<223> OTHER INFORMATION: Synthetic polypeptide

<400> SEQUENCE: 48

Asn Ser Lys Thr
1

<210> SEQ ID NO 49
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 49

Asn Pro Gln Thr
1

<210> SEQ ID NO 50
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 50

Asn Ala Lys Thr
1

<210> SEQ ID NO 51
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 51

Leu Pro Ile Thr
1

<210> SEQ ID NO 52
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 52

Leu Ala Glu Thr
1

<210> SEQ ID NO 53
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Asp, Glu, Ala, Asn, Gln, Lys, or Arg

<400> SEQUENCE: 53

Leu Pro Xaa Thr Gly
1               5

<210> SEQ ID NO 54
```

```
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Asp, Glu, Ala, Asn, Gln, Lys, or Arg

<400> SEQUENCE: 54

Leu Pro Xaa Thr
1

<210> SEQ ID NO 55
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Lys, Glu, Asn, Gln, or Ala

<400> SEQUENCE: 55

Leu Pro Xaa Thr Gly
1               5

<210> SEQ ID NO 56
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Lys, Glu, Asn, Gln, or Ala

<400> SEQUENCE: 56

Leu Pro Xaa Thr
1

<210> SEQ ID NO 57
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Lys, Ser, Glu, Leu, Ala, or Asn

<400> SEQUENCE: 57

Leu Pro Xaa Thr Gly
1               5

<210> SEQ ID NO 58
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (3)..(3)
<223> OTHER INFORMATION: Xaa can be Lys, Ser, Glu, Leu, Ala, or Asn

<400> SEQUENCE: 58
```

```
Leu Pro Xaa Thr
1

<210> SEQ ID NO 59
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 59

Leu Pro Ser Thr Gly Gly
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 60

Gly Pro Leu Gly Ile Ala Gly Gln
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be Ser or Thr

<400> SEQUENCE: 61

Pro Xaa Xaa His Tyr Xaa
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 62

Thr Gly Arg Gly Pro Ser Trp Val
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 63

Ser Ala Arg Gly Pro Ser Arg Trp
1               5

<210> SEQ ID NO 64
```

```
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 64

Thr Ala Arg Gly Pro Ser Phe Lys
1               5

<210> SEQ ID NO 65
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 65

Leu Ser Gly Arg Ser Asp Asn His
1               5

<210> SEQ ID NO 66
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 66

Gly Gly Trp His Thr Gly Arg Asn
1               5

<210> SEQ ID NO 67
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 67

His Thr Gly Arg Ser Gly Ala Leu
1               5

<210> SEQ ID NO 68
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 68

Pro Leu Thr Gly Arg Ser Gly Gly
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 69

Leu Thr Gly Arg Ser Gly Ala
1               5

<210> SEQ ID NO 70
<211> LENGTH: 8
```

```
<212> TYPE: PRT
<213> ORGANISM: Artificial Sequence
<220> FEATURE:
<223> OTHER INFORMATION: Synthetic polypeptide

<400> SEQUENCE: 70

Ser Ser Arg Gly Pro Ala Tyr Leu
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 71

Arg Gly Pro Ala Thr Pro Ile Met
1               5

<210> SEQ ID NO 72
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 72

Arg Gly Pro Ala
1

<210> SEQ ID NO 73
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 73

Gly Leu Lys Arg
1

<210> SEQ ID NO 74
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 74

Ile Pro Glu Asn Phe Phe Gly Asn
1               5

<210> SEQ ID NO 75
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 75

Asx Pro Tyr Gly Leu Gly Ser Pro
1               5

<210> SEQ ID NO 76
<211> LENGTH: 8
<212> TYPE: PRT
```

<213> ORGANISM: Artificial Sequence
<220> FEATURE:
<223> OTHER INFORMATION: Synthetic polypeptide

<400> SEQUENCE: 76

His Pro Ser Ala Phe Ser Glu Ala
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 77

Gly Pro Gln Gly Leu Leu Gly Ala
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 78

Gly Pro Ala Gly Leu Ser Val Leu
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 79

Gly Pro Ala Gly Ile Asn Thr Lys
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 80

Asp Ala Ala Ser Leu Leu Gly Leu
1               5

<210> SEQ ID NO 81
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 81

Arg Pro Ala Asn Met Thr Ser Pro
1               5

<210> SEQ ID NO 82
<211> LENGTH: 8
<212> TYPE: PRT
<213> ORGANISM: Artificial Sequence

```
<220> FEATURE:
<223> OTHER INFORMATION: Synthetic polypeptide

<400> SEQUENCE: 82

Pro Pro Gly Ala Tyr His Gly Ala
1               5

<210> SEQ ID NO 83
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 83

Leu Arg Ala Tyr Leu Leu Pro Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 84

Ser Pro Tyr Glu Leu Lys Ala Leu
1               5

<210> SEQ ID NO 85
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 85

Thr Ala Ala Ala Leu Thr Ser Cys
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 86

Gly Pro Glu Gly Leu Arg Val Gly
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 87

Gly His Ala Arg Leu Val His Val
1               5

<210> SEQ ID NO 88
<211> LENGTH: 8
<212> TYPE: PRT
<213> ORGANISM: Artificial Sequence
<220> FEATURE:
```

```
<223> OTHER INFORMATION: Synthetic polypeptide

<400> SEQUENCE: 88

Gln Pro Val Gly Ile Asn Thr Ser
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 89

Arg Arg Ile Asn Arg Glu
1               5

<210> SEQ ID NO 90
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 90

Arg Arg Ile Asn
1
```

FUNCTIONALIZATION OF BACTERIAL EFFECTOR TRANSLOCASE PROTEIN BY CHEMICAL CONJUGATION

RELATED APPLICATIONS

This application claims the benefit of the filing date under 35 U.S.C. § 119 of U.S. Provisional Application Ser. No. 62/721,772, filed Aug. 23, 2018, the entire contents of which are incorporated by reference herein.

FIELD OF INVENTION

The present invention relates to compositions and methods associated with antibody-bacterial effector translocase protein conjugates. Some aspects of the present invention relate to treating disorders using the antibody-bacterial effector translocase protein conjugates. Further aspects of the present invention relate to methods of chemically conjugating and synthesizing bacterial effector translocase protein-antibody conjugates.

BACKGROUND OF INVENTION

Antibodies, such as immunoglobulin G (IgG), are currently one of the most important classes of therapeutics. Due to its wide application and favorable in vivo properties, there has been significant interest in using IgG as a drug carrier. Although some success has been achieved with small molecules and self-translocating protein toxins, the antibody-mediated delivery of the majority of proteins has been elusive, because of a failure to deliver the drug to the cytosol where it can act on targets.

SUMMARY OF INVENTION

The invention in some aspects is a targeted protein delivery system composed of a bacterial effector translocase protein conjugated (preferably by chemical conjugation) to an antibody or other antigen binding molecule. The targeted cytosolic delivery of different protein cargos using different antibodies in multiple cells using this system has been demonstrated herein. The versatility of the system enables the development of highly effective targeted delivery of therapeutic agents to cellular cytosol while avoiding off target effects. The invention, in some aspects, is a composition comprising an antibody-protective antigen (Ab-PA) comprising an antibody linked to a protective antigen, wherein the protective antigen comprises a protein translocase.

The disclosure provides, in some aspects, a composition, comprising a bacterial effector translocase protein having an N-terminus, a C-terminus and internal amino acids, wherein a linker is conjugated to at least one of the internal amino acids referred to as a first internal amino acid, wherein the linker forms a side chain; and an antibody, wherein the antibody is linked to the bacterial effector translocase protein via the side chain. In some embodiments the linker is not a disulfide bond.

In some embodiments the composition is homogenous. A homogenous composition includes conjugates composed of a single antibody linked to a single bacterial effector translocation protein.

In some embodiments, the antibody is linked to the bacterial effector translocase protein via chemical conjugation. In one embodiment, the chemical conjugation comprises sortase-mediated ligation. In other embodiments, the sortase-mediated ligation occurs between C-terminus of a heavy chain of the antibody and the linker. In some embodiments, the first internal amino acid conjugated to the linker is positioned at least 10 amino acids away from the N-terminus of the bacterial effector translocase protein. In another embodiment, the first internal amino acid conjugated to the linker is positioned at least 200 amino acids away from the N-terminus of the bacterial effector translocase protein. In some embodiments, the first internal amino acid conjugated to the linker is positioned at least 10 amino acids away from the C-terminus of the bacterial effector translocase protein.

In some embodiments, the antibody is an immunoglobulin G (IgG) antibody. In one embodiment, the IgG antibody is a monoclonal antibody.

In some embodiments, the bacterial effector translocase protein comprises at least one mutation relative to a wild type bacterial effector translocase protein. In one embodiment, the at least one mutation is selected from the group consisting of: an amino acid residue substitution and an insertion. In another embodiment, the at least one mutation affects the protease cleavage site. In some embodiments, the affected protease cleavage site comprises a sequence specific for cleavage by furin-family proteases, matrix metalloproteinase (MMP) or urokinase-type plasminogen activator (uPA). In another embodiment, the mutation is the insertion of one or more amino acids. In some embodiments, the inserted amino acids comprise a sortase recognition cleavage sequence.

In one embodiment, the bacterial effector translocase protein is the anthrax lethal toxin translocase protective antigen (PA). In another embodiment, the PA comprises one cysteine mutation relative to a wild-type anthrax lethal toxin translocase protective antigen. In a further embodiment, the cysteine mutation occurs at the lysine 563 position of SEQ ID NO: 2.

In some embodiments, the cysteine mutation of the PA is cross-linked to a short D-peptide linker, wherein the short D-peptide linker comprises an N-terminal tri-glycine, to form $G_3$-PA. In one embodiment, the PA and the short D-peptide linker are cross-linked via bromoacetamide. In another embodiment, the $G_3$-PA is ligated to the antibody via a sortase. In one embodiment, the sortase is a triple mutant sortase (SrtA*).

In some embodiments, the composition described herein further comprises a cargo molecule. In one embodiment, the bacterial effector translocase protein comprises a second internal amino acid conjugated to a linker to form a second side chain, and wherein the cargo molecule is linked to the bacterial effector translocase protein via the second side chain. In some embodiments, the cargo molecule is selected from the group consisting of: a nucleic acid, a protein, a peptide, and a small molecule. In other embodiments, the cargo molecule is a therapeutic cargo molecule. In a further embodiment, the cargo molecule is selected from the group consisting of: Diphtheria toxin A (DTA), β-lactamase, Pseudomonas exotoxin A, dihydrofolate reductase, GFP, DARPin, L affibody, D affibody, L peptides, D peptides and Ras protease RRSP.

In another aspect, the disclosure provides a bacterial effector translocase protein having an N-terminus, a C-terminus and internal amino acids comprising a linker conjugated to at least one of the internal amino acids referred to as a first internal amino acid, wherein the linker forms a side chain.

In some embodiments, the linker is a glycine-rich linker. In one embodiment, the glycine-rich linker is a polyglycine linker.

In some embodiments, the bacterial effector translocase protein comprises one or more mutations relative to a wild-type bacterial effector translocase protein. In other embodiments, the one of more mutations remove native receptor-binding ability of the bacterial effector translocase protein. In another embodiment, the one or more mutations comprise an insertion, an amino acid residue substitution, or a deletion. In a further embodiment, the one or more mutations comprise an amino acid substitution from a wild-type amino acid to a cysteine residue.

In some embodiments, the bacterial effector translocase protein is at least 95% identical to the wild-type bacterial effector translocase protein. In another embodiment, the bacterial effector translocase protein is at least 98% identical to the wild-type bacterial effector translocase protein.

In some embodiments, the bacterial effector translocase protein is a pore-forming protein. In one embodiment, the pore-forming protein is selected from the group consisting of: translocation domain (T domain) of diphtheria toxin, Vibrio cholerae, aerolysin, alpha-toxin, protective antigen (PA), perfringolysin O, listeriolysin O, intermedilysin, colicin A, and HlyA. In another embodiment, the pore-forming protein is protective antigen (PA). In some embodiments, the PA comprises a cysteine mutation of a PA(N682A, D683A) mutant. In another embodiment, the cysteine mutation the cysteine mutation occurs at the lysine 563 position of SEQ ID NO: 2.

In another aspect, the disclosure provides a method of treating a disorder in a subject, the method comprising administering to the subject a pharmaceutically acceptable dose of a bacterial effector translocase protein having an N-terminus, a C-terminus and internal amino acids, wherein a linker is conjugated to at least one of the internal amino acids, referred to as a first internal amino acid, wherein the linker forms a side chain, an antibody, wherein the antibody is linked to the bacterial effector translocase protein via the side chain; and a cargo molecule, wherein the cargo molecule is delivered to a cell of the subject to treat the disorder.

In one embodiment, the disorder is cancer.

In some embodiments, the bacterial effector translocase protein comprises a second internal amino acid conjugated to a linker to form a second side chain, and wherein the cargo molecule is linked to the bacterial effector translocase protein via the second side chain. In another embodiment, the cargo molecule is linked to an N-terminal domain of lethal factor (LFN) and is not linked to the bacterial effector translocase protein. In some embodiments, the cargo molecule is selected from the group consisting of: a nucleic acid, a protein, a peptide, and a small molecule. In another embodiment, the cargo molecule is a therapeutic cargo molecule. In some embodiments, the cargo molecule is selected from the group consisting of: Diphtheria toxin A (DTA), β-lactamase, *Pseudomonas* exotoxin A, dihydrofolate reductase, GFP, DARPin, L affibody, D affibody, L peptides, D peptides and Ras protease RRSP.

The translocase protein can be manipulated in order to alter protease specificity. As a results the conjugates form highly specific delivery vehicles that can only be activated by the concurrent presence of two entities on cell surface (antigen and specific protease). For instance, it has been demonstrated that a protein toxin delivered by the conjugates of the invention had significantly increased therapeutic window and effectively inhibited tumor growth both in vitro and in vivo. It has also been demonstrated herein that the methods are also useful for overcoming antibody drug resistance in refractory cancer cell lines.

The disclosure also provides, in some aspects, a method of chemically conjugating an antibody to a bacterial effector translocase protein, the method comprising: (a) synthesizing a bacterial effector translocase protein comprising one cysteine mutation; (b) crosslinking a short D-peptide linker with an N-terminal tri-glycine to the cysteine; (c) ligating the bacterial effector translocase protein variant with the short D-peptide linker and N-terminal tri-glycine to an antibody, wherein the antibody comprises heavy chain C-terminal LPSTGG (SEQ ID NO: 59) tags, and wherein the ligation is performed by a sortase.

In some embodiments, the linker and bacterial effector translocase protein variant are crosslinked through a bromoacetamide. In another embodiment, the sortase is a triple mutant sortase (SrtA*).

Each of the embodiments of the invention can encompass various recitations made herein. It is, therefore, anticipated that each of the recitations of the invention involving any one element or combinations of elements can, optionally, be included in each aspect of the invention.

BRIEF DESCRIPTION OF THE DRAWINGS

FIGS. 1A-1B show a modular design of an immunoglobulin (IgG) protective antigen (PA) conjugate. FIG. 1A shows the proposed mechanism of antibody-mediated delivery by the IgG-mPA system. FIG. 1B shows the different possible strategies of conjugating mPA to IgG. Recombinant expression was ruled out due the potential impact on the functionality of one or both IgG and PA.

FIGS. 2A-2D depict the preparation of the IgG-mPA conjugate using sortase-mediated ligation. FIG. 2A shows mPA(K563C) added to a polyglycine linker by either maleimide or bromoacetamide (upper panel) before sortagging onto the IgG with LPSTGG (SEQ ID NO: 59) tags (lower panel). In FIG. 2B, the resulting product mixture of the IgG-mPA and the IgG-$(mPA)_2$ was purified to homogeneous IgG-mPA by standard size exclusion and anion exchange chromatography. The IgG used in this experiment was Trastuzumab (Tmab). FIG. 2C shows that free combinations of different antibodies and different mPA variants enable orthogonally targeted delivery of different protein cargos. FIG. 2D is a schematic of the IgG-mPA variant delivering a protein cargo to a specific cell type, using dual targeting of a particular antigen and a specific protease.

FIGS. 3A-3F show that the IgG-mPA delivers different protein cargos to different cell types in a receptor-specific manner. FIG. 3A shows HER2-expressing BT474 cells treated with ten-fold serial dilutions of Tmab or Tmab conjugates with or without 10 nM LD (a fusion protein between $LF_N$, the PA prepore binding domain and DTA, the catalytic domain of diphtheria toxin) in medium containing 10% FBS for 72 hours. mPAA stands for mPA(F427A), a translocation-deficient mutant of mPA. Cell viabilities were measured by CellTitor-Glo assay and normalized to untreated cells. FIG. 3B shows EGFR-expressing A431 cells treated with cetuximab (Cmab) or Cmab conjugates the same way as described in FIG. 3A. FIG. 3C shows a viability comparison between HER2-positive BT474 and HER2-negative BT549 cells after treatment with Tmab-mPA and 10 nM LD. FIG. 3D shows a viability comparison between EGFR-positive A431 and EGFR-negative Jurkat cells after treatment with Cmab-mPA and 10 nM LD. FIG. 3E shows EGFR-expressing TNBC MDA-MB-231 cells treated with 20 nM edema factor (EF) or LD and different Cmab or Tmab conjugates for 2 hours. The intracellular cAMP concentrations were measured by an ELISA-based competition assay.

FIG. 3F shows MDA-MB-231 cells incubated with different concentrations of LR ($LF_N$-RRSP; $LF_N$-Ras/Rap1-specific endopeptidase) in the presence of 50 nM Cmab-mPA for 24 hours. 50 nM of LR with different Cmab or Tmab conjugate controls were also included.

FIGS. 4A-4D show that resistance to HER2- or EGFR-based therapies can be overcome by Tmab- or Cmab-delivered DTA. Different refractory cancer cell lines were treated with either IgG or IgG-mPA/LD in medium containing 10% FBS for 72 hours. The Cmab resistant cell lines were also treated with Gefitinib, an FDA-approved EGFR inhibitor. The relative cell viabilities were measured by CellTitor-Glo assay and normalized to untreated cells. FIG. 4A shows human ovarian cancer cell line SKOV-3. FIGS. 4B-4C show human non-small-cell lung cancer (NSCLC) cell lines A549 and H441, respectively. FIG. 4D shows HCT-116, a human colon cancer cell line. FIGS. 4E-4F show triple negative breast cancer (TNBC) cell lines BT549 and MDA-MB-231, respectively.

FIGS. 5A-5E show that orthogonal targeting IgG-mPA variants require the presence of both the antigen and the protease for cargo delivery and hence have less off-target effects. FIG. 5A shows the in vitro cleavage of Cmab-mPA, Cmab-mPA-uPA (Cmab-uPA), and Cmab-mPA-MMP (Cmab-MMP) by furin, uPA, or MMP-9. The tested Cmab conjugates were incubated with the corresponding protease at 37° C. for the times indicated. The samples were analyzed by SDS-PAGE and stained with Coomassie dye. FIG. 5B shows EGFR/uPA-positive MDA-MB-231 and BT549 cells treated with or without 10 nM LD in the presence of ten-fold serial dilutions of Cmab-mPA-uPA for 72 hours before being subjected to the CellTitor-Glo assay. FIG. 5C shows MDA-MB-231 and BT549 cells, which also express MMP, treated with Cmab-mPA-MMP and LD. FIG. 5D shows EGFR-positive and uPA/MMP-negative H2030 cells incubated with serial dilutions of all three Cmab conjugates and 10 nM LD. FIG. 5E shows the cytotoxicities of LD delivered by wild-type PA or different Cmab-mPA variants tested in HMEC-1, a normal human microvascular endothelial cell line.

FIGS. 6A-6C show the in vivo delivery of LD mediated by Cmab-mPA variants. FIG. 6A shows the microscopic appearance of kidney and liver of mice 48 hours after intravenous (i.v.) injection with PBS or 1 mg/kg of LD plus 15 mg/kg of Cmab-mPA variants. FIG. 6B shows whole-body PET images of mice 6 hours after i.v. injection of 89Zr-labeled wild-type PA, Cmab, or Cmab-mPA-uPA (1 mg/kg). FIG. 6C shows a comparison of relative blood concentration between Cmab-mPA-uPA and wild-type PA. Blood samples (n=4) were taken at different time points and measured for their radioactivity as described below. Relative % ID/g was normalized to time O.

FIG. 7 shows an activity comparison between Tmab-mPA, Tmab-M-mPA, and Tmab-$(GGS)_7$-M-mPA. BT474 cells were treated with 10 nM LD and different Tmab-mPA variants for 72 hours before being subject to CellTitor-Glo. The relative viability is normalized to no treatment. Each data point is a triplicate.

FIG. 8 shows an activity comparison between Tmab-mPA and Tmab-$(mPA)_2$ in the presence of 10 nM LD.

FIG. 9 shows an activity comparison between Cmab-mPA and Cmab-M-(mPA). A549 cells were treated with both proteins at the indicated concentrations in the presence of 10 nM LD for 72 hours. The cell viability was measured by CellTiter-Glo and normalized to no treatment group. Each data point is a triplicate.

FIG. 10 shows that both BT549 and Jurkat cells are susceptible to LD in the presence of wild-type PA. Cells were treated with 10-fold serial dilutions of wild-type PA in the presence of 10 nM of LD. Viability was measured after 72 hours by CellTiter-Glo.

FIGS. 11A-11C show that different cell lines respond differently to Cmab-mPA and Tmab-mPA in the presence of 10 nM of LD. The cells were treated with 10-fold serial dilutions of Cmab-mPA or Tmab-mPA with 10 nM of LD. Viability was measured by CellTiter-Glo as described in the methods section. FIG. 11A shows the viability of HER2-positive and EGFR-negative BT474 cells. FIG. 11B shows the viability of HER2-negative and EGFR-positive A549 cells. FIG. 11C shows the viability of HER2-negative and EGFR-positive HCT116 cells.

DETAILED DESCRIPTION OF INVENTION

Figure 2A:
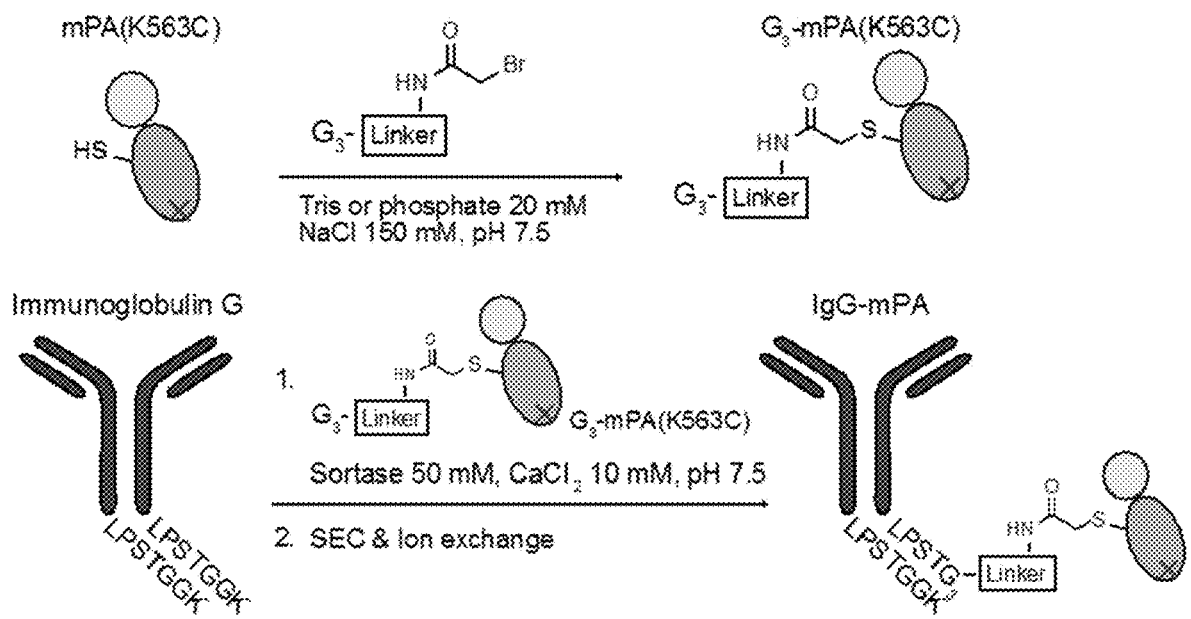

Proteins such as hormones, cytokines and antibodies have emerged as one of the most important classes of drugs. However, most proteins cannot be used against intracellular targets due to their inability to reach the cytosol. Although gene delivery has been extensively used to introduce exogenous proteins into cells, it risks permanent disruption of the endogenous genome. Several approaches including peptides, polymers, and nanoparticles have been developed for direct protein delivery but most either lack specificity or have limited endosomal release, two key features of an ideal protein delivery strategy.

Monoclonal antibodies (mAbs) are useful molecules for targeting. They have been exploited in almost every branch of biomedical research and are widely used in humans for the treatments of immune-related diseases and cancer as one of the most successful and important therapeutic strategies. Currently, more than 70 mAb drugs have been approved and more than 550 antibodies are in clinical development. Among them, the predominant form is immunoglobulin G (IgG). IgG is composed of two distinct functional units: the antigen binding fragment (Fab), which confers antigen specificity, and the constant fragment (Fc), which interacts with the immune cells and extends the antibody half-life in vivo. Due to their great versatility and clinical relevance, there has been a considerable amount of interest in using IgG molecules as drug carriers to target specific cell types. Antibody-drug conjugates (ADCs) and immunotoxins are two examples of using mAbs or mAb fragments to deliver cytotoxic moieties to cancer cells. During its general mechanism of action, the ADC is endocytosed into the endosome/lysosome via the antibody-receptor interaction, where the small molecule drug is released from the antibody and diffuses out of the endosome into the cytosol. In the case of immunotoxin, after its release from the antibody, the protein toxin self-transports into the cytosol due to its unique natural toxin-derived property. However, for the majority of proteins, cytosolic delivery using mAbs has remained elusive due to their inability to escape the endosome.

Pathogenic bacteria often express toxins that are capable of delivering effector proteins into the cytosol of cells. Several types of translocation systems for delivery of proteins into host cells exist in nature. Among them, anthrax lethal toxin is an example of using a translocase to deliver protein toxins from the endosome to the cytosol by *Bacillus anthracis*. Anthrax lethal toxin comprises three effector proteins: the translocase protective antigen (PA), and the effector proteins, lethal factor (LF) and edema factors (EF). During translocation, $PA_{83}$ interacts with its receptors on a host cell surface and then is proteolytically cleaved into $PA_{63}$ by a furin-family protease. After cleavage, $PA_{63}$ oligomerizes into a heptameric or octameric pre-pore, and three or four LF molecules bind to the pre-pore through their N-terminal domain, $LF_N$, with 1-2 nM affinity. The entire complex is subsequently endocytosed and the acidic pH in the endosome causes a conformational change of the pre-pore, resulting in the formation of a transmembrane pore, which enables the translocation of LF from the endosome into the cytosol.

The invention, in some aspects, overcomes limitations and obstacles of the prior art by providing an effective delivery system for specifically targeting therapeutic agents to the cytosol of key target cells while minimizing any off target effects. The system involves a bifunctional conjugate of antigen binding compound and a protein translocase. The conjugate is effectively delivered to target cells expressing the antigen on the cell surface. When the target cell expresses a specific protease that can cleave and activate the protein translocase, a pre-pore is generated on the surface of the cell. A therapeutic cargo molecule, linked either to the protein translocase or to a corollary effector protein such as lethal factor (LF) associates with the pre-pore and is delivered to the endosome of the cell. When the pre-pore becomes a pore in the endosome, the cargo is delivered to the cytosol. The dual specificity (cell surface antigen expression and protease activity) achieved by the conjugates described herein provides significant target specificity.

Figures 1A, 1B:
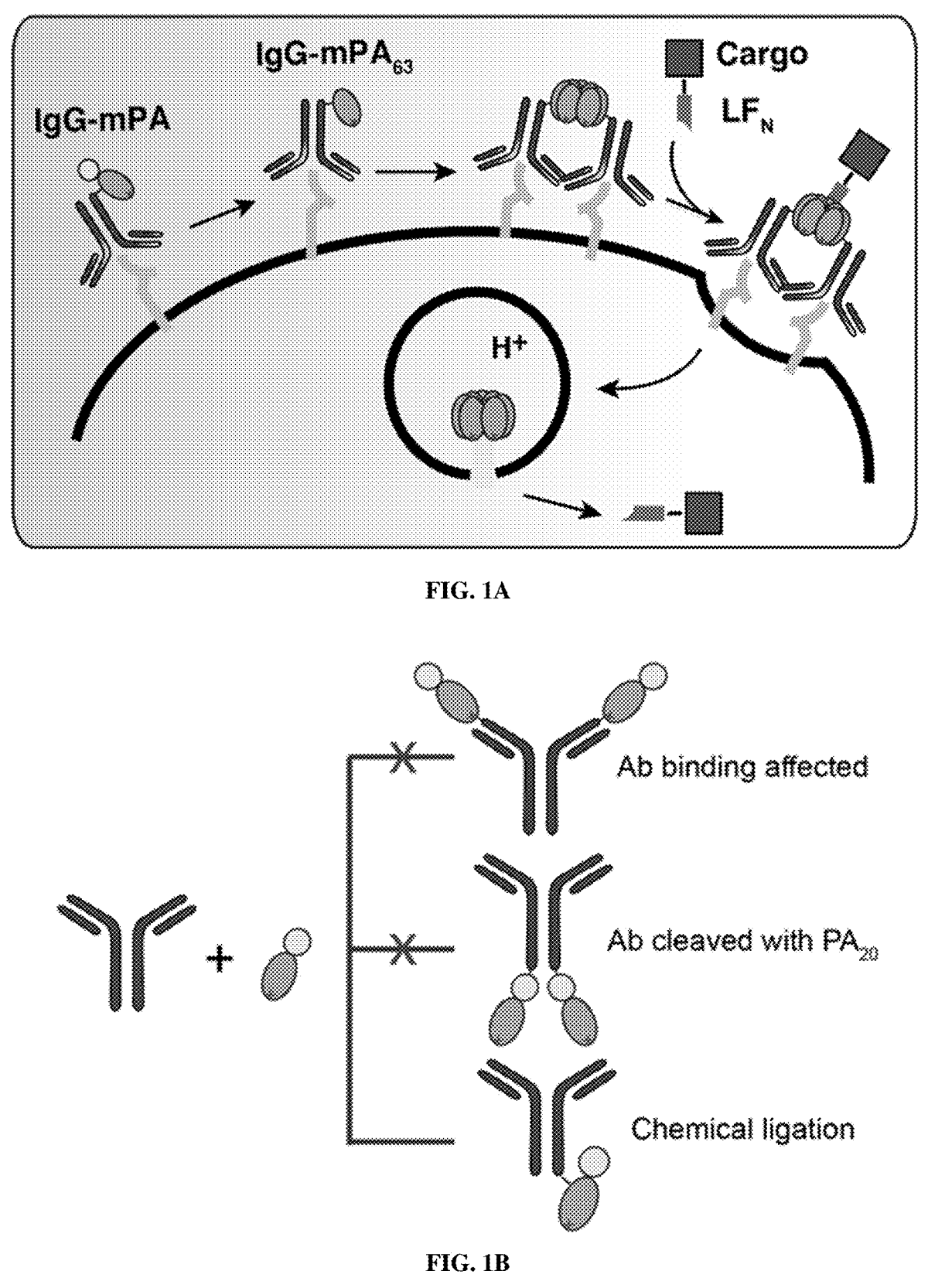

The system is demonstrated with examples using the protein translocase (PA) of anthrax. Some of the description herein refers to the use of PA for exemplary purposes. However, the invention is not limited to PA. The conjugates described herein can be prepared by chemically conjugating the protein translocase PA to antibodies (e.g., IgG molecules) using a strategy such as that diagrammed in FIG. 1A. Antibody-PA conjugates (IgG PA conjugates) that are able to orthogonally target a specific antigen and protease on a given cell surface simultaneously were shown (see Examples) to efficiently deliver a cargo molecule both in vitro and in vivo. In particular, it was demonstrated that the delivery vehicle is entirely antibody-guided and requires the function of the translocase for activity. The method was used to deliver a variety of different cargo molecules, including ribosyltransferase DTA, adenylate cyclase EF, and Ras protease RRSP.

The system described herein can be used, for example, to target cancer cells for delivery. Typically, the desired payload (e.g., cargo molecule) will be cytotoxic. Immunotoxins, for example, are protein toxins engineered to target cancer cells through ligands or antibodies. However, they are often associated with dose-limiting toxicities due to off-target damage to other tissues and cells. This is because most of the tumor cell surface antigens or receptors are also present on normal cells and even a small amount of such toxins can cause serious harm due to their catalytic nature. In contrast, the instant delivery system uses the protease-gated activation of PA and the fact that most aggressive tumors require particular proteases such as uPA and MMPs for the dissolution of extracellular matrix, which is a prerequisite for tumor invasion and metastasis. By replacing furin-dependent mPA with uPA- or MMP-dependent mPA variants in the IgG-mPA conjugate, a highly specific delivery system that requires the simultaneous presence of IgG-specific antigen and mPA-specific protease for activation, is formed. When a highly potent toxin was used as the cargo, the dual-targeted system displayed significantly improved selectivity compared to previous studies both in vitro and in vivo. Moreover, combinations of IgGs and mPA variants can be synthesized efficiently due to the modular design of the conjugation strategy, which makes the process highly reproducible among different IgGs and mPAs. With an enormous selection of monoclonal antibodies and many cell surface proteases expressed by human cells and pathogens, it is thought that the modulary delivery system can be tailored for a variety of diseases.

The delivery system described herein comprises antibody linked to a bacterial effector translocase protein. The bacterial effector translocase protein, as used herein, is a protein that, when cleaved by proteases, is activated to oligomerize and form a pre-pore. The pre-pore forms a pore in the endosome. Bacterial effector translocase proteins include but are not limited to translocation domain (T domain) of diphtheria toxin, *Vibrio cholerae*, aerolysin, alpha-toxin, protective antigen (PA), perfringolysin O, listeriolysin O, intermedilysin, colicin A, and HlyA.

The bacterial effector translocase protein has an N-terminus, a C-terminus and a plurality of internal amino acids. An important component of aspects of the invention involves the linking of the antibody to a side chain of the bacterial effector translocase protein. It was demonstrated herein that linking the antibody to the N- or C-terminal end of the bacterial effector translocase protein disrupted the activity and resulted in a non-functional conjugate. Thus, the antibody is linked to the bacterial effector translocase protein via a side chain stemming from an internal amino acid. This may be accomplished using a chemical reaction, such as, for instance, a sortase-mediated ligation. In some embodiments, the sortase-mediated ligation occurs between C-terminus of a heavy chain of the antibody and a linker which is attached to an internal amino acid of the bacterial effector translocase protein.

In some embodiments, the first internal amino acid conjugated to the linker is positioned at least 10 amino acids away from the N-terminus of the bacterial effector translocase protein. In another embodiment, the first internal amino acid conjugated to the linker is positioned at least 200 amino acids away from the N-terminus of the bacterial effector translocase protein. In still other embodiments, the first internal amino acid conjugated to the linker is positioned at least 10, 15, 20, 35, 30, 35, 40, 45, 50, 60, 70, 80, 90, 100, 110, 120, 130, 140, 150, 160, 170, 180, 190, 200, 220, 240, 260, 280, 300, 325, 350, 375, 400, 425, 450, 475, 500, 525, 550, 575, 600, 625, 650, 675, 700, or more amino acids away from the N-terminus of the bacterial effector translocase protein. In some embodiments, the first internal amino acid conjugated to the linker is positioned at least 10 amino acids away from the C-terminus of the bacterial effector translocase protein. For example, the first internal amino acid conjugated to the linker is positioned at least 10, 15, 20, 35, 30, 35, 40, 45, 50, 60, 70, 80, 90, 100, 110, 120, 130, 140, 150, 160, 170, 180, 190, 200, 220, 240, 260, 280, 300 or more amino acids away from the N-terminus of the bacterial effector translocase protein.

The bacterial effector translocase protein (e.g., protective antigen), in some embodiments, comprises a protein translocase. Protein translocases are capable of forming a transmembrane pore. In some embodiments, the translocase is derived from the toxin of a pathogenic bacterium, such as *Bacillis anthracis, Escherichia coli, Corynebacterium diph-*

*theriae, Staphylococcus aureus, Vibrio cholerae, Aeromonas hydrophila, Clostridium septicum, Clostridium perfringens, Listeria monocytogenes*, and *Staphylococcus intermedius*.

In some embodiments, the protective antigen is wild-type bacterial effector translocase protein. In other embodiments, the bacterial effector translocase protein comprises one or more mutation relative to the wild-type sequence. Examples of mutations include insertions, deletions, and amino acid residue substitutions. An example of an amino acid residue substitution is a lysine to cysteine substitution at position 563 of protective antigen, shown in SEQ ID NOs: 3 and 4, below. In some embodiments, the bacterial effector translocase protein is at least 80%, 85%, 90%, 91%, 92%, 93%, 94%, 95%, 96%, 97%, 98%, or 99% identical to the wild-type bacterial effector translocase protein. Exemplary mutated PA sequences are provided below (mutations are underlined and bolded; the furin cleavage site, RKKR (SEQ ID NO: 13), is bolded and italicized).

```
Wild-type PA (from anthrax lethal toxin)
                                                         (SEQ ID NO: 1)
MEVKQENRLLNESESSSQGLLGYYFSDLNFQAPMVVTSSTTGDLSIPSSELENIPSENQYFQSA

IWSGFIKVKKSDEYTFATSADNHVTMWVDDQEVINKASNSNKIRLEKGRLYQIKIQYQRENPTE

KGLDFKLYWTDSQNKKEVISSDNLQLPELKQKSSNSRKKRSTSAGPTVPDRDNDGIPDSLEVEG

YTVDVKNKRTFLSPWISNIHEKKGLTKYKSSPEKWSTASDPYSDFEKVTGRIDKNVSPEARHPL

VAAYPIVHVDMENIILSKNEDQSTQNTDSETRTISKNTSTSRTHTSEVHGNAEVHASFFDIGGS

VSAGFSNSNSSTVAIDHSLSLAGERTWAETMGLNTADTARLNANIRYVNTGTAPIYNVLPTTSL

VLGKNQTLATIKAKENQLSQILAPNNYYPSKNLAPIALNAQDDFSSTPITMNYNQFLELEKTKQ

LRLDTDQVYGNIATYNFENGRVRVDTGSNWSEVLPQIQETTARIIFNGKDLNLVERRIAAVNPS

DPLETTKPDMTLKEALKIAFGFNEPNGNLQYQGKDITEFDFNEDQQTSQNIKNQLAELNATNIY

TVLDKIKLNAKMNILIRDKRFHYDRNNIAVGADESVVKEAHREVINSSTEGLLLNIDKDIRKIL

SGYIVEIEDTEGLKEVINDRYDMLNISSLRQDGKTFIDFKKYNDKLPLYISNPNYKVNVYAVTK

ENTIINPSENGDTSTNGIKKILIFSKKGYEIG

PA[N682A, D683A]
                                                         (SEQ ID NO: 2)
MEVKQENRLLNESESSSQGLLGYYFSDLNFQAPMVVTSSTTGDLSIPSSELENIPSENQYFQSA

IWSGFIKVKKSDEYTFATSADNHVTMWVDDQEVINKASNSNKIRLEKGRLYQIKIQYQRENPTE

KGLDFKLYWTDSQNKKEVISSDNLQLPELKQKSSNSRKKRSTSAGPTVPDRDNDGIPDSLEVEG

YTVDVKNKRTFLSPWISNIHEKKGLTKYKSSPEKWSTASDPYSDFEKVTGRIDKNVSPEARHPL

VAAYPIVHVDMENIILSKNEDQSTQNTDSETRTISKNTSTSRTHTSEVHGNAEVHASFFDIGGS

VSAGFSNSNSSTVAIDHSLSLAGERTWAETMGLNTADTARLNANIRYVNTGTAPIYNVLPTTSL

VLGKNQTLATIKAKENQLSQILAPNNYYPSKNLAPIALNAQDDFSSTPITMNYNQFLELEKTKQ

LRLDTDQVYGNIATYNFENGRVRVDTGSNWSEVLPQIQETTARIIFNGKDLNLVERRIAAVNPS

DPLETTKPDMTLKEALKIAFGFNEPNGNLQYQGKDITEFDFNFDQQTSQNIKNQLAELNATNIY

TVLDKIKLNAKMNILIRDKRFHYDRNNIAVGADESVVKEAHREVINSSTEGLLLNIDKDIRKIL

SGYIVEIEDTEGLKEVINDRYDMLNISSLRQDGKTFIDFKKYAAKLPLYISNPNYKVNVYAVTK

ENTIINPSENGDTSTNGIKKILIFSKKGYEIG

PA[N682A, D683A, K563C] (mPAC)
                                                         (SEQ ID NO: 3)
MEVKQENRLLNESESSSQGLLGYYFSDLNFQAPMVVTSSTTGDLSIPSSELENIPSENQYFQSA

IWSGFIKVKKSDEYTFATSADNHVTMWVDDQEVINKASNSNKIRLEKGRLYQIKIQYQRENPTE

KGLDFKLYWTDSQNKKEVISSDNLQLPELKQKSSNSRKKRSTSAGPTVPDRDNDGIPDSLEVEG

YTVDVKNKRTFLSPWISNIHEKKGLTKYKSSPEKWSTASDPYSDFEKVTGRIDKNVSPEARHPL

VAAYPIVHVDMENIILSKNEDQSTQNTDSETRTISKNTSTSRTHTSEVHGNAEVHASFFDIGGS

VSAGFSNSNSSTVAIDHSLSLAGERTWAETMGLNTADTARLNANIRYVNTGTAPIYNVLPTTSL

VLGKNQTLATIKAKENQLSQILAPNNYYPSKNLAPIALNAQDDFSSTPITMNYNQFLELEKTKQ

LRLDTDQVYGNIATYNFENGRVRVDTGSNWSEVLPQIQETTARIIFNGKDLNLVERRIAAVNPS
```

-continued

```
DPLETTKPDMTLKEALKIAFGFNEPNGNLQYQGKDITEFDFNFDQQTSQNICNQLAELNATNIY

TVLDKIKLNAKMNILIRDKRFHYDRNNIAVGADESVVKEAHREVINSSTEGLLLNIDKDIRKIL

SGYIVEIEDTEGLKEVINDRYDMLNISSLRQDGKTFIDFKKYAAKLPLYISNPNYKVNVYAVTK

ENTIINPSENGDTSTNGIKKILIFSKKGYEIG

PA[N682A, D683A, K563C, F427A] (mPACA)
                                                        (SEQ ID NO: 4)
MEVKQENRLLNESESSSQGLLGYYFSDLNFQAPMVVTSSTTGDLSIPSSELENIPSENQYFQSA

IWSGFIKVKKSDEYTFATSADNHVTMWVDDQEVINKASNSNKIRLEKGRLYQIKIQYQRENPTE

KGLDFKLYWTDSQNKKEVISSDNLQLPELKQKSSNSRKKRSTSAGPTVPDRDNDGIPDSLEVEG

YTVDVKNKRTFLSPWISNIHEKKGLTKYKSSPEKWSTASDPYSDFEKVTGRIDKNVSPEARHPL

VAAYPIVHVDMENIILSKNEDQSTQNTDSETRTISKNTSTSRTHTSEVHGNAEVHASFFDIGGS

VSAGFSNSNSSTVAIDHSLSLAGERTWAETMGLNTADTARLNANIRYVNTGTAPIYNVLPTTSL

VLGKNQTLATIKAKENQLSQILAPNNYYPSKNLAPIALNAQDDASSTPITMNYNQFLELEKTKQ

LRLDTDQVYGNIATYNFENGRVRVDTGSNWSEVLPQIQETTARIIFNGKDLNLVERRIAAVNPS

DPLETTKPDMTLKEALKIAFGFNEPNGNLQYQGKDITEFDFNFDQQTSQNICNQLAELNATNIY

TVLDKIKLNAKMNILIRDKRFHYDRNNIAVGADESVVKEAHREVINSSTEGLLLNIDKDIRKIL

SGYIVEIEDTEGLKEVINDRYDMLNISSLRQDGKTFIDFKKYAAKLPLYISNPNYKVNVYAVTK

ENTIINPSENGDTSTNGIKKILIFSKKGYEIG
```

The bacterial effector translocase protein (e.g., protective antigen) is conjugated to an antibody. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact ((e.g., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, and any other modified configuration of the immunoglobulin molecule that comprises an antigen recognition site of the required specificity, including glycosylation variants of antibodies, amino acid sequence variants of antibodies, and covalently modified antibodies.

An antibody includes an antibody of any class, such as IgD, IgE, IgG, IgA, or IgM (or sub-class thereof), and the antibody need not be of any particular class. In some embodiments, the antibody of the antibody-protective antigen conjugate is an IgG antibody. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: F Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules known as single chain Fv (scFv). See e.g., Bird et al. (1988) Science 242:423-426; and Huston et al. (1988) Proc. Natl. Acad. Sci. USA 85:5879-5883.

In some embodiments, the antibody is an IgG antibody that binds to a target cell (e.g., a cancer cell). Antibodies directed to cell surface antigens are available commercially, from numerous sources including companies such as Abcam, AbD Serotec, Abnova, Thermo Scientific, Pierce Antibodies, Advanced Targeting Systems, Novus Bio, BD Pharmingen and many others. The commercial antibodies may be used as is or modified or humanized by methods well known to the skilled artisan. Exemplary antibodies include Trastuzumab and Cetuxiumab. The two humanized recombinant monoclonal antibodies bind to HER2 and EGFR, respectively. EGFR, epidermal growth factor receptor, and HER2 are cell surface receptor tyrosine kinases and are implicated in numerous human cancers. Their respective heavy chain (HC) and light chain (LC) sequences are given below.

```
Trastuzumab-LC
                                          (SEQ ID NO: 5)
ADIQMTQSPSSLSASVGDRVTITCRASQDVNTAVAWYQQKPGKAPKLLIY

SASFLYSGVPSRFSGSRSGTDFTLTISSLQPEDFATYYCQQHYTTPPTFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC

Trastuzumab-HC
                                          (SEQ ID NO: 6)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK

Cetuximab-LC
                                          (SEQ ID NO: 7)
DILLTQSPVILSVSPGERVSFSCRASQSIGTNIHWYQQRTNGSPRLLIKY

ASESISGIPSRFSGSGSGTDFTLSINSVESEDIADYYCQQNNNWPTTFGA

GTKLELKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Cetuximab-HC
                                          (SEQ ID NO: 8)
QVQLKQSGPGLVQPSQSLSITCTVSGFSLTNYGVHWVRQSPGKGLEWLGV IWSGGNTDYNTPFTSRLSINKDNSKSQVFFKMNSLQSNDTAIYYCARALT
                                           -continued
YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGK
```

Other examples of cell surface targets include, but are not limited to, tumor necrosis factor receptor (TNFR), cytotoxic T lymphocyte antigen 4 (CTLA4), programmed cell death protein 1 (PD1), B- and T lymphocyte attenuator (BTLA), lymphocyte activation gene 3 (LAG3), CD160, PD1 homolog (PD1H), CD28, inducible co-stimulator (ICOS), CD137 (also known as 4-1BB), CD27, OX40, glucocorticoid-induced TNFR-related protein (GITR), CD40 ligand (CD40L), B cell activation factor receptor (BAFFR), transmembrane activator, CAML interactor (TACI), B cell maturation antigen (BCMA), B7 ligand members, APRIL, a proliferation-inducing ligand; B7H1, B7 homolog 1; GITRL, GITR ligand; HVEM, herpesvirus entry mediator; ITAM, immunoreceptor tyrosine-based activation motif; ITIM, immunoreceptor tyrosine-based inhibitory motif; ITSM, immunoreceptor tyrosine-based switch motif; MHC, major histocompatibility complex; OX40L, OX40 ligand; PI3K, phosphoinositide 3-kinase; TCR, T cell receptor; TRAF, and TNFR-associated factor binding peptide.

In some embodiments, the antibody and the protective antigen are linked to one another via any method known in the art, including chemical conjugation and through use of a linker. Chemical conjugation may be accomplished, for example through the use of a transpeptidase, such as DD-transpeptidase, peptidyl transferase, gamma-glutamyl transpeptidase, D-glutamyl transpeptidase, or a sortase.

Sortases have been classified into 4 classes, designated A, B, C, and D, based on sequence alignment and phylogenetic analysis of 61 sortases from Gram positive bacterial genomes. The term "sortase A" is used herein to refer to a class A sortase, usually named SrtA in any particular bacterial species, e.g., SrtA from S. aureus. Likewise "sortase B" is used herein to refer to a class B sortase, usually named SrtB in any particular bacterial species, e.g., SrtB from S. aureus. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

In some embodiments, the sortase is a sortase A (SrtA). SrtA recognizes the motif LPXTG (SEQ ID NO: 14), with common recognition motifs being, e.g., LPKTG (SEQ ID NO: 15), LPATG (SEQ ID NO: 16), LPNTG (SEQ ID NO: 17). In some embodiments LPETG (SEQ ID NO: 18) is used. However, motifs falling outside this consensus may also be recognized. For example, in some embodiments the motif comprises an 'A' rather than a 'T' at position 4, e.g., LPXAG (SEQ ID NO: 19), e.g., LPNAG (SEQ ID NO: 20). In some embodiments the motif comprises an 'A' rather than a 'G' at position 5, e.g., LPXTA (SEQ ID NO: 21), e.g., LPNTA (SEQ ID NO: 22). In some embodiments the motif comprises a 'G' rather than 'P' at position 2, e.g., LGXTG (SEQ ID NO: 23), e.g., LGATG (SEQ ID NO: 24). In some embodiments the motif comprises an 'I' rather than 'L' at position 1, e.g., IPXTG (SEQ ID NO: 25), e.g., IPNTG (SEQ ID NO: 26) or IPETG (SEQ ID NO: 27).

The terms "recognition motif" and "recognition sequence", with respect to sequences recognized by a sortase, are used interchangably.

The invention contemplates use of sortases found in any gram positive organism, such as those mentioned herein and/or in the references (including databases) cited herein. The invention also contemplates use of sortases found in gram negative bacteria, e.g., *Colwellia psychrerythraea, Microbulbifer degradans, Bradyrhizobium japonicum, Shewanella oneidensis*, and *Shewanella putrefaciens*. They recognize sequence motifs LP[Q/K]T[A/S]T (SEQ ID NO: 28). In keeping with the variation tolerated at position 3 in sortases from gram positive organisms, a sequence motif LPXT[A/S] (SEQ ID NO: 29), e.g., LPXTA (SEQ ID NO: 21) or LPSTS (SEQ ID NO: 30) may be used.

The invention contemplates use of sortase recognition sequences (motifs) from any of the experimentally verified or putative sortase substrates listed at bamics3.cmbi.kun.nl/jos/sortase_substrates/help, the contents of which are incorporated herein by reference. In some embodiments the sortase recognition motif is selected from: LPKTG (SEQ ID NO: 15), LPITG (SEQ ID NO: 31), LPDTA (SEQ ID NO: 32), SPKTG (SEQ ID NO: 33), LAETG (SEQ ID NO: 34), LAATG (SEQ ID NO: 35), LAHTG (SEQ ID NO: 36), LASTG (SEQ ID NO: 37), LPLTG (SEQ ID NO: 38), LSRTG (SEQ ID NO: 39), LPETG (SEQ ID NO: 18), VPDTG (SEQ ID NO: 40), IPQTG (SEQ ID NO: 41), YPRRG (SEQ ID NO: 42), LPMTG (SEQ ID NO: 43), LAFTG (SEQ ID NO: 44), LPQTS (SEQ ID NO: 45), it being understood that in various embodiments of the invention the 5th residue is replaced, as described elsewhere herein. For example, the sequence used may be LPXT, LAXT, LPXA, LGXT, IPXT, NPXT, NPQS (SEQ ID NO: 46), LPST (SEQ ID NO: 47), NSKT (SEQ ID NO: 48), NPQT (SEQ ID NO: 49), NAKT (SEQ ID NO: 50), LPIT (SEQ ID NO: 51), or LAET (SEQ ID NO: 52). The invention comprises embodiments in which 'X' in any sortase recognition motif disclosed herein or known in the art is any standard or non-standard amino acid. Each variation is disclosed. In some embodiments, X is selected from the 20 standard amino acids found most commonly in proteins found in living organisms. In some embodiments, e.g., where the recognition motif is LPXTG (SEQ ID NO: 53) or LPXT (SEQ ID NO: 54), X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG (SEQ ID NO: 55) or LPXT (SEQ ID NO: 56) motif where the sortase is a sortase A. In some embodiments X is selected from K, S, E, L, A, N in an LPXTG (SEQ ID NO: 57) or LPXT (SEQ ID NO: 58) motif and a class C sortase is used.

In some embodiments, a recognition sequence further comprises one or more additional amino acids, e.g., at the N or C terminus. For example, one or more amino acids (e.g., up to 5 amino acids) having the identity of amino acids found immediately N-terminal to, or C-terminal to, a 5 amino acid recognition sequence in a naturally occurring sortase substrate may be incorporated. Such additional amino acids may provide context that improves the recognition of the recognition motif.

In some embodiments, a recognition motif (e.g., LPXTG (SEQ ID NO: 14)), is added to the protein of interest (e.g., an antibody), while an oligo-glycine motif is added to the N-terminus of a second protein of interest (e.g., $G_3$-mPA). The sortase is added, resulting in the covalent linkage of the two proteins through a peptide bond. In some embodiments, the sortase is mutated, for example triple mutant sortase (SrtA*). An example of the chemical conjugation described herein is provided in Example 1 below.

In some embodiments, the C-terminus of the heavy chains or the C-terminus of the light chains of the antibody are linked to the bacterial effector translocase protein. In a particular embodiment, the C-terminal of the heavy chain of the antibody is linked to the bacterial effector translocase protein (e.g., protective antigen). In one embodiment, the recognition motif is LPSTGG (SEQ ID NO: 59). The protective antigen may comprise a mutation, for example, a cysteine substitution, as described above. In some embodiments, the cysteine substitution occurs at about the center of the protective antigen, for example, at least 100, 150, 200, 250, 300, 350, 400, 450, 500, 550, or 600 amino acids from either the N-terminus or the C-terminus, or both. In one embodiment the mutation is 563 amino acids from the N-terminus and 171 amino acids from the C terminus.

Anticancer antibodies have been described in the art, see e.g., Ross et al., Am J Clin Pathol 2003; 119:472-485; Scott et al., and Cancer Immunity (1 May 2012) Vol. 12, p. 14. Non-limiting Examples of anti-cancer antibodies include alemtuzumab (Campath®), trastuzumab (Herceptin®), Ibritumomab tiuxetan (Zevalin®), blinatumomab (Blincyto®), Gemtuzumab (Mylotarg®), Ibritumomab (Zevalin®), Edrecolomab (Panorex®), Daclizumab (Zenapax®), Rituximab (Rituxan®), Tositumomab (Bexxar®), Epratuzumab (LymphoCide®), Bevacizumab (Avastin®), Lintuzumab (Zamyl®), Apolizumab, Labetuzumab, Oregovomab, Visilizumab, nivolumab (Opdivo®), pembrolizumab (Keytruda®), avelumab (Bavencio®), durvalumab (Imfinzi®), cemiplimab (Libtayo®), atezolizumab (Tecentriq®), Panitunuman (Vectibix®), Ipilimubam (Yervoy®), Ofatumumab (Arzerra®), and Gemtuzumab.

The sequences of two exemplary antibodies are provided below. In each antibody, the LPSTG motif has been inserted at the C-terminal of the heavy chain, so that the antibody can be fused to the protective antigen, for example, using a sortase. The insertion is shown in bold and underlined.

```
Trastuzumab-HC-LPSTGG
                                  (SEQ ID NO: 9)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPLP

STGGK
```

Cetuximab-HC-LPSTGG
(SEQ ID NO: 10)
QVQLKQSGPGLVQPSQSLSITCTVSGFSLTNYGVHWVRQSPGKGLEWLGV

IWSGGNTDYNTPFTSRLSINKDNSKSQVFFKMNSLQSNDTAIYYCARALT

YYDYEFAYWGQGTLVTVSAASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTHTCPPCPAPELLGGPSVFLEPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPLPS

TGGK

In protective antigen-mediated translocation, PA only oligomerizes following cleavage by furin-family proteases after the sequence RKKR (SEQ ID NO: 13). In some embodiments, furin-proteases are used; however, in other embodiments, the PA sequence is modified so that furin-proteases are unable to cleave the mutant PA. For example, PA mutants can be synthesized to express cleavage sites susceptible to other proteases, such as matrix metalloproteinase (MMP) or urokinase-type plasminogen activator (uPA). This specificity can allow for orthogonal targeting of specific receptors and proteases, leading to greater specificity in the delivery system. Examples of two such PA mutants are shown below (the protease cleavage site is bolded and underlined).

mPAC-uPA
(SEQ ID NO: 11)
MEVKQENRLLNESESSSQGLLGYYFSDLNFQAPMVVTSSTTGDLSIPSSE

LENIPSENQYFQSAIWSGFIKVKKSDEYTFATSADNHVTMWVDDQEVINK

ASNSNKIRLEKGRLYQIKIQYQRENPTEKGLDFKLYWTDSQNKKEVISSD

NLQLPELKQKSSNSPGSGRSASTSAGPTVPDRDNDGIPDSLEVEGYTVDV

KNKRTFLSPWISNIHEKKGLTKYKSSPEKWSTASDPYSDFEKVTGRIDKN

VSPEARHPLVAAYPIVHVDMENIILSKNEDQSTQNTDSETRTISKNTSTS

RTHTSEVHGNAEVHASFFDIGGSVSAGFSNSNSSTVAIDHSLSLAGERTW

AETMGLNTADTARLNANIRYVNTGTAPIYNVLPTTSLVLGKNQTLATIKA

KENQLSQILAPNNYYPSKNLAPIALNAQDDFSSTPITMNYNQFLELEKTK

QLRLDTDQVYGNIATYNFENGRVRVDTGSNWSEVLPQIQETTARTIFNGK

DLNLVERRIAAVNPSDPLETTKPDMTLKEALKIAFGFNEPNGNLQYQGKD

ITEEDFNEDQQTSQNICNQLAELNATNIYTVLDKIKLNAKMNILIRDKRF

HYDRNNIAVGADESVVKEAHREVINSSTEGLLLNIDKDIRKILSGYIVEI

EDTEGLKEVINDRYDMLNISSLRQDGKTFIDFKKYAAKLPLYISNPNYKV

NVYAVTKENTIINPSENGDTSTNGIKKILIFSKKGYEIG mPAC-MMP (SEQ ID NO: 12)
MEVKQENRLLNESESSSQGLLGYYFSDLNFQAPMVVTSSTTGDLSIPSSE

LENIPSENQYFQSAIWSGFIKVKKSDEYTFATSADNHVTMWVDDQEVINK

-continued

ASNSNKIRLEKGRLYQIKIQYQRENPTEKGLDFKLYWTDSQNKKEVISSD

NLQLPELKQKSSNSGPLGMLSQSTSAGPTVPDRDNDGIPDSLEVEGYTVD

VKNKRTFLSPWISNIHEKKGLTKYKSSPEKWSTASDPYSDFEKVTGRIDK

NVSPEARHPLVAAYPIVHVDMENIILSKNEDQSTQNTDSETRTISKNTST

SRTHTSEVHGNAEVHASFFDIGGSVSAGFSNSNSSTVAIDHSLSLAGERT

WAETMGLNTADTARLNANIRYVNTGTAPIYNVLPTTSLVLGKNQTLATIK

AKENQLSQILAPNNYYPSKNLAPIALNAQDDFSSTPITMNYNQFLELEKT

KQLRLDTDQVYGNIATYNFENGRVRVDTGSNWSEVLPQIQETTARTIFNG

KDLNLVERRIAAVNPSDPLETTKPDMTLKEALKIAFGFNEPNGNLQYQGK

DITEEDFNEDQQTSQNICNQLAELNATNIYTVLDKIKLNAKMNILIRDKR

FHYDRNNIAVGADESVVKEAHREVINSSTEGLLLNIDKDIRKILSGYIVE

IEDTEGLKEVINDRYDMLNISSLRQDGKTFIDFKKYAAKLPLYISNPNYK

VNVYAVTKENTIINPSENGDTSTNGIKKILIFSKKGYEIG

Other exemplary proteases associated with cancer cells include but are not limited to MMP-2, MMP-9, plasminogen activator, tPA, ADAM, MMP-7, ADAMS, ADAM15, Matriptase, a type II transmembrane serine protease, kallikreins such as Kallikrein 3, Kallikrein 6 and kallikrein-10 (hk-10), cathepsins, such as cathepsins B, L and D, type II integral serine proteases (dipeptidyl peptidase IV (DPP4/CD26), seprase/fibroblast activation protein alpha (FAPalpha) and related type II transmembrane prolyl serine peptidases)), and Seprase. Protease sensitive peptide sequences are known in the art, see e.g., US956073B2, WO2005023314A1, and U.S. Pat. No. 8,030,447B2, the contents relating to the specific protease sequences disclosed in each reference is incorporated herein by reference. Non-limiting examples of cancer associated protease sensitive sequence include: GPLGIAGQ (SEQ ID NO: 60), PXXHy (S/T) (SEQ ID NO: 61), TGRGPSWV (SEQ ID NO: 62), SARGPSRW (SEQ ID NO: 63), TARGPSFK (SEQ ID NO: 64), LSGRSDNH (SEQ ID NO: 65), GGWHTGRN (SEQ ID NO: 66), HTGRSGAL (SEQ ID NO: 67), PLTGRSGG (SEQ ID NO: 68), LTGRSGA (SEQ ID NO: 69), SSRGPAYL (SEQ ID NO: 70), RGPATPIM (SEQ ID NO: 71), RGPA (SEQ ID NO: 72), GLKR (SEQ ID NO: 73), IPENFFGN (SEQ ID NO: 74), BPYGLGSP (SEQ ID NO: 75), HPSAFSEA (SEQ ID NO: 76), GPQGLLGA (SEQ ID NO: 77), GPAGLSVL (SEQ ID NO: 78), GPAGINTK (SEQ ID NO: 79), DAASLLGL (SEQ ID NO: 80), RPANMTSP (SEQ ID NO: 81), PPGAYHGA (SEQ ID NO: 82), LRAYLLPA (SEQ ID NO: 83), SPYELKAL (SEQ ID NO: 84), TAAALTSC (SEQ ID NO: 85), GPEGLRVG (SEQ ID NO: 86), GHARLVHV (SEQ ID NO: 87), QPVGINTS (SEQ ID NO: 88), RRINRE (SEQ ID NO: 89), and RRIN (SEQ ID NO: 90). In some embodiments, the composition further comprises a cargo molecule (e.g., payload). The cargo molecule, in some embodiments, is conjugated to the bacterial effector translocase protein. In one embodiment, the bacterial effector translocase protein has a second internal amino acid conjugated to a linker, forming a side chain and the cargo molecule is linked to the bacterial effector translocase protein via the second side chain. In other embodiments, the cargo molecule is not conjugated to the bacterial effector translocase protein. Cargo molecules can be, for example, peptides, proteins, nucleic acids or small molecules.

"Peptide" refers to a polymer of at least two monomers, wherein the monomers are amino acids, sometimes referred to as amino acid residues, which are joined together via an amide bond. For purposes of this invention, the terms "peptide," "polypeptide," and "protein," are largely interchangeable as all three types can be used in aspects of the methods described herein. The protein may be an L-protein or a D-protein. Additionally, the reagent may be a cyclic peptide. In some embodiments the reagent is not an D-protein or a cyclic peptide.

Nucleic acids useful in the methods of the invention include, morpholinos, antisense nucleic acids, RNA interference (RNAi) and/or microRNA (miRNA) pathways including small interfering RNA (siRNA), short hairpin RNA (shRNA), double-stranded RNA (dsRNA), miRNAs, and other small interfering nucleic acid-based molecules known in the art. Other nucleic acid molecules that can be used include sense and antisense nucleic acids (single or double stranded). Antisense nucleic acids include modified or unmodified RNA, DNA, or mixed polymer nucleic acids, and primarily function by specifically binding to matching sequences resulting in modulation of peptide synthesis. Antisense nucleic acid binds to target RNA by Watson Crick base-pairing and blocks gene expression by preventing ribosomal translation of the bound sequences either by steric blocking or by activating RNase H enzyme. Antisense molecules may also alter protein synthesis by interfering with RNA processing or transport from the nucleus into the cytoplasm. In some embodiments, therapeutic compositions of the invention comprise an isolated plasmid vector (e.g., any isolated plasmid vector known in the art or disclosed herein) that expresses a small interfering nucleic acid such as an shRNA. The isolated plasmid may comprise a specific promoter operably linked to a gene encoding the small interfering nucleic acid. In some cases, the isolated plasmid vector is packaged in a virus capable of infecting the individual. Exemplary viruses include adenovirus, retrovirus, lentivirus, adeno-associated virus, and others that are known in the art and disclosed herein.

Small molecules include but are not limited to peptides, nucleic acids, polysaccharide, and low molecular weight organic compound, typically below 800 Daltons. Small molecules are capable of binding to a biopolymer such as a protein, nucleic acid or polysaccharide and altering the activity or function of the biopolymer. In some embodiments, the small molecule may further comprise a detectable label. A detectable label as used herein is a moiety, the presence of which can be ascertained directly or indirectly. In some instances, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., biotin, avidin, epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Labels include any known labels that can be used with imaging techniques, such as PET isotopes, scintigraphy, NMR, etc. Other detectable labels include radioactive isotopes such as $^{32}P$ or $^3H$, luminescent markers such as fluorochromes, optical or electron density markers, etc., or epitope tags such as the FLAG epitope or the HA epitope, biotin, avidin, and enzyme tags such as horseradish peroxidase, $\beta^*$-galactosidase, nanoparticles, etc. There are many different labels and methods of labeling known to those of ordinary skill in the art. Examples of the types of labels that can be used in the present invention include binding partners (biotin-avidin), enzymes, radioisotopes, fluorescent compounds, colloidal metals, nanoparticles, chemiluminescent compounds, and bioluminescent compounds.

In some embodiments, the cargo molecules are therapeutic molecules, including, but not limited to, compounds having antiviral, antibacterial (antibiotic), or anticancer (chemotherapeutic) activity (e.g., doxorubicin, paciltaxol, and mitomycin C). Other examples of cargo molecules include drugs or drug analogs, labeled compounds, therapeutic or inhibitory nucleic acids, halogenated compounds, protein mimics, antibody mimics, mirror image biomolecules, monobodies, and/or engineered protein scaffolds.

In some embodiments, the cargo molecules are all the same; however, in other embodiments, the cargo molecules comprise a combination of two or more different types of cargo molecules. Further examples of cargo molecules include, but are not limited to, diphtheria toxin A (DTA), β-lactamase, *Pseudomonas* exotoxin A, and Ras protease RRSP.

The delivery system may be used as part of a method to treat or prevent a disease or disorder in a subject, for example, by delivery a cargo molecule (payload) to the cytosol of a living cell. The cell may be any type of living cell. For example living cells include eukaryotic cells and prokaryotic cells. Examples of living cells include but are not limited to cells derived from humans, primates, dogs, cats, horses, cows, pigs, turkeys, goats, fish, monkeys, chickens, rats, mice, sheep, plants, bacteria, algae, and yeast. The cells may be normal cells, cancerous cells or genetically engineered cells.

As used herein, "treat a disorder" refers to a treatment after the subject has developed the disorder in order to fight the disorder (e.g., stop the progression of the cancer and/or advance the subject into remission) or prevent the disease from becoming worse.

A potential limitation with the use of bacterial-derived foreign proteins in humans is the possibility of inducing antibodies in response to repeated dosing over a short time frame in a clinical setting. However, if it is desirable to provide a patient with repeat dosages within a short time frame (i.e. less than 3 weeks) several strategies are known for avoiding toxicity issues. For instance, recent studies have found that an immunosuppressive regimen that consists of pentostatin and cyclophosphamide (PC) can prevent the immunogenic response against bacterial proteins by depleting lymphocytes, particularly B cells. In addition, it has been reported that immune tolerance to recombinant immunotoxins can be induced by co-administering them with nanoparticles containing rapamycin (SVP-R). The combination of the conjugates of the invention with these strategies may further improve its utility as a protein drug delivery platform in a broad spectrum of diseases.

In some embodiments, the subject is more susceptible to the disorder than the general population (e.g., the subject is at risk of developing the disorder). A subject at risk as used herein is a subject who has any risk of exposure to a cancer or a risk of developing cancer. A "subject" means a human or vertebrate animal including but not limited to a dog, cat, horse, cow, pig, sheep, goat, turkey, chicken, primate, e.g., monkey, and fish (aquaculture species), e.g., salmon. Thus, the invention can also be used to treat disorders in non-human subjects.

The disease or disorder may be a cancer or tumor. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. In one embodiment the cancer is hairy cell leukemia, chronic myelogenous leukemia, cutaneous T-cell leukemia, multiple myeloma, follicular lymphoma, malignant melanoma, squamous cell carcinoma, renal cell carcinoma, prostate carcinoma, bladder cell carcinoma, or colon carcinoma.

The delivery system may be formulated in a pharmaceutical composition. Pharmaceutical compositions are sterile compositions that comprise agents and may comprise delivery vehicles, nanoparticles and the like, preferably in a pharmaceutically-acceptable carrier. The term "pharmaceutically-acceptable carrier" means one or more compatible solid or liquid filler, diluents or encapsulating substances which are suitable for administration to a human or other subject contemplated by the invention. The term "carrier" denotes an organic or inorganic ingredient, natural or synthetic, with which the cells, nanoparticles and agent(s) are combined to facilitate administration. The components of the pharmaceutical compositions are commingled in a manner that precludes interaction that would substantially impair their desired pharmaceutical efficiency.

The compounds and compositions, when it is desirable to deliver them systemically, may be formulated for parenteral administration by injection, e.g., by bolus injection or continuous infusion. Formulations for injection may be presented in unit dosage form, e.g., in ampoules or in multi-dose containers. Pharmaceutical parenteral formulations include aqueous solutions of the ingredients. Aqueous injection suspensions may contain substances which increase the viscosity of the suspension, such as sodium carboxymethyl cellulose, sorbitol, or dextran. Alternatively, suspensions of ingredients may be prepared as oil-based suspensions such as are known in the art or that will be readily apparent to those of ordinary skill in the art based on this disclosure.

The compounds described herein may comprise different types of carriers depending on whether it is to be administered in solid, liquid or aerosol form, and whether it need to be sterile for such routes of administration as injection. The present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

The phrase "pharmaceutically acceptable" is employed herein to refer to those structures, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Regardless of the route of administration selected, the inventive pharmaceutical compositions are formulated into pharmaceutically-acceptable dosage forms by conventional methods known to those of skill in the art.

The compositions described herein may be given in dosages, e.g., at the maximum amount while avoiding or minimizing any potentially detrimental side effects. The compositions can be administered in effective amounts, alone or in a combinations with other compounds. For example, when treating cancer, a composition may include the delivery system and therapeutic cargo molecules described herein and a cocktail of other compounds that can be used to treat cancer. When treating conditions associated with abnormal lipid levels, a composition may include the structures described herein and other compounds that can be used to reduce lipid levels (e.g., cholesterol lowering agents).

The phrase "therapeutically effective amount" as used herein means that amount of a material or composition comprising an inventive structure which is effective for producing some desired therapeutic effect in a subject at a reasonable benefit/risk ratio applicable to any medical treatment. Accordingly, a therapeutically effective amount may, for example, prevent, minimize, or reverse disease progression associated with a disease or bodily condition. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

The effective amount of any one or more structures described herein may be from about 10 ng/kg of body weight to about 1000 mg/kg of body weight, and the frequency of administration may range from once a day to once a month.

However, other dosage amounts and frequencies also may be used as the invention is not limited in this respect. A subject may be administered one or more structure described herein in an amount effective to treat one or more diseases or bodily conditions described herein.

An effective amount may depend on the particular condition to be treated. The effective amounts will depend, of course, on factors such as the severity of the condition being treated; individual patient parameters including age, physical condition, size and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular inventive structure employed, the route of administration, the time of administration, the rate of excretion or metabolism of the particular structure being employed, the duration of the treatment, other drugs, compounds and/or materials used in combination with the particular structure employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compositions described herein employed in the pharmaceutical composition at levels lower than that required to achieve the desired therapeutic effect and then gradually increasing the dosage until the desired effect is achieved.

The invention also includes kits made up of the various components described herein assembled to accomplish the methods of the invention. A kit for instance may include one or more bacterial effector translocase proteins as well as an antibody and a sortase. A further kit may include, for example, one or more bacterial effector translocase proteins linked to antibodies, and one or more cargo molecules. The one or more cargo molecules, may optionally be linked to the bacterial effector translocase protein. The kit may further comprise assay diluents, standards, controls and/or detectable labels. The assay diluents, standards and/or controls may be optimized for a particular sample matrix. Reagents include, for instance, antibodies, nucleic acids, labeled secondary agents, or in the alternative, if the primary reagent is labeled, enzymatic or agent binding reagents which are capable of reacting with the labeled reagent. One skilled in the art will readily recognize that reagents of the present invention can be readily incorporated into one of the established kit formats which are well known in the art.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment or characterization of a cancer.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or research kits to facilitate their use in therapeutic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflect approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1: Modular Design of Antibody Protective Antigen Conjugate

The antibody-protective antigen conjugate (Ab-PA) was designed so that both the antibody and PA could carry out their functions as antigen binder and protein translocase in the conjugate, the conjugate was relatively stable in a biological environment, the conjugate was a homogeneous pure substance.

Recombinant expression is a common strategy used to create fusion proteins. Two conceivable ways could be explored for this purpose, with PA expressed either on the N-terminus or C-terminus of the heavy chain/light chain (FIG. 1B). However, significant challenges exist with both approaches. If PA is on the N-terminus of the heavy chain or light chain, there is a high probability that the binding of the antibody will be affected due to the proximity of PA to the antigen binding region. If PA is on the C-terminus, $PA_{63}$ will be cleaved off antibody upon binding to the cell surface and unable to form the pre-pore. This is because PA is only activated after its N-terminal $PA_{20}$ is proteolytically cleaved by furin-family protease to give $PA_{63}$, leading to formation of a pre-pore.

Chemical conjugation is an alternative to recombinant expression and it allows more freedom to design the conjugate. In order to preserve the functions of both proteins, the C-terminus of the heavy chain, away from the antigen binding site, was conjugated to the middle of the $PA_{63}$ domain of PA using sortase-mediated ligation. First, a PA variant on which a polyglycine linker can be installed for conjugation, was created. A single cysteine mutation was introduced at the lysine 563 position of PA(N682A, D683A), a known PA mutant with ablated native receptor-binding ability while retaining its translocase activity.

Figure 2B:
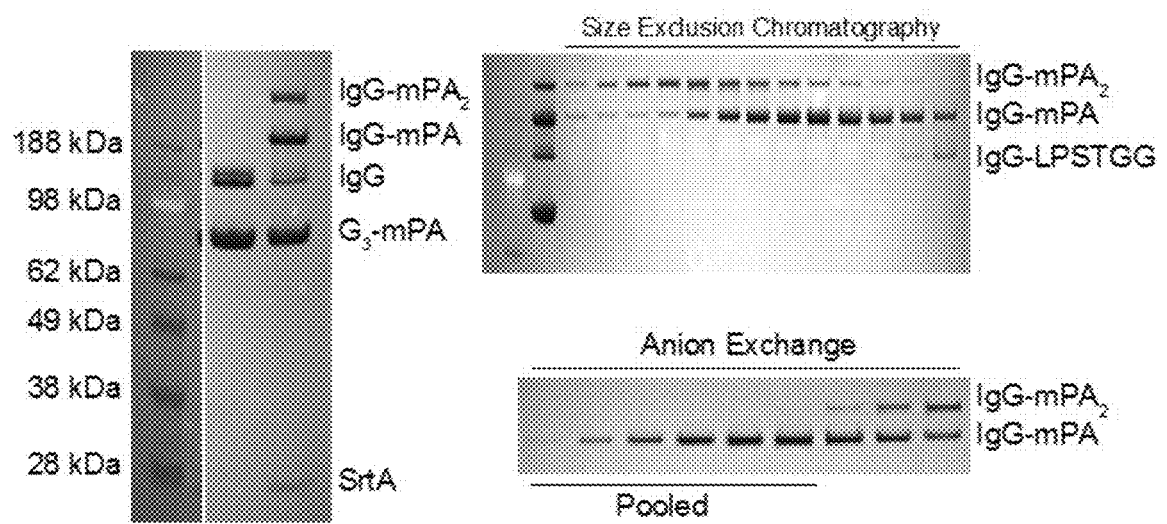

The resulting mutant protein mPAC was expressed and purified from *Escherichia coli* B121(DE3) in high yield. A short D-peptide linker with an N-terminal tri-glycine was crosslinked to the cysteine of mPAC through bromoacetamide (FIG. 2A). The resulting $G_3$-mPA was subsequently ligated by a triple mutant sortase (SrtA*) onto an IgG molecule with inserted C-terminal LPSTGG (SEQ ID NO: 59) tags at its heavy chains. This reaction gave a product mixture of both mono- and dual-mPA tagged IgGs, which was then purified to homogeneous IgG-mPA by size exclusion and anion exchange chromatography with a final yield of greater than 50% (FIG. 2B).

Figure 7:
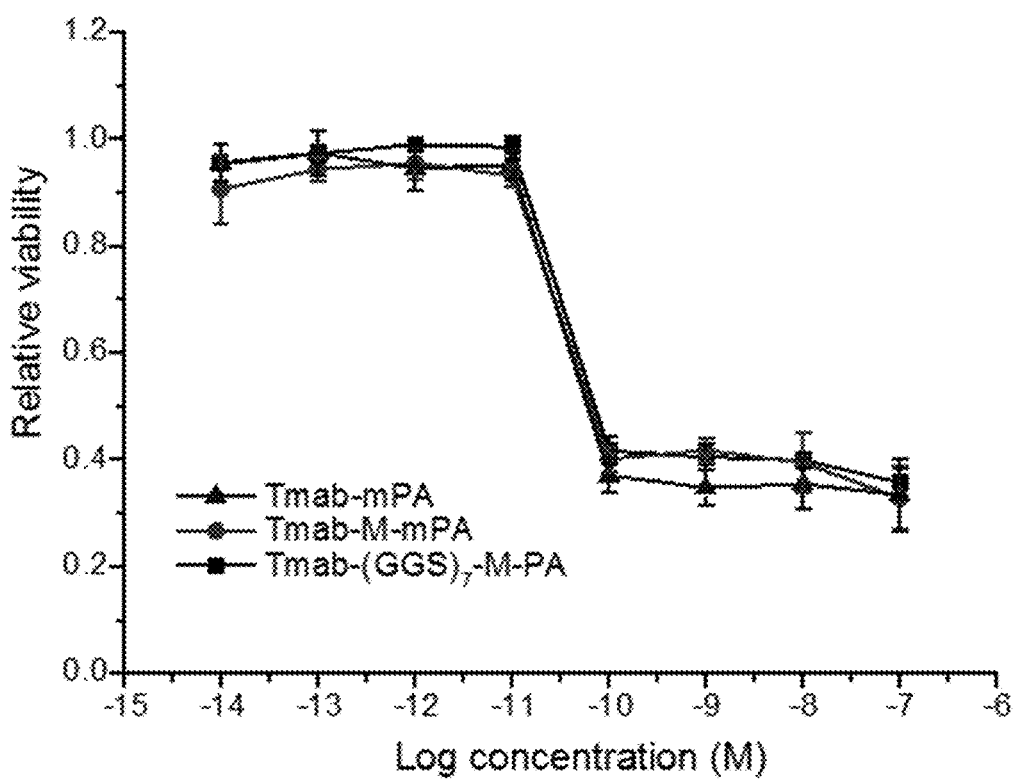
Figure 8:
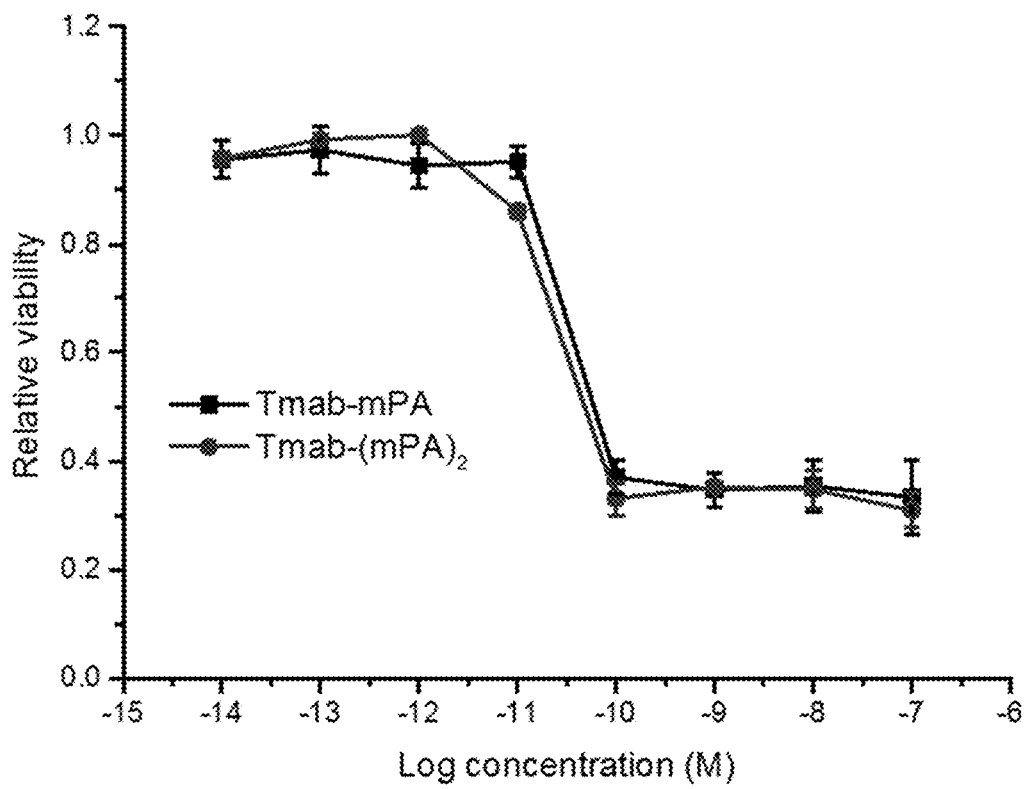
Figure 9:
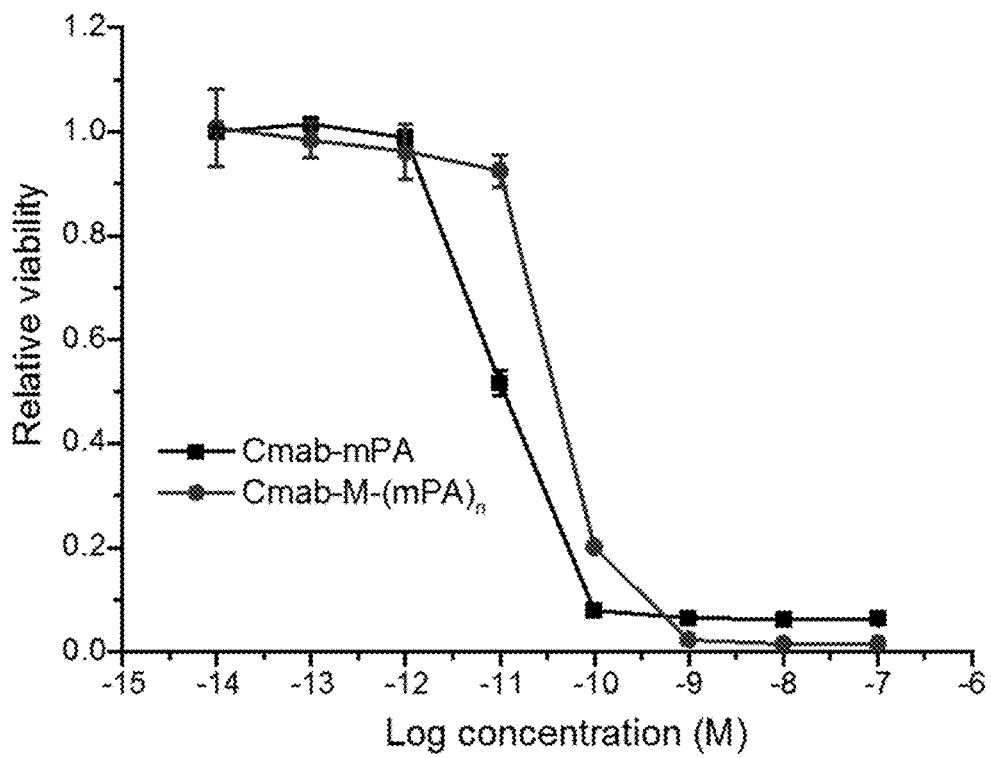

This conjugation strategy was designed to fulfill all four criteria originally sought for the system. The attachment sites on both mPA and IgG were chosen to avoid inference with their functions as antigen binder and translocase, respectively. The C-termini of the heavy chains were used for conjugation to minimize the potential impact of mPA on the IgG molecule and the cysteine was introduced in the PA63 domain so that IgG would remain attached after protease-mediated activation of mPA. An in vitro SDS-resistant pore formation assay was performed, which confirmed the activity of mPA after attachment to IgG (data not shown). Additionally, unlike ADCs or immunotoxins, of which the payloads need to be released from the antibody at the target site, the IgG-mPA needs to remain intact during its mechanism of action (e.g., pore formation) and the cargo protein comes as a separate entity. Toward this end, the short bromoacetamide D-peptide linker between IgG and mPA was designed to minimize potential cleavage in a biological environment. IgG-mPA prepared with this linker showed no appreciable degradation in 10% serum up to 7 days whereas the maleimide linked conjugate started showing cleavage after 8 hours under the same condition, consistent with previous reports. A longer poly GGS maleimide linker was also tested and exhibited similar activity to the short maleimide linker, indicating the length of the linker does not play a major role (FIG. 7). All IgG-mPA conjugates described below were prepared with the bromoacetamide D linker unless stated otherwise. Moreover, in order to obtain homogeneous IgG-mPA, the pI difference between IgG-mPA and IgG-(mPA)$_2$ was used to separate them by anion exchange. IgG-mPA was chosen for future study. IgG-(mPA)$_2$ was also found to be active (FIG. 8). It was also found that IgG-(mPA)$_n$ prepared by non-specific conjugation using a NHS-Maleimide linker was capable of delivery, despite its reduced potency (data not shown). The entire process of conjugation and purification took less than half a day and may be scaled up easily.

Figure 2C:
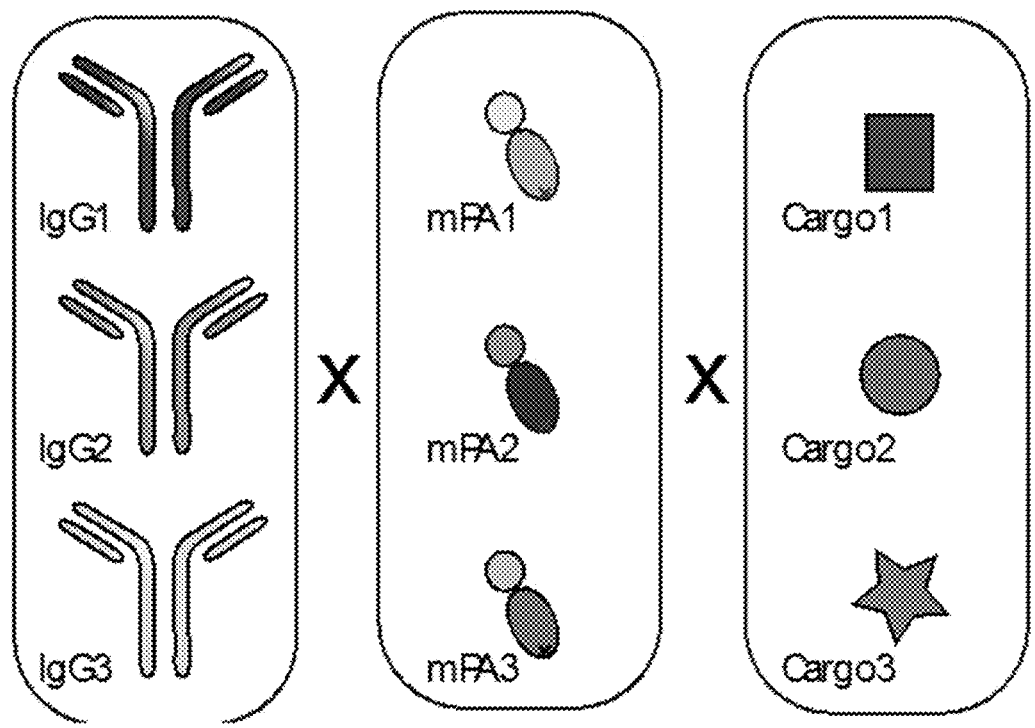
Figure 2D:
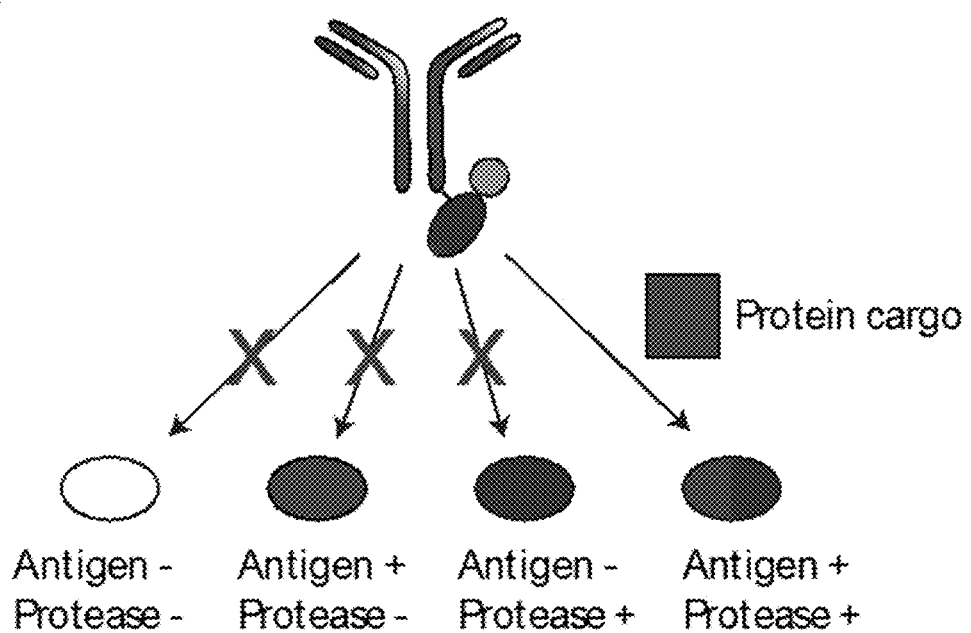

Since the cleavage site of mPA can be engineered to target different proteases, mPA variants with different protease specificities were also generated for IgG conjugation. Unlike the recombinant method, in which each protein needs to be prepared individually, the chemical conjugation strategy described above enables rapid combinations of different antibodies and mPA variants in a modular fashion (FIG. 2C). The resulting IgG-mPA variant would require the simultaneous presence of the IgG-specific antigen and the PA-specific protease for activation as demonstrated later in the results (FIG. 2D).

Example 2: Antibody-Mediated Delivery of Different Protein Cargos in Specific Cell Types Epidermal growth factor receptor (EGFR) and HER2 are among the most studied cell surface receptor tyrosine kinases. They are both implicated in tumor development and are overexpressed in a wide variety of human cancers including breast, ovarian, lung, colon, and others. The high interest in these receptors as anticancer targets has led to the development of various therapeutics from small molecule inhibitors to large antibodies. Trastuzumab (Tmab) and cetuximab (Cmab) are two humanized recombinant monoclonal antibodies that bind to HER2 and EGFR, respectively. Both antibodies have been approved by FDA years ago.

Figure 3A:
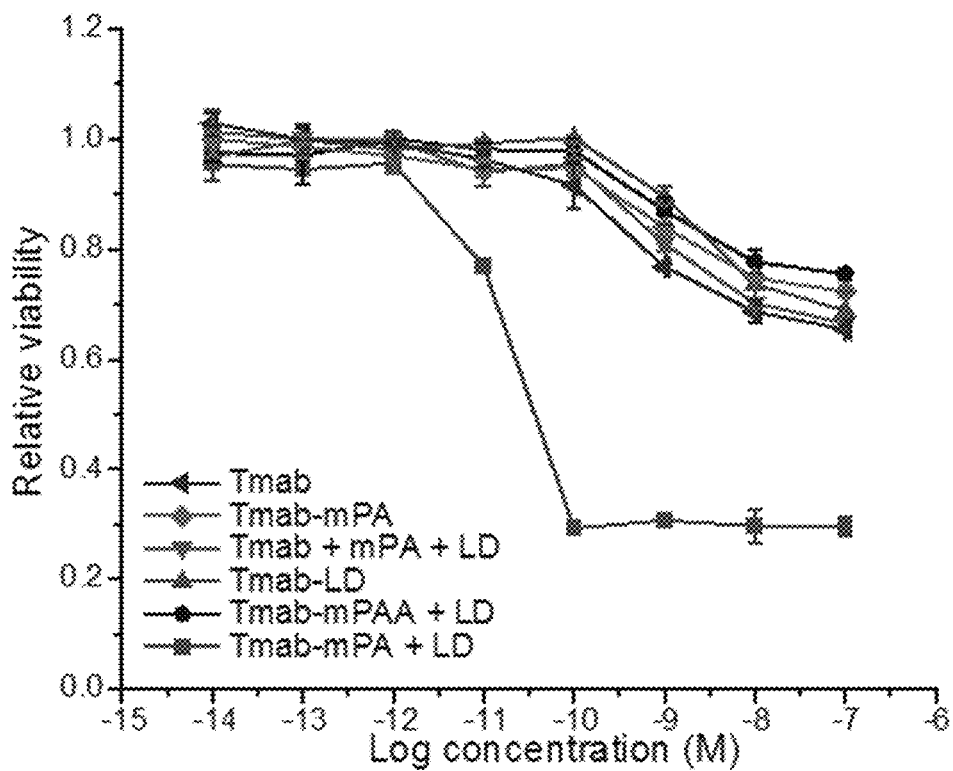

The ability of Tmab-mPA, prepared as described above, to deliver $LF_N$-DTA into HER2 positive cells was examined. $LF_N$-DTA (LD) is a fusion protein between $LF_N$, the PA prepore binding domain, and DTA, the catalytic domain of diphtheria toxin. The DTA moiety inhibits protein synthesis and causes cell death by ribosylating the eukaryotic elongation factor 2 within the cytosol. It was found that 10 nM LD in the presence of Tmab-mPA effectively reduced the viability of HER2-overexpressing BT474 cells, indicating potent cytosolic delivery of DTA, whereas LD in the presence of unconjugated Tmab/mPA only exhibited antiproliferative effects similar to those of Tmab-mPA or Tmab alone (FIG. 3A). Whether the translocase function of PA is required for the DTA delivery was examined using mPA (F427A), a mutant PA that is incapable of translocation but still binds $LF_N$. As expected, LD with Tmab-mPA(F427A) failed to show any enhanced activity. Further, when LD was directly conjugated to Tmab, the conjugate Tmab-LD also did not show any increased killing, confirming that mere endocytosis of LD is not enough to trigger DTA activity.

Figure 3B:
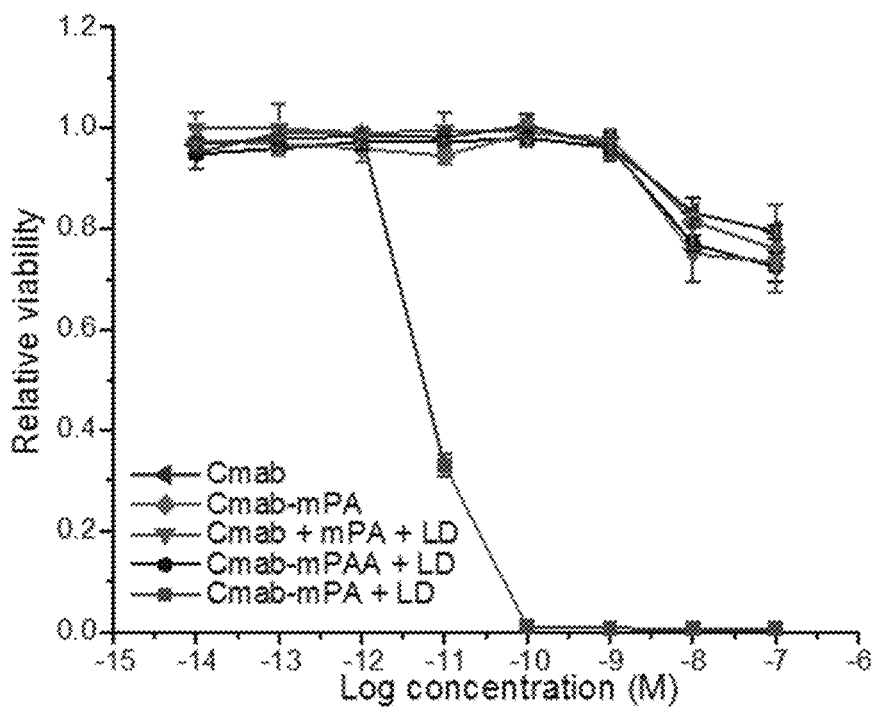

Whether the delivery strategy can be expanded to another antibody was next investigated. EGFR overexpressing A431 cells were treated with Cmab-mPA in the presence of LD under the same conditions. As in the case of Tmab-mPA, only Cmab-mPA combined with LD showed significant antiproliferative effect in A431 cells, whereas no other treatment showed any difference from the Cmab alone group, verifying that both Cmab and functional PA are both required for the cytosolic delivery of DTA (FIG. 3B). Therefore, the IgG-mPA cytosolic delivery strategy can be applied to different antibodies targeting different antigens.

Figure 3C:
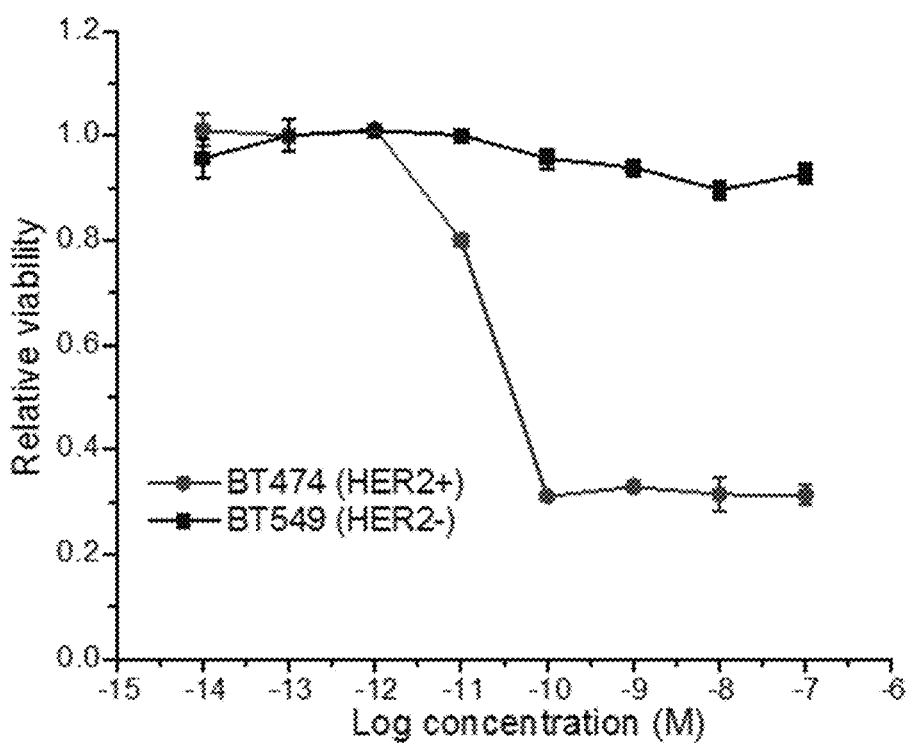
Figure 3D:
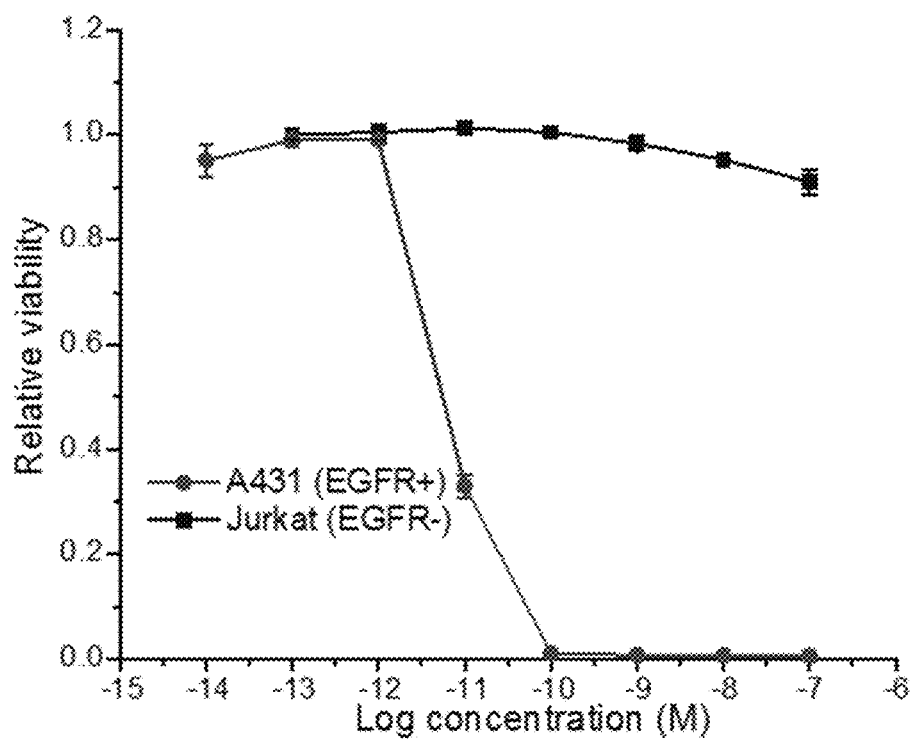
Figure 10:
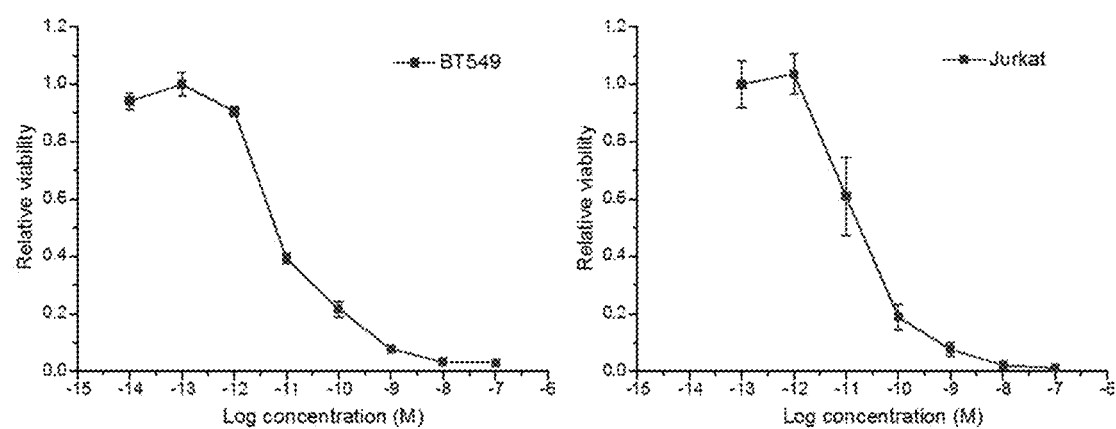
Figure 11A:
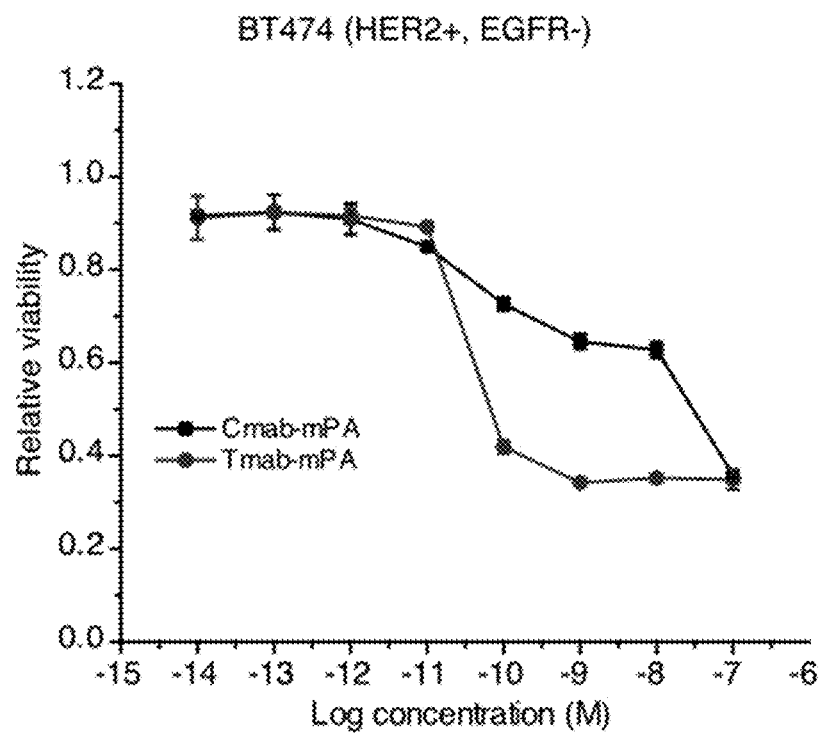
Figure 11B:
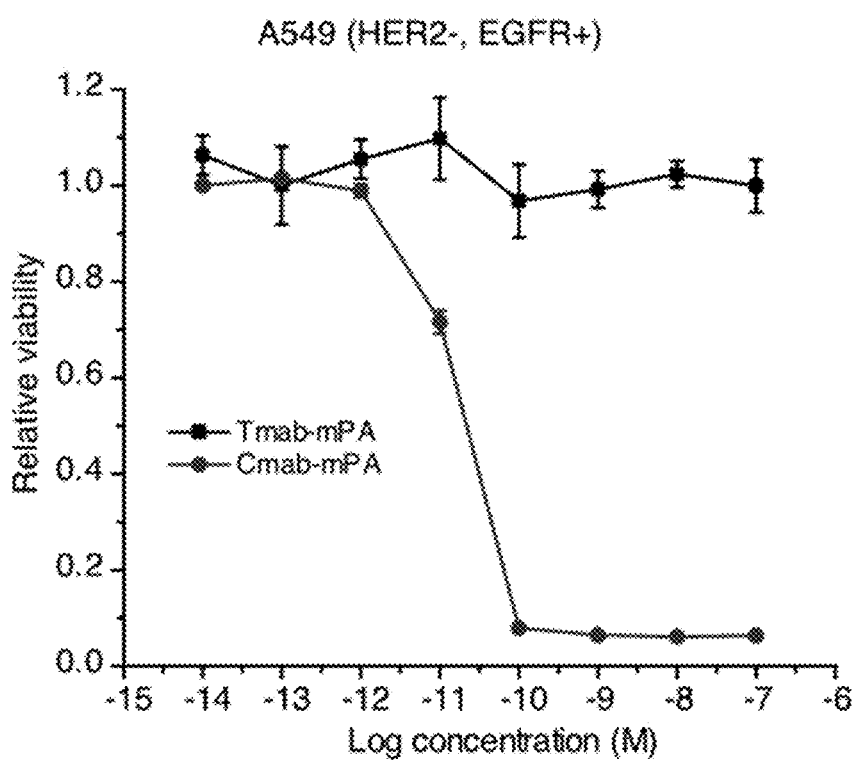
Figure 11C:
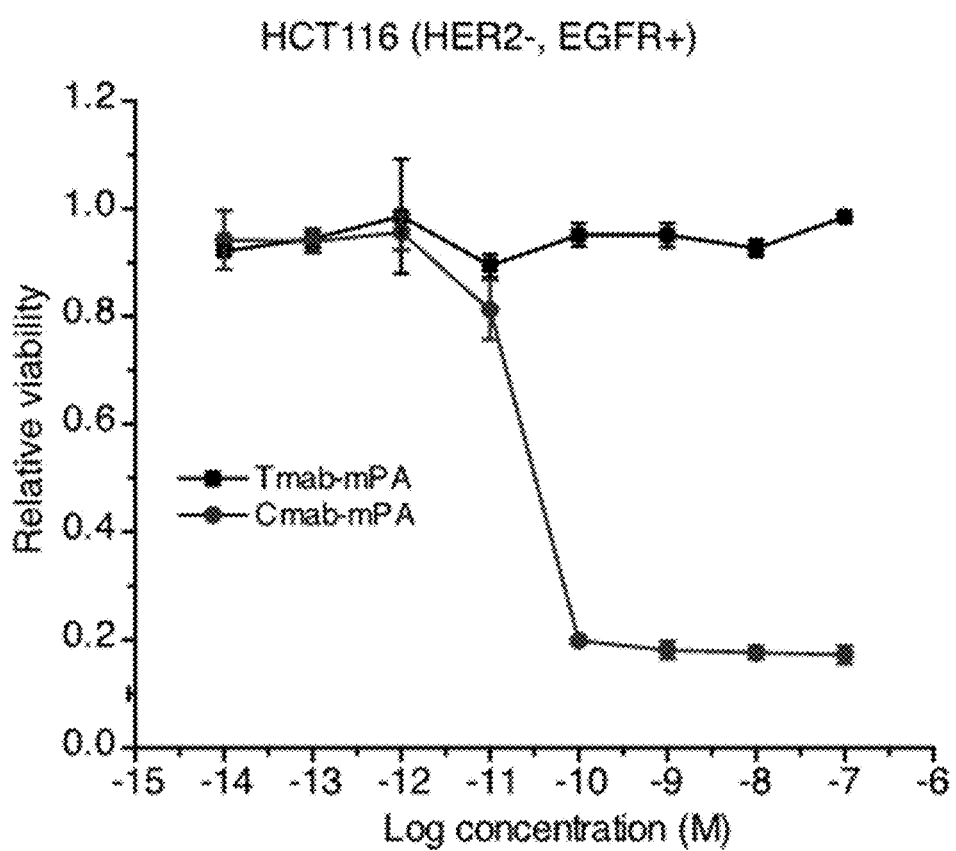
Figure 12:
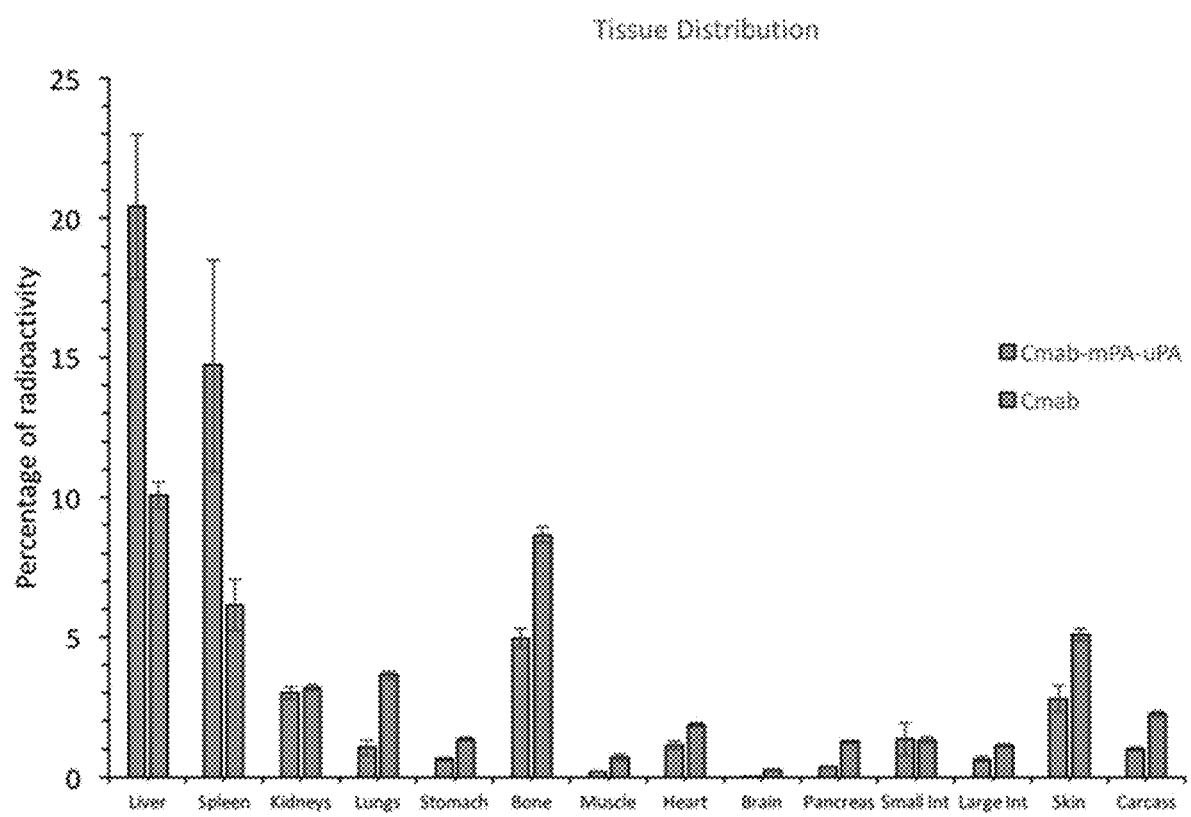
FIG. 12 shows a tissue distribution comparison between Cmab and Cmab-mPA-uPA. Tissues from different organs were measured for radioactivity.
Figure 13:
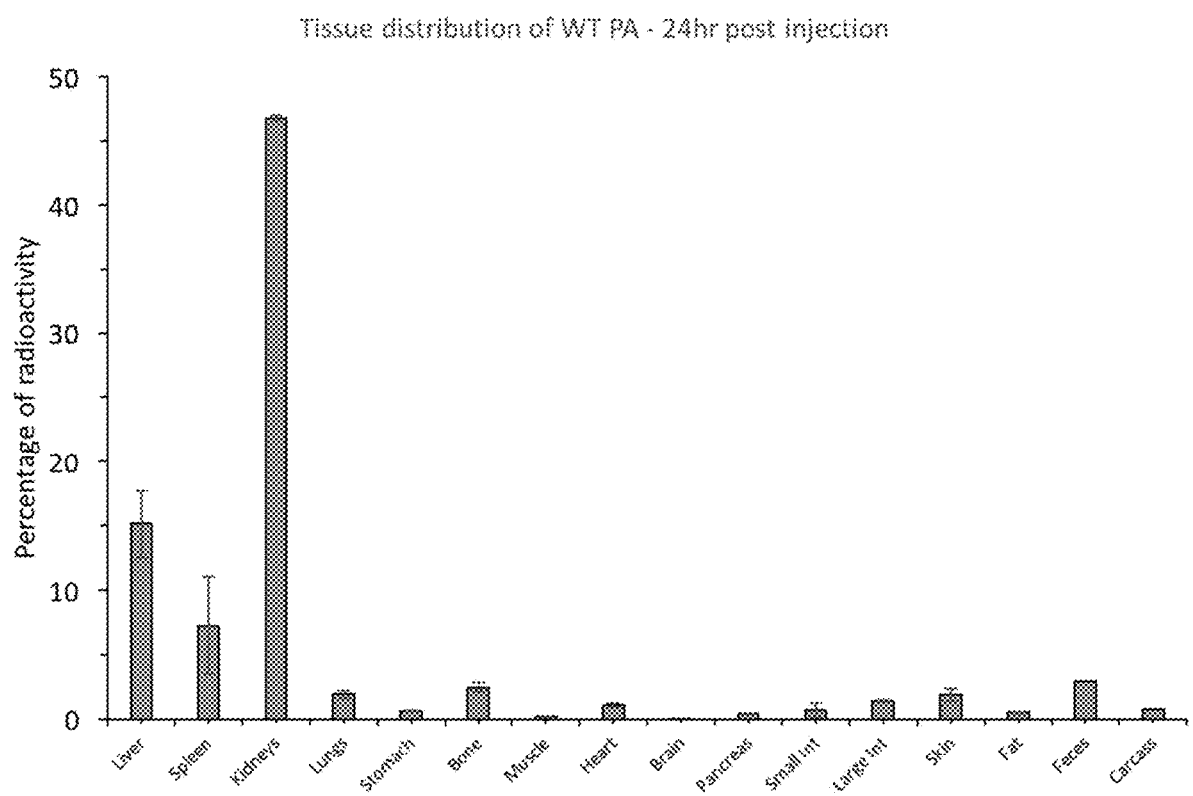
FIG. 13 shows a tissue distribution of WT PA 24 hours post-injection. Tissues from different organs were measured for radioactivity.

The specificity of this delivery method in different cell lines was next examined. When BT549, a triple negative breast cancer (TNBC) cell line lacking HER2, was treated with Tmab-mPA and LD under the same conditions as the BT474 cell line described above, no significant reduced viability was observed up to the highest concentration tested (FIG. 3C). Likewise, when EGFR-negative Jurkat cells were challenged with Cmab-mPA and LD, the cells showed very little change of viability (FIG. 3D). In contrast, significant toxicities were observed when both cell lines were treated with wildtype PA and LD (FIG. 10). In addition, to further verify the specificities of the IgG-mPA conjugates, the same cell lines were treated with Tmab-mPA or Cmab-mPA in the presence of LD. Major toxicity differences were observed between the two conjugates, in line with the relative HER2 and EGFR expression level (FIGS. 11A-11C). Taken together, these data suggest IgG and mPA can retain their separate functions in the conjugate and that the delivery of the protein cargo depends on both of them.

Figure 3E:
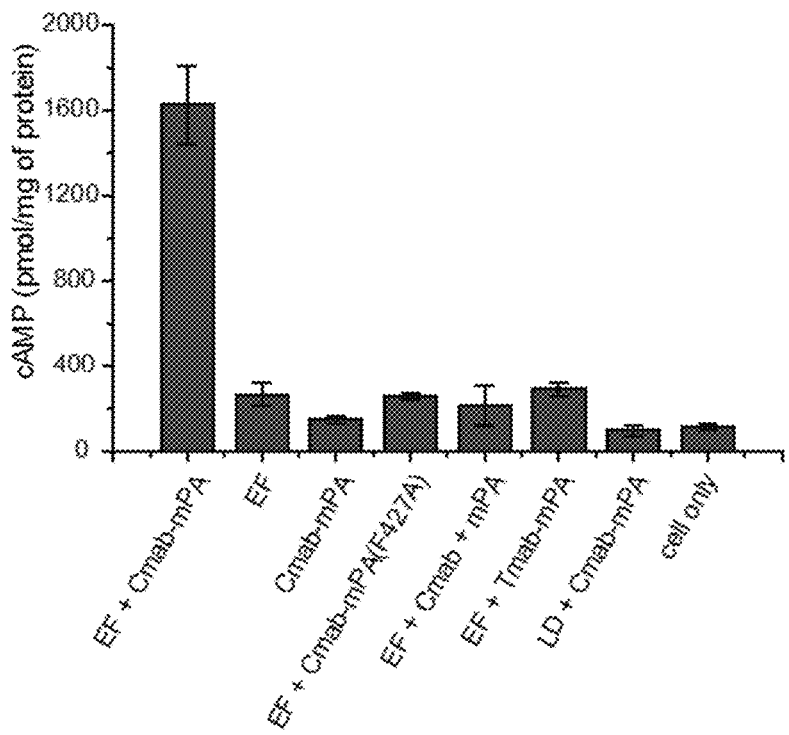

After verifying the delivery of DTA by IgG-mPA, whether the system can be used to deliver other protein cargos was examined. Edema factor (EF), one of the native effector proteins of anthrax toxin, is a calmodulin and $Ca^{2+}$ dependent adenylate cyclase, which increases intracellular concentration of cyclic AMP (cAMP)[23]. cAMP has been found to be involved in a variety of biological processes including the immune system. As a result, several drugs have been or are being developed to modulate cAMP level to attenuate autoimmune and inflammatory diseases. Accordingly, the ability to increase intracellular cAMP concentration through antibody-directed delivery of EF was examined. EGFR-expressing TNBC MDA-MB-231 cells were incubated with 20 nM of EF in the presence of Cmab-mPA or other controls for 2 hours and cAMP levels were subsequently measured using a commercial ELISA-based competition assay. A significant elevation of cAMP level was observed only when Cmab-mPA was used as the delivery vehicle. Translocation-disabled Cmab-mPA(F427A) failed to enhance cAMP concentration, suggesting entrapment of EF in the endosome. Unconjugated Cmab/mPA also showed similar levels of cAMP to those of the untreated background, indicating that conjugation is required for the activity of IgG-mPA (FIG. 3E). Additionally, Tmab-mPA with EF failed to increase the cAMP level, confirming again the delivery is antibody-dependent. When the cargo protein was replaced with LD, little change in the cAMP level was detected, demonstrating the effect is cargo-specific as well.

Figure 3F:
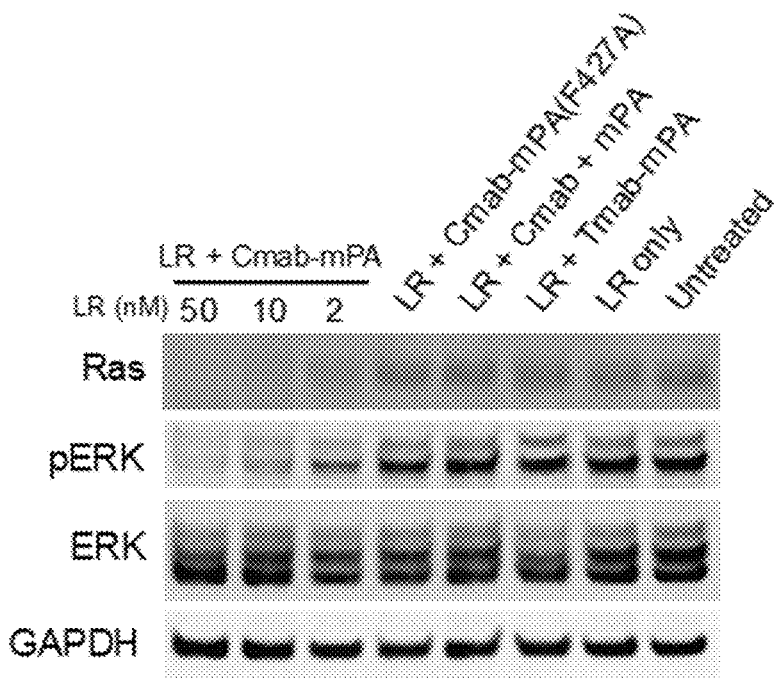
Figure 4A:
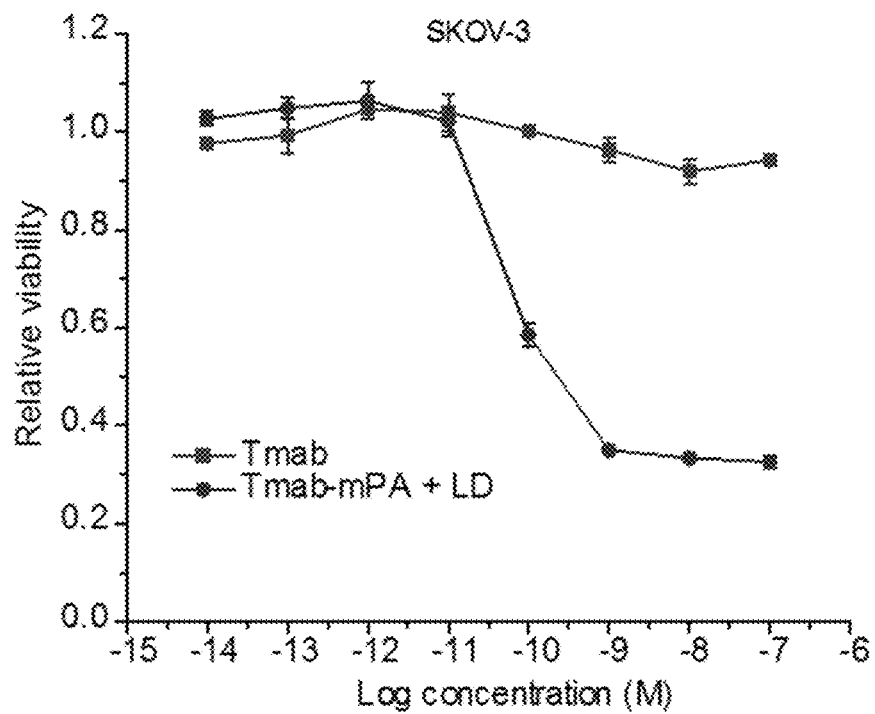
Figure 4B:
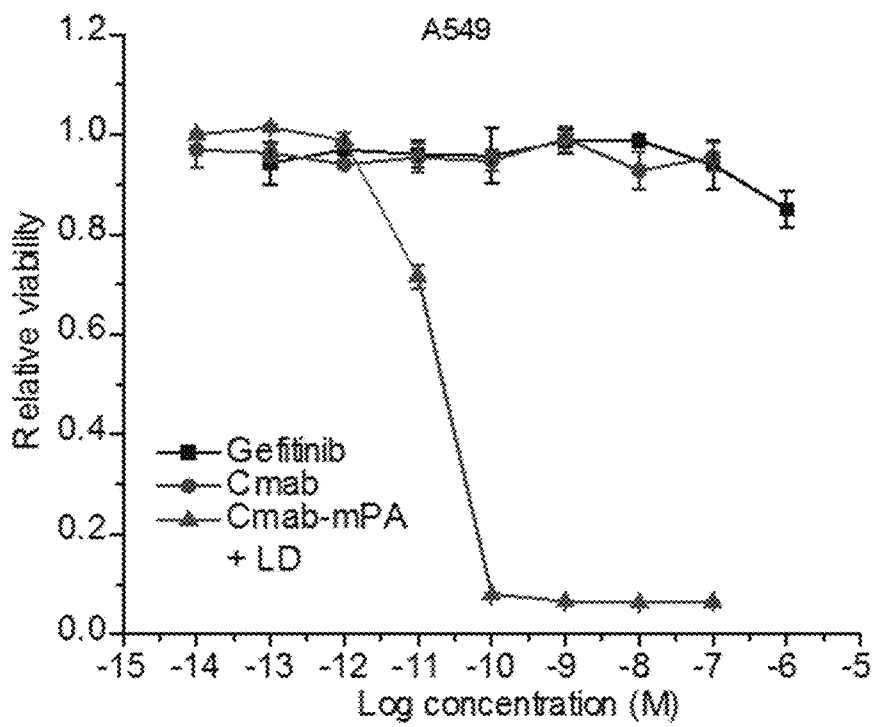
Figure 4C:
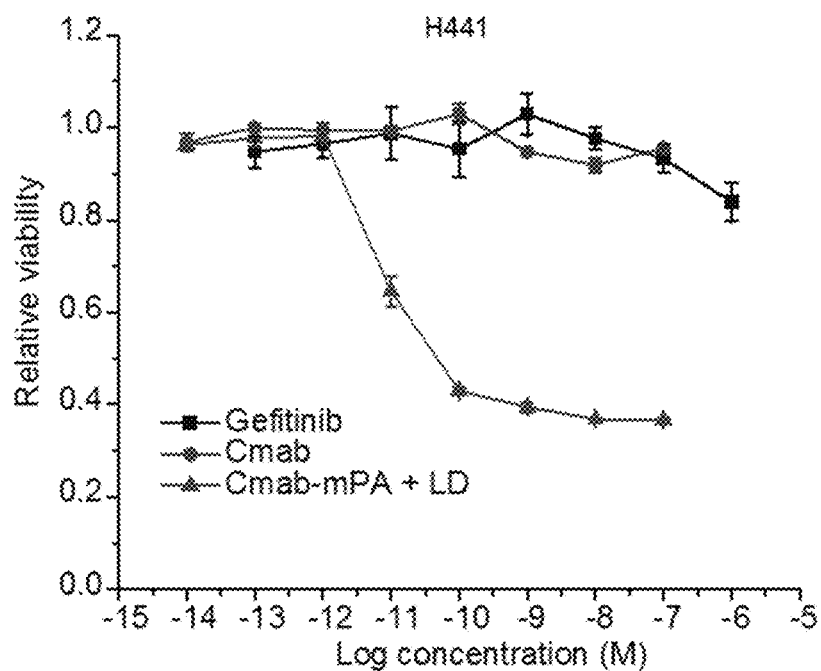
Figure 4D:
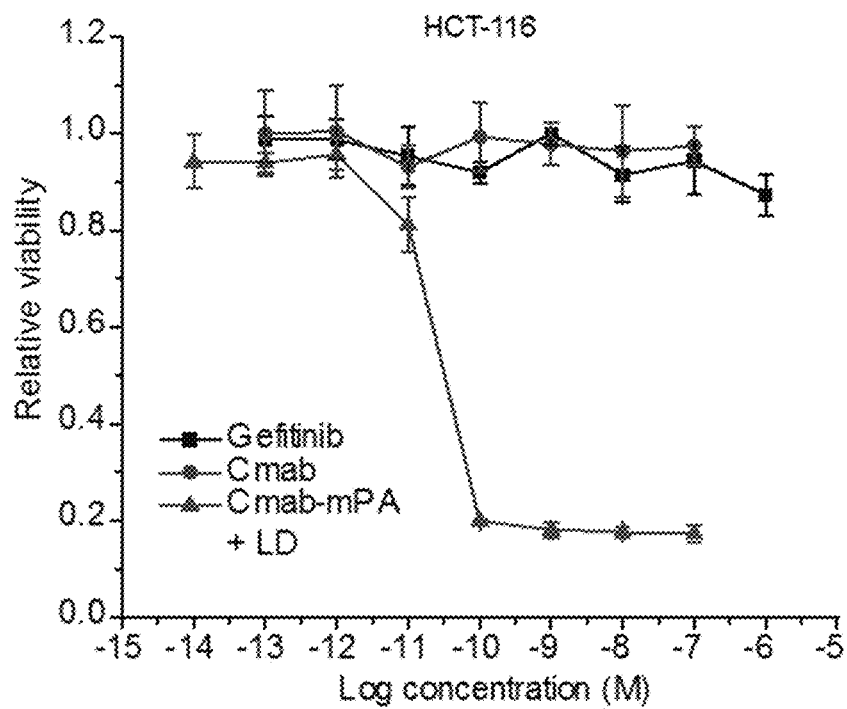
Figure 4E:
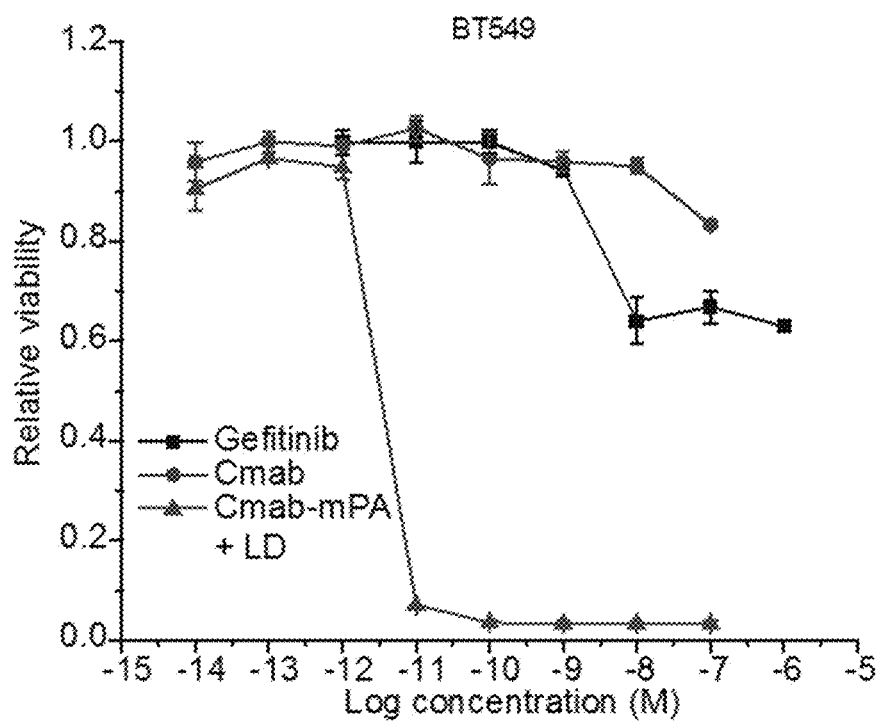
Figure 4F:
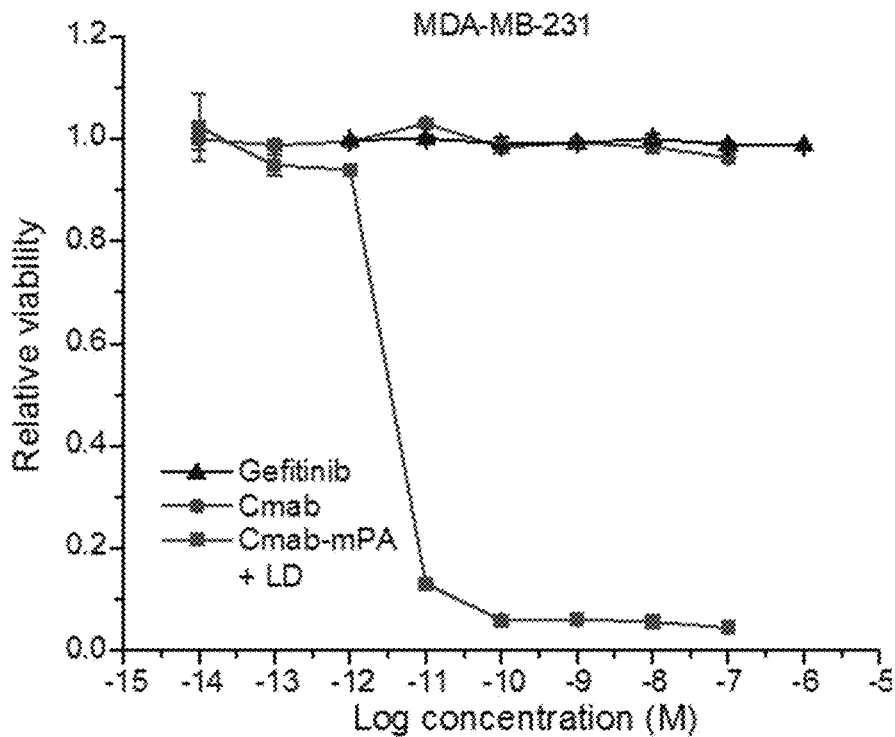

The protein cargo library was expanded to a third protein. Ras is an oncoprotein that plays a critical role in cancer development and Ras/Rap1-specific endopeptidase (RRSP) is a recently characterized Ras protease that rapidly cleaves Ras once delivered into cells by wildtype PA. MDA-MB-231 cells were treated with $LF_N$-RRSP (LR) in the presence of Cmab-mPA and other controls for 24 hours. The cells were subsequently lysed and analyzed by Western blots. As shown in FIG. 3F, Ras exhibited dose-dependent degradation as a result of RRSP-induced cleavage.

ERK is a downstream target protein activated by Ras and a key player in cell growth regulation. While the total amount of ERK remained unchanged across different conditions, phospho-ERK (pERK) showed dose-dependent suppression similar to Ras in the presence of LR and Cmab-mPA, indicating ERK1/2 dephosphorylation caused by RRSP. In contrast, as in earlier experiments, Cmab-mPA (F427A), unconjugated Cmab/mPA and Tmab-mPA did not show any obvious activity compared to the background.

Example 3: Overcoming Drug Resistance in Different HER2- and EGFR-Expressing Cancer Cell Lines with Trastuzumab- and Cetuximab-Mediated Delivery of Diphtheria Toxin A Since the approval of Tmab (HERCEPTIN®) for the treatment of HER2-overexpressing breast cancer, a significant number of patients with this type of breast cancer have developed resistance to Tmab treatment. Similarly, EGFR inhibitors such as Gefitinib and Cmab (ERBITUX®) have also been found to be ineffective in EGFR-positive cancer patients. Such resistance is often attributed to RAS mutations that lead to constitutive activation of EGFR signaling. In addition, previous studies have shown cancer cells often still retain HER2 or EGFR expression when they become refractory to HER2- or EGFR-based therapies. Based on these results, it was thought that drug resistance could be overcome by the Tmab- and Cmab-directed delivery of DTA, which induces cellular toxicity through a different mechanism.

Upon the intoxication of LD+Tmab-mPA, the HER2-expressing ovarian cancer cell line SKOV-3 displayed dose-dependent cell growth inhibition, but showed little response to Tmab treatment (FIG. 4A). Likewise, EGFR-positive human non-small-cell lung cancer (NSCLC) cell lines A549 and H441, colorectal cancer cell line HCT-116, and TNBC cell lines BT549 and MDA-MB-231 all showed high susceptibilities to LD+Cmab-mPA and no significant response to Cmab or Gefitinib treatment, consistent with previous studies (FIGS. 4B-4F).

Example 4: Orthogonal Targeting of Cancer-Specific Receptors and Proteases by the Antibody-mPA Conjugate Although HER2 and EGFR are often overexpressed in cancer cells, they also play essential roles in regular cellular functions and therefore are present in normal tissues. It is rare to find a single antigen exclusively on the cells of interest. This could be particularly problematic when the delivered cargo is a highly toxic protein, due to the possibility of one or more off-target effects. However, the specificity of a delivery system can be significantly enhanced if it requires two entities simultaneously at the target site for activation. During PA-mediated translocation, after binding to its cellular receptors, PA can only oligomerize upon cleavage by furin-family proteases after the sequence RKKR (SEQ ID NO: 13). Leveraging this requirement of a protease during PA activation, PA variants with re-engineered cleavage sites susceptible to MMP or uPA, both of which are over produced by tumor tissues and implicated in cancer cell growth and metastasis. These PA variants were combined with an IgG molecule using the modular conjugation strategy described above, resulting in the synthesis of Cmab-mPA-MMP and Cmab-mPA-uPA, which orthogonally target EGFR and MMP or uPA, respectively. These dual targeting IgG-mPA variants require the concurrent presence both the antigen and a specific cell surface protease for activation (FIG. 2D), providing another degree of selectivity for the delivery system. Using these variants, the highly specific delivery of DTA into particular cancer cell lines was demonstrated.

First, the susceptibilities of Cmab-mPA, Cmab-mPA-MMP and Cmab-mPA-uPA to proteases furin, MMP and uPA, respectively, were examined. The conjugates were incubated individually with furin, uPA, or MMP-9 for 3 hours at 37° C. and analyzed by reducing SDS-PAGE gel, which reduced the conjugates to mPA-tagged heavy chain (HC-mPA), HC, and light chain (LC). The cleavage of mPA was indicated by the downward shift of HC-mPA to HC-mPA$_{63}$ and the appearance of PA$_{20}$ band. As expected, each conjugate variant was only vulnerable to its specific protease. The band between HC-mPA$_{63}$ and HC in MMP-9 treated Cmab-MMP was possibly caused by subsequent cleavage of HC-mPA$_{63}$ by MMP-9.

Figure 5A:
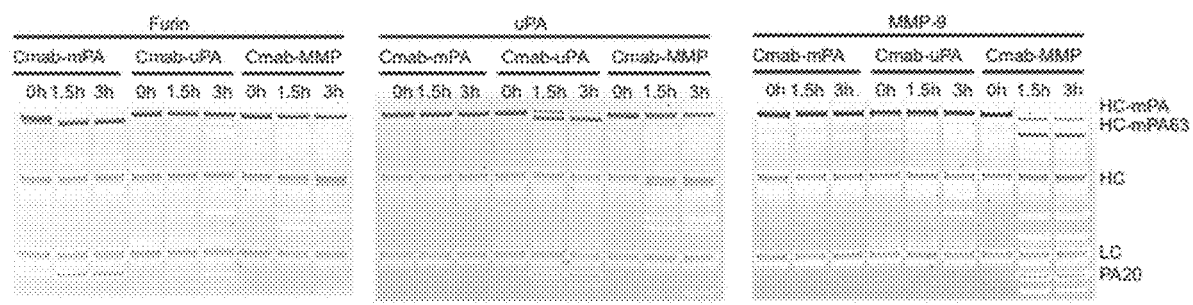
Figure 5B:
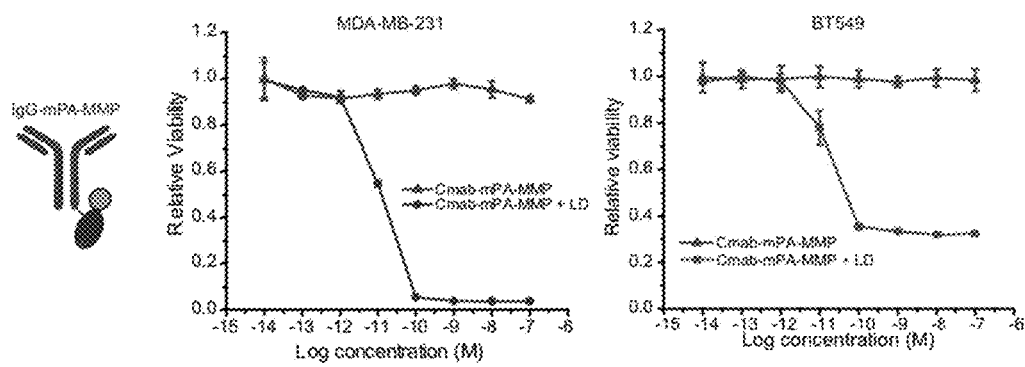
Figure 5C:
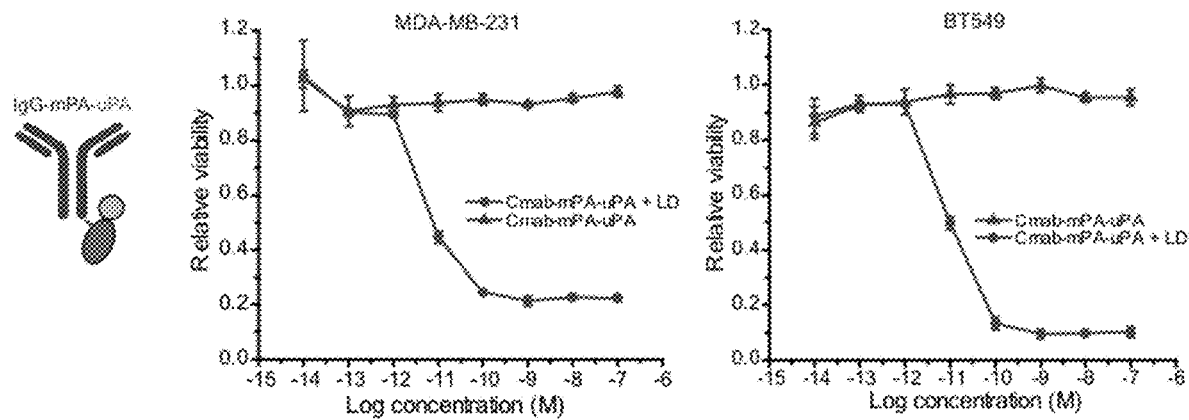
Figure 5D:
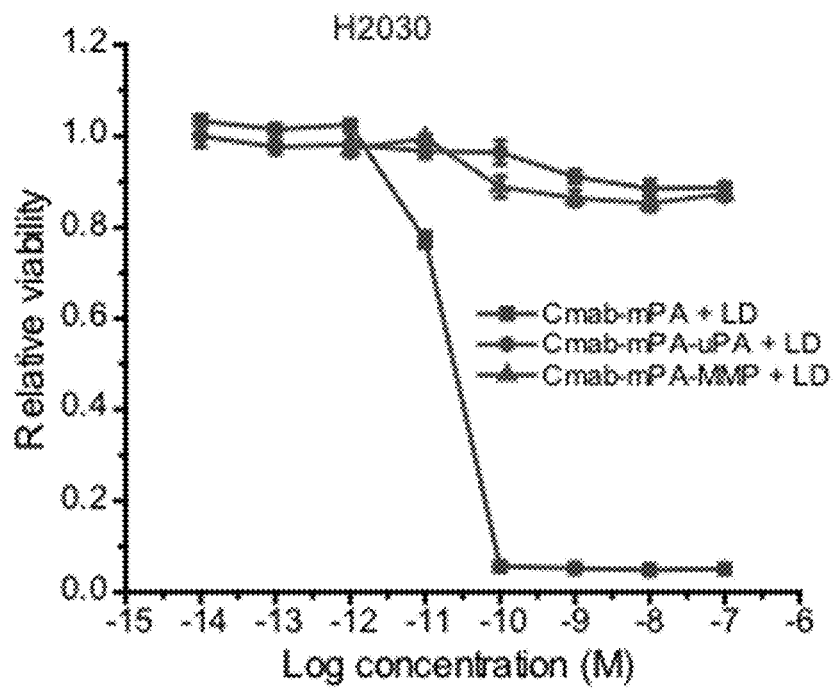
Figure 5E:
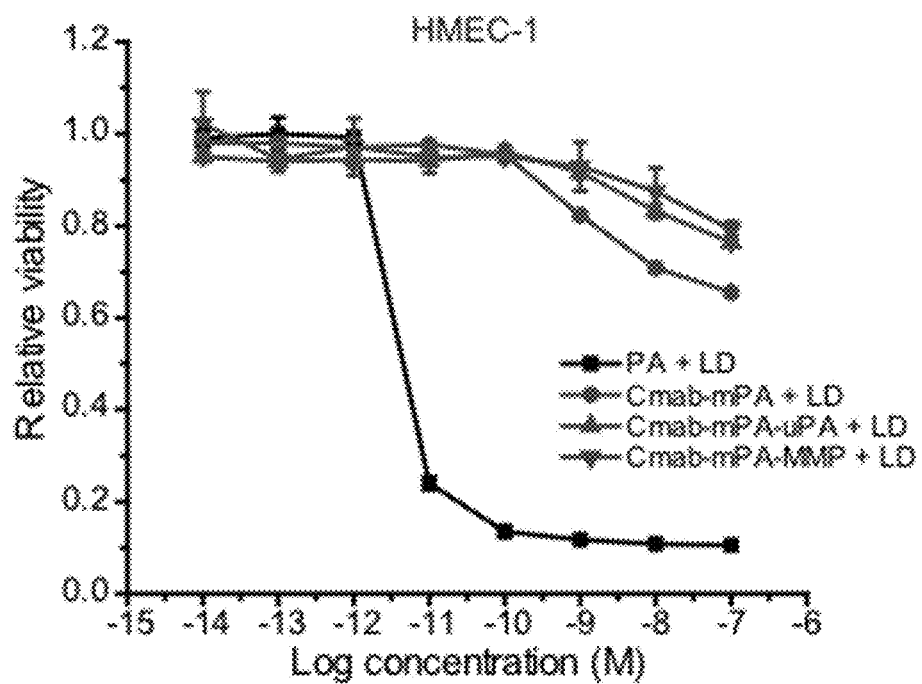

Then, whether Cmab-mPA-MMP and Cmab-mPA-uPA can target cells with both EGFR and their corresponding proteases, was examined. LD was again used as a model protein cargo due to its robust viability readout. TNBC cell lines BT549 and MDA-MB-231, which express EGFR, MMP-9, and uPA, were treated with Cmab-mPA-MMP or Cmab-mPA-uPA in the presence or absence of LD for 72 hours. Both cell lines showed high sensitivities to the IgG-mPA variants that are comparable to Cmab-mPA, indicating the modified cleavage site did not significantly affect IgG-mPA activity when the targeted protease was present (FIGS. 5B-5C). In contrast, H2030 cells, which are EGFR-positive but lack MMP and uPA, showed complete resistance to LD with Cmab-mPA-MMP and Cmab-mPA-uPA but not with Cmab-mPA (FIG. 5D). In addition, more attenuated LD toxicity was observed when normal human endothelial HMEC-1 cells were treated with Cmab-mPA-MMP and Cmab-mPA-uPA when compared to Cmab-mPA, consistent with the assumption that the dual-targeting further improves the specificity of the delivery system. HMEC-1 still remained highly susceptible to wild-type PA+LD, confirming that the cell line is still sensitive to LD delivery (FIG. 5E).

Figure 6A:
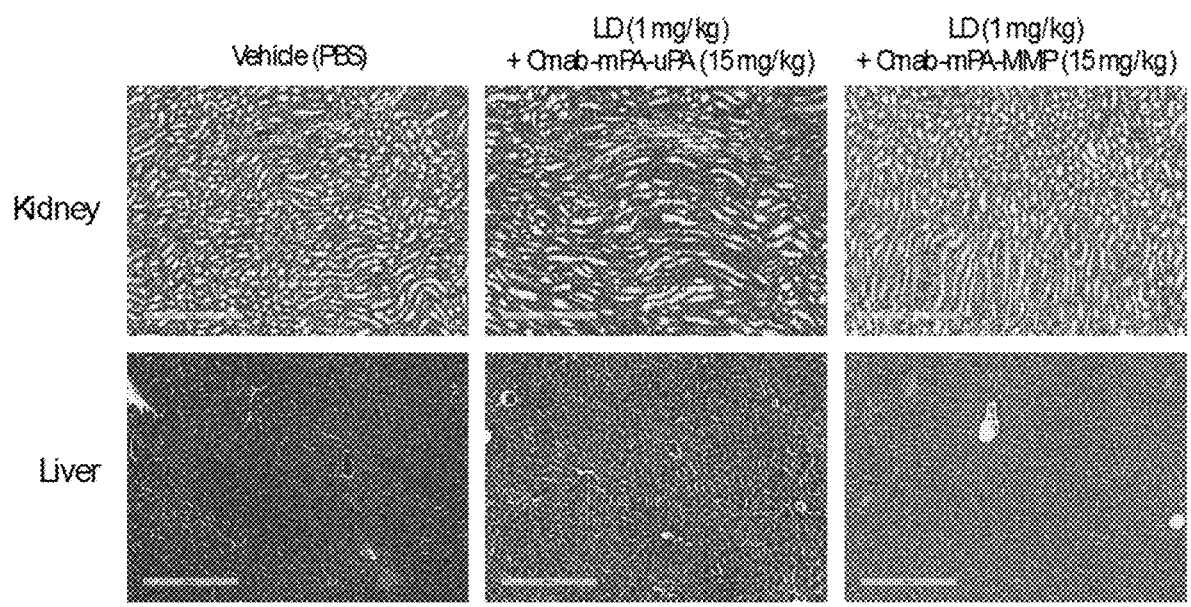

Example 5: Safety Profile and Pharmacokinetic Properties of Protein Toxin Delivered by Orthogonal Targeting Cmab-mPA Variants Whether the attenuated toxicity observed in cell culture was able to translate into animal model was next examined. Female nude mice were challenged intravenously with 1 mg/kg of LD alone or in combination with increasing amounts of Cmab-mPA-uPA or Cmab-mPA-MMP. The injected mice were closely monitored for any outward signs of toxicity for 48 hours. After the mice were sacrificed, the tissue samples from kidney and liver were also subjected to microscopic examinations. Cmab-mPA-uPA and Cmab-mPA-MMP combined with LD showed no outward or histological signs of toxicity up to the highest doses (15 mg/kg) tested (FIG. 6A), significantly higher than any of the previously reported PA variants.

Figure 6B:
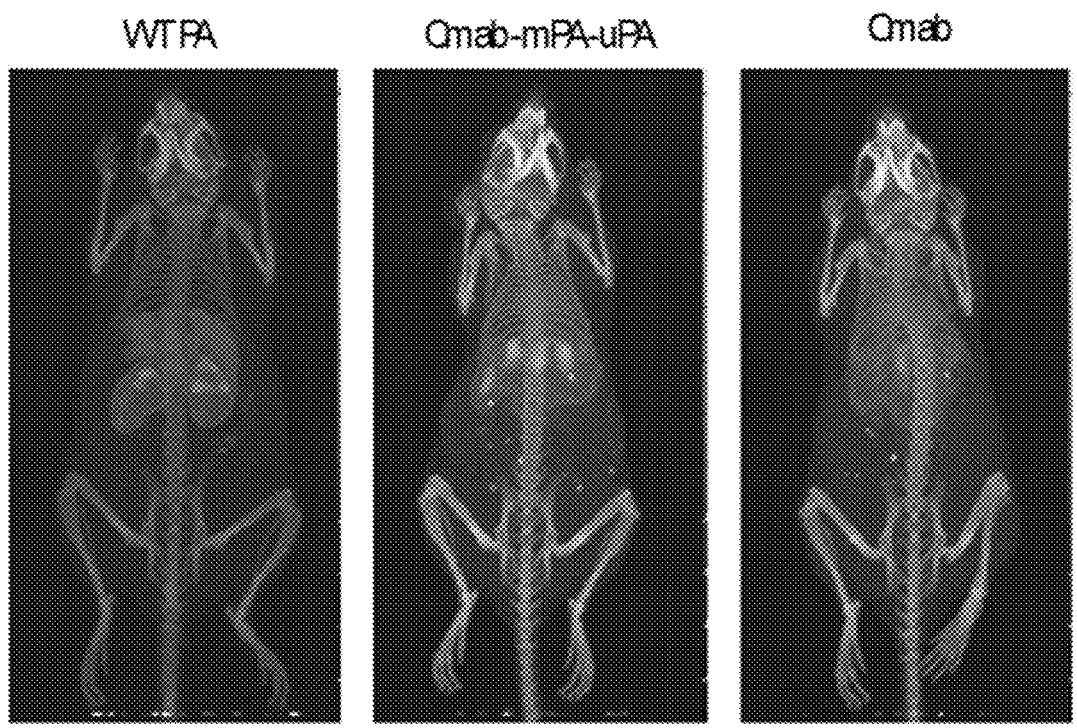
Figure 6C:
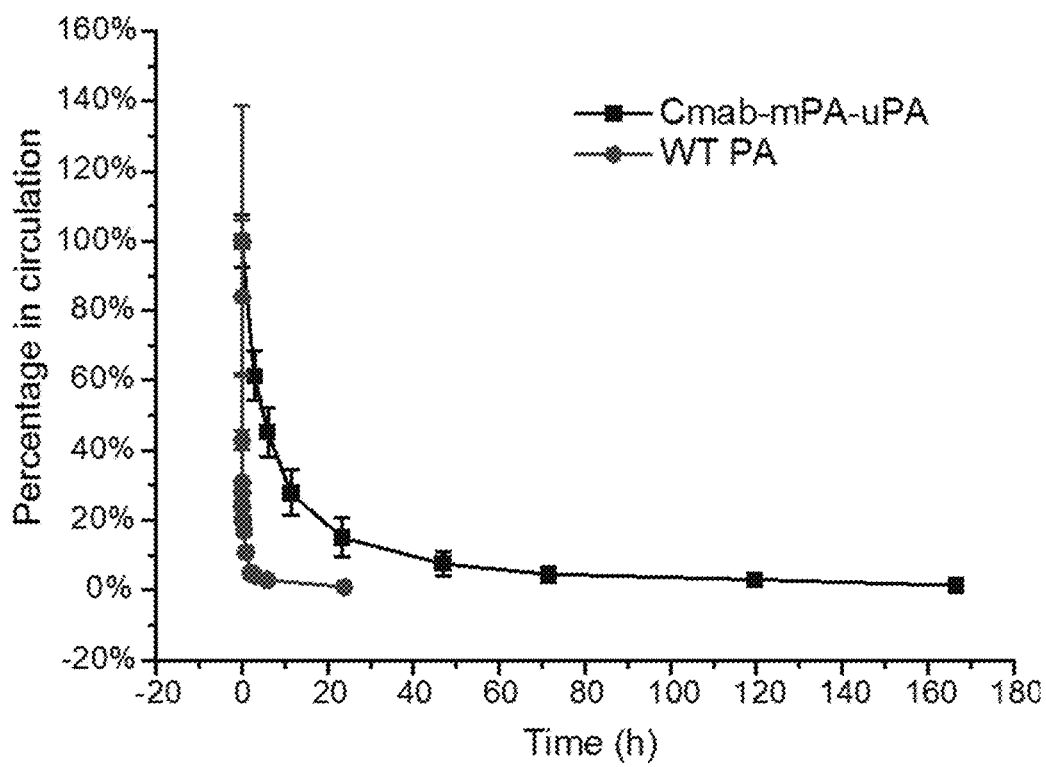

In order to study the pharmacokinetic properties of the Cmab-mPA variants, wild-type PA, Cmab-mPA-uPA, or Cmab were labeled with radioactive 89Zr, and mice (n=4) were injected intravenously with 1 mg/kg of each protein. PET images acquired 6 hours post-injection showed similar biodistribution patterns between Cmab and Cmab-mPA-uPA, with some accumulation in liver and significant portions still remaining in circulation (FIG. 6B). In contrast, most of the wild-type PA was found in liver, indicating a fast clearance. In parallel, blood samples from different treatment groups were collected at specified time points for radioactivity measurements by a gamma counter. Consistent with the PET imaging results, Cmab-mPA-uPA showed a significantly prolonged clearance time compared to the wild type PA (FIG. 6C).

Materials and Methods

Materials:

Fmoc-protected L- and D-amino acids used for peptide synthesis were purchased from ChemImpex. Plasmids of Trastuzumab and Cetuximab and the plasmid encoding LF$_N$-RRSP were provided. All antibodies used were purchased from Cell Signaling unless stated otherwise. All media used in cell culture were purchased from Thermo Fisher.

Synthesis and Purification of Peptide Linkers:

Peptide linkers were synthesized on ChemMatrix resin with a Rink amide linker using either manual flow peptide synthesis or an automated flow peptide synthesizer as previously described. The bromoacetamide or maleimide was coupled on resin as described below. The crude peptides were cleaved by TFA/H$_2$O (97.5:2.5) and purified by semi-preparative RP-HPLC with Agilent Zorbax 300SB C$_{18}$ column (9.4×250 mm, 5 um) at a flow rate of 4 mL/min using the gradient of 1-31% acetonitrile over 80 min. Pure HPLC fractions were subsequently pooled and analyzed by LC-MS.

Construction of PA and IgG Mutants:

The plasmids of mPA (N682A, D683A), mPAC (N682A, D683A, K563C), and mPACA (N682A, D683A, K563C, F427A) were prepared from wild type PA using QuickChange multi site-directed mutagenesis kit (Agilent) according to the manufacturer's protocol. The furin cleavage site 164RKKR167 in mPAC was replaced by the uPA substrate sequence PGSGRSA or gelatinase substrate sequence GPLGMLSQ to give mPAC-uPA or mPAC-MMP using QuickChange single site-directed mutagenesis kit (Agilent). Using the same kit, the sortase-specific conjugation tag LPSTGG (SEQ ID NO: 59) was inserted at the C-terminus of the heavy chain of Trastuzumab and Cetuximab.

Expression and Purification of PA Mutants, EF, and LFN-RRSP:

All non-IgG proteins were expressed in *E. coli* BL21 (DE3) cells from Thermo Fisher. PA variants were expressed and purified as previously described. In short, the cell pellet was first resuspended in sucrose buffer (20 mM Tris pH 8.5, 1 mM EDTA, 20% sucrose) and then incubated with 5 mM MgSO4. The supernatant was purified by an anion exchange column, after which the pure fractions were pooled and concentrated based on the analysis of SDS-PAGE. EF and LFN-RRSP were expressed in Champion PET-SUMO vectors with a His tag in *E. coli* BL21(DE3) and were induced at OD 0.7-0.9 with 0.4 mM IPTG at 20° C. for 16 hours. The proteins were purified by a HisTrap FF Ni-NTA column. The SUMO was cleaved by SUMO protease and removed by size exclusion chromatography.

Expression and Purification of IgGs:

Trastuzumab and Cetuximab in a gWiz Vector were transiently transfected using PEI and expressed in FreeStyle 293-F cells (Thermo Fisher) according to the manufacturer's protocol. The IgGs were subsequently purified from the medium by Protein A affinity chromatography (Genscript) and stored in PBS at −80° C.

Conjugation of mPA and IgGs:

mPA (or any of its variants) (400 uM) was first conjugated with the peptide linker (2 mM) in 20 mM Tris and 150 mM NaCl (pH 8.5). After the reaction went to completion in 1 hour, the excess peptide was removed by three rounds of buffer exchange with 30K Amicon ultra-15 centrifugal filter (Millipore). The resulting $G_3$-mPA (100 uM) was incubated with IgG-LPSTGG (SEQ ID NO: 59) (40 uM) in the presence of 5 uM of triple mutant sortase (SrtA*) in sortase buffer (50 mM Tris, 150 mM NaCl, 10 mM $CaCl_2$, pH 7.5) for 1 hour at room temperature. The reaction mixture was then loaded onto a HiLoad 16/600 Superdex 200 pg size exclusion column (GE). The fractions containing IgG-mPA and IgG-$(mPA)_2$ were pooled and purified again by 5-mL HiTrap Q anion exchange column (GE) to give pure IgG-mPA.

Igg-Mpa Stability:

Cmab-mPA and Cmab-M-mPA were prepared with a bromoacetamide linker and a maleimide linker, respectively, and were incubated in MEM supplemented with 10% FBS at 37° C. Samples from different time points were analyzed by Western blot using an anti-PA antibody (Santa Cruz Biotechnology).

In Vitro Cleavage of Cetuximab-mPA Variants by Furin, uPA, and MMP-9:

10 μg of different Cetuxiamb-mPA variants were incubated with 1 μl of furin (>2000 unit/ml, Sigma), 1 μg of uPA (Millipore), or 0.2 μg of MMP-9 (Millipore) in a total reaction volume of 40 μl. The cleavage reactions were performed in similar conditions as previously described. Furin cleavage was performed in 25 mM HEPES (pH 7.5), 150 mM NaCl, 0.2 mM EDTA, 0.2 mM EGTA, 1.0 mM $CaCl_2$, and 1.0 mM $MgCl_2$. uPA cleavage was performed in 20 mM Tris-HCl (pH 7.5) and 150 mM NaCl. MMP-9 cleavage was carried out in 50 mM HEPES (pH 7.5), 10 mM $CaCl_2$, 200 mM NaCl, 0.05% (v/v) Brij-35, and 50 μM $ZnSO_4$. Aliquots at different time points were analyzed by reducing SDS-PAGE using Bolt 4-12% Bis-Tris plus gel (Thermo Fisher).

Cell Culture:

All cell lines were purchased from American Type Culture Collection (Manassas, Va.). The cells were grown at 37° C. in a 5% $CO_2$ environment. All cells were maintained according to the instructions on ATCC except that MDA-MB-231 cells were grown in DMEM with 10% FBS.

Cell Viability Assays:

Cells were seeded in a 96-well plate at a density of $5 \times 10^3$ per well and allowed to attach overnight. The next day, the cells were treated with 10-fold serial dilutions of different protein cargos with or without various IgG-PA variants for 72 hours. The cell viability was measured by CellTiter-Glo luminescent assay (Promega) following the manufacturer's protocol. The relative viability was normalized to cells without treatment.

Camp Assay:

MDA-MB-231 cells ($1.5 \times 10^4$) were plated in a 96-well plate on the previous day of treatment. Cells were incubated with 20 nM EF or LD in the presence or absence of 100 nM different IgG-mPA variants for 2 hours. Cells were lysed in 0.1 M HCl with 0.5% Triton X-100. A colorimetric competitive ELISA kit (Enzo Life Science) was used to measure the intracellular cAMP levels according to the manufacturer's instructions.

Western Blotting:

MDA-MB-231 cells were plated at $2 \times 10^5$ cells/well in a 12-well plate. After 24 hours, the cells were treated with 50 nM LFN-RRSP (LR) in the presence or absence of different IgG-mPA variants for another 24 hours. Subsequently, the medium was removed and the cells were lysed by RIPA buffer (10 mM pH 8.0 Tris-Cl, 1 mM EDTA, 1% Triton X-100, 0.1% sodium deoxycholate, 0.1% SDS, 140 mM NaCl, 1 mM PMSF) supplemented with Roche protein inhibitor for 20 minutes on ice. The lysate was separated by SDS-PAGE and transferred onto a PVDF membrane (Bio-Rad) using a Bio-Rad Trans-Blot turbo transfer system. The membrane was blocked with LI-COR blocking buffer on a shaker at room temperature for 1 hour before the membrane was incubated with different primary antibodies in TBST buffer and 0.1% Tween overnight at 4° C. On the next day, the membrane was washed by TBST three times and then incubated with the appropriate fluorescent secondary antibody in TBST on a shaker for 1 hour at room temperature. The imaging was performed by the ChemiDoc MP imaging system (Bio-Rad). A Serial detection of proteins was accomplished by stripping the membrane with stripping buffer (Thermo Fisher) and repeating the above staining procedure.

Histopathological Analysis:

All animal work was conducted in accordance with an approved protocol. A dose-escalation protocol was used to characterize the potential toxicity of LD in combination with dual-targeting Cetuximab-mPA variants. Female nude mice between 8 to 12 weeks (n=3) were anesthetized by isoflurane inhalation and injected intravenously with either a single dose of vehicle PBS or LD (1 mg/kg). For the combination dose, a second injection was performed to administer the 3 mg/kg or 15 mg/kg of Cetuximab-mPA-uPA or Cetuximab-mPA-MMP. The mice were closely monitored for any signs of toxicity. After 48 hours, the mice were euthanized, tissues were fixed in 4% formalin, embedded in paraffin, and sections were stained with hematoxylin and eosin (H&E) for microscopic analysis by a pathologist.

PK Study:

Female nude mice between 8 to 12 weeks were injected intravenously (i.v.) through the tail vain with wild type PA or Cetuximab-mPA-uPA labeled with 89Zr (Washington University School of Medicine in St. Louis) at 1 mg/kg (n=4). 5-15 mg of blood samples at the indicated time points were collected by tail snipping, and the radioactivity was measured by a PerkinElmer Wizard 2 gamma counter. The PET scans were acquired on a G8 PET/CT preclinical imaging system (PerkinElmer). After 166 hours, the mice were sacrificed by $CO_2$ followed by cervical dislocation. The organs and tissues were collected and measured by the gamma counter.

REFERENCES

1. Leader, B., Baca, Q. J. & Golan, D. E. Protein therapeutics: A summary and pharmacological classification. Nature Reviews Drug Discovery 7, 21-39 (2008).
2. Lagassé, H. A. D. et al. Recent advances in (therapeutic protein) drug development. F1000Research 6, 113 (2017).
3. Akishiba, M. et al. Cytosolic antibody delivery by lipid-sensitive endosomolytic peptide. Nat. Chem. 9, 751-761 (2017).
4. Zhang, Z. et al. The fluorination effect of fluoroamphiphiles in cytosolic protein delivery. Nat. Commun. 9, (2018).
5. Zuris, J. A. et al. Cationic lipid-mediated delivery of proteins enables efficient protein-based genome editing in vitro and in vivo. Nat. Biotechnol. 33, 73-80 (2015).

6. Guidotti, G., Brambilla, L. & Rossi, D. Cell-Penetrating Peptides: From Basic Research to Clinics. Trends in Pharmacological Sciences 38, 406-424 (2017).
7. Ng, D. Y. W. et al. Constructing hybrid protein zymogens through protective dendritic assembly. Angew. Chemie—Int. Ed. 53, 324-328 (2014).
8. Scaletti, F. et al. Protein delivery into cells using inorganic nanoparticle-protein supramolecular assemblies. Chem. Soc. Rev. (2018). doi:10.1039/C8CS00008E
9. Mout, R. et al. General Strategy for Direct Cytosolic Protein Delivery via Protein-Nanoparticle Co-engineering. ACS Nano 11, 6416-6421 (2017).
10. Weiner, L. M., Surana, R. & Wang, S. Monoclonal antibodies: Versatile platforms for cancer immunotherapy. Nature Reviews Immunology 10, 317-327 (2010).
11. Weiner, G. J. Building better monoclonal antibody-based therapeutics. Nature Reviews Cancer 15, 361-370 (2015).
12. Scott, A. M., Wolchok, J. D. & Old, L. J. Antibody therapy of cancer. Nature Reviews Cancer 12, 278-287 (2012).
13. Carter, P. J. & Lazar, G. A. Next generation antibody drugs: Pursuit of the 'high-hanging fruit'. Nature Reviews Drug Discovery 17, 197-223 (2018).
14. Kaplon, H. & Reichert, J. M. Antibodies to watch in 2018. MAbs 10, 183-203 (2018).
15. Sliwkowski, M. X. & Mellman, I. Antibody therapeutics in cancer. Science 341, 1192-1198 (2013).
16. Akbari, B. et al. Immunotoxins in cancer therapy: Review and update. International Reviews of Immunology 36, 207-219 (2017).
17. Beck, A., Goetsch, L., Dumontet, C. & Corvaïa, N. Strategies and challenges for the next generation of antibody-drug conjugates. Nature Reviews Drug Discovery 16, 315-337 (2017).
18. Chalouni, C. & Doll, S. Fate of Antibody-Drug Conjugates in Cancer Cells. Journal of Experimental and Clinical Cancer Research 37, (2018).
19. Kalim, M. et al. Intracellular trafficking of new anticancer therapeutics: Antibody-drug conjugates. Drug Design, Development and Therapy 11, 2265-2276 (2017).
20. Alewine, C., Hassan, R. & Pastan, I. Advances in Anticancer Immunotoxin Therapy. Oncologist 20, 176-185 (2015).
21. Alouf, J. & Popoff, M. The Comprehensive Sourcebook of Bacterial Protein Toxins. The Comprehensive Sourcebook of Bacterial Protein Toxins (2006). doi:10.1016/B978-0-12-088445-2.X5000-8
22. Pannifer, A. D. et al. Crystal structure of the anthrax lethal factor. Nature 414, 229-233 (2001).
23. Leppla, S. H. et al. Anthrax toxin edema factor: a bacterial adenylate cyclase that increases cyclic AMP concentrations of eukaryotic cells. Proc. Natl. Acad. Sci. 79, 3162-3166 (1982).
24. Klimpel, K. R., Molloy, S. S., Thomas, G. & Leppla, S. H. Anthrax toxin protective antigen is activated by a cell surface protease with the sequence specificity and catalytic properties of furin. Proc. Natl. Acad. Sci. 89, 10277-10281 (1992).
25. Milne, J. C., Furlong, D., Hanna, P. C., Wall, J. S. & Collier, R. J. Anthrax protective antigen forms oligomers during intoxication of mammalian cells. J. Biol. Chem. 269, 20607-20612 (1994).
26. Kintzer, A. F. et al. The Protective Antigen Component of Anthrax Toxin Forms Functional Octameric Complexes. J. Mol. Biol. 392, 614-629 (2009).
27. Feld, G. K. et al. Structural basis for the unfolding of anthrax lethal factor by protective antigen oligomers. Nat. Struct. Mol. Biol. 17, 1383-1390 (2010).
28. Mogridge, J., Cunningham, K. & Collier, R. J. Stoichiometry of anthrax toxin complexes. Biochemistry 41, 1079-1082 (2002).
29. Nassi, S., Collier, R. J. & Finkelstein, A. PA63 channel of anthrax toxin: An extended??-barrel. Biochemistry 41, 1445-1450 (2002).
30. Lacy, D. B., Wigelsworth, D. J., Melnyk, R. A., Harrison, S. C. & Collier, R. J. Structure of heptameric protective antigen bound to an anthrax toxin receptor: A role for receptor in pH-dependent pore formation. Proc. Natl. Acad. Sci. 101, 13147-13151 (2004).
31. Miller, C. J., Elliott, J. L. & Collier, R. J. Anthrax protective antigen: Prepore-to-pore conversion. Biochemistry 38, 10432-10441 (1999).
32. Hu, H. & Leppla, S. H. Anthrax toxin uptake by primary immune cells as determined with a lethal factor-beta-lactamase fusion protein. PLoS One 4, e7946 (2009).
33. Milne, J. C., Blanket, S. R., Hanna, P. C. & Collier, R. J. Protective antigen-binding domain of anthrax lethal factor mediates translocation of a heterologous protein fused to its amino- or carboxy-terminus. Mol. Microbiol. 15, 661-666 (1995).
34. Arora, N., Klimpel, K. R., Singh, Y. & Leppla, S. H. Fusions of anthrax toxin lethal factor to the ADP-ribosylation domain of Pseudomonas exotoxin A are potent cytotoxins which are translocated to the cytosol of mammalian cells. J. Biol. Chem. 267, 15542-15548 (1992).
35. Antic, I., Biancucci, M., Zhu, Y., Gius, D. R. & Satchell, K. J. F. Site-specific processing of Ras and Rap1 Switch i by a MARTX toxin effector domain. Nat. Commun. 6, (2015).
36. Liao, X., Rabideau, A. E. & Pentelute, B. L. Delivery of antibody mimics into mammalian cells via anthrax toxin protective antigen. ChemBioChem 15, 2458-2466 (2014).
37. Rabideau, A. E., Liao, X. & Pentelute, B. L. Delivery of mirror image polypeptides into cells. Chem. Sci. 6, 648-653 (2015).
38. Mechaly, A., McCluskey, A. J. & John Collier, R. Changing the receptor specificity of anthrax toxin. MBio 3, (2012).
39. McCluskey, A. J., Olive, A. J., Starnbach, M. N. & Collier, R. J. Targeting HER2-positive cancer cells with receptor-redirected anthrax protective antigen. Mol. Oncol. 7, 440-451 (2013).
40. Liu, S., Netzel-Arnett, S., Birkedal-Hansen, H. & Leppla, S. H. Tumor cell-selective cytotoxicity of matrix metalloproteinase-activated anthrax toxin. Cancer Res. 60, 6061-6067 (2000).
41. Liu, S., Bugge, T. H. & Leppla, S. H. Targeting of Tumor Cells by Cell Surface Urokinase Plasminogen Activator-dependent Anthrax Toxin. J. Biol. Chem. 276, 17976-17984 (2001).
42. Mourez, M. et al. Mapping dominant-negative mutations of anthrax protective antigen by scanning mutagenesis. Proc. Natl. Acad. Sci. 100, 13803-13808 (2003).
43. Rosovitz, M. J. et al. Alanine-scanning mutations in domain 4 of anthrax toxin protective antigen reveal residues important for binding to the cellular receptor and to a neutralizing monoclonal antibody. J. Biol. Chem. 278, 30936-30944 (2003).
44. Chen, I., Dorr, B. M. & Liu, D. R. A general strategy for the evolution of bond-forming enzymes using yeast display. Proc. Natl. Acad. Sci. 108, 11399-11404 (2011).

45. Alley, S. C. et al. Contribution of linker stability to the activities of anticancer immunoconjugates. Bioconjug. Chem. 19, 759-765 (2008).
46. Lyon, R. P. et al. Self-hydrolyzing maleimides improve the stability and pharmacological properties of antibody-drug conjugates. Nat. Biotechnol. 32, 1059-1062 (2014).
47. Ciardiello, F. & Tortora, G. EGFR Antagonists in Cancer Treatment. N. Engl. J. Med. 358, 1160-1174 (2008).
48. Berchuck, A. et al. Overexpression of HER-2/neu is associated with poor survival in advanced epithelial ovarian cancer. Cancer Res. 50, 4087-91 (1990).
49. Gravalos, C. & Jimeno, A. HER2 in gastric cancer: A new prognostic factor and a novel therapeutic target. Annals of Oncology 19, 1523-1529 (2008).
50. Arteaga, C. L. et al. Treatment of HER2-positive breast cancer: current status and future perspectives. Nat. Rev. Clin. Oncol. 9, 16-32 (2011).
51. Yewale, C., Baradia, D., Vhora, I., Patil, S. & Misra, A. Epidermal growth factor receptor targeting in cancer: A review of trends and strategies. Biomaterials 34, 8690-8707 (2013).
52. Kirkpatrick, P., Graham, J. & Muhsin, M. Cetuximab. Nat. Rev. Drug Discov. 3, 549-550 (2004).
53. Yamashiro, H., Toyama, K., Bando, H., Saji, S. & Toi, M. Trastuzumab treatment for breast cancer. The New England Journal of Medicine 354, 2186; author reply 2186 (2006).
54. Wilson, B. a & Collier, R. J. Diphtheria toxin and *Pseudomonas aeruginosa* exotoxin A: active-site structure and enzymic mechanism. Curr. Top. Microbiol. Immunol. 175, 27-41 (1992).
55. Subik, K. et al. The expression patterns of ER, PR, HER2, CK5/6, EGFR, KI-67 and AR by immunohistochemical analysis in breast cancer cell lines. Breast Cancer Basic Clin. Res. 4, 35-41 (2010).
56. Sellman, B. R., Nassi, S. & Collier, R. J. Point Mutations in Anthrax Protective Antigen that Block Translocation. J. Biol. Chem. 276, 8371-8376 (2001).
57. Weigelt, B., Lo, A. T., Park, C. C., Gray, J. W. & Bissell, M. J. HER2 signaling pathway activation and response of breast cancer cells to HER2-targeting agents is dependent strongly on the 3D microenvironment. Breast Cancer Res. Treat. 122, 35-43 (2010).
58. Serezani, C. H., Ballinger, M. N., Aronoff, D. M. & Peters-Golden, M. Cyclic AMP: Master regulator of innate immune cell function. American Journal of Respiratory Cell and Molecular Biology 39, 127-132 (2008).
59. Raker, V. K., Becker, C. & Steinbrink, K. The cAMP pathway as therapeutic target in autoimmune and inflammatory diseases. Frontiers in Immunology 7, (2016).
60. Vu, T. & Claret, F. X. Trastuzumab: Updated Mechanisms of Action and Resistance in Breast Cancer. Front. Oncol. 2, (2012).
61. Pohlmann, P. R., Mayer, I. A. & Mernaugh, R. Resistance to trastuzumab in breast cancer. Clinical Cancer Research 15, 7479-7491 (2009).
62. Ware, K. E. et al. A mechanism of resistance to gefitinib mediated by cellular reprogramming and the acquisition of an FGF2-FGFR1 autocrine growth loop. Oncogenesis 2, (2013).
63. Van Emburgh, B. O., Sartore-Bianchi, A., Di Nicolantonio, F., Siena, S. & Bardelli, A. Acquired resistance to EGFR-targeted therapies in colorectal cancer. Mol. Oncol. 8, 1084-94 (2014).
64. Brand, T. M., Iida, M. & Wheeler, D. L. Molecular mechanisms of resistance to the EGFR monoclonal antibody cetuximab. Cancer Biology and Therapy 11, 777-792 (2011).
65. Misale, S. et al. Emergence of KRAS mutations and acquired resistance to anti-EGFR therapy in colorectal cancer. Nature 486, 532-536 (2012).
66. Ritter, C. A. et al. Human breast cancer cells selected for resistance to trastuzumab in vivo overexpress epidermal growth factor receptor and ErbB ligands and remain dependent on the ErbB receptor network. Clin. Cancer Res. 13, 4909-4919 (2007).
67. Nahta, R., Yuan, L. X. H., Zhang, B., Kobayashi, R. & Esteva, F. J. Insulin-like growth factor-I receptor/human epidermal growth factor receptor 2 heterodimerization contributes to trastuzumab resistance of breast cancer cells. Cancer Res. 65, 11118-11128 (2005).
68. Corkery, B., Crown, J., Clynes, M. & O'Donovan, N. Epidermal growth factor receptor as a potential therapeutic target in triple-negative breast cancer. Ann. Oncol. 20, 862-867 (2009).
69. Mukohara, T. et al. Differential effects of gefitinib and cetuximab on non-small-cell lung cancers bearing epidermal growth factor receptor mutations. J. Natl. Cancer Inst. 97, 1185-1194 (2005).
70. Napolitano, S. et al. Primary and acquired resistance of colorectal cancer to anti-EGFR monoclonal antibody can be overcome by combined treatment of regorafenib with cetuximab. Clin. Cancer Res. 21, 2975-2983 (2015).
71. Press, M. F., Cordon-Cardo, C. & Slamon, D. J. Expression of the HER-2/neu proto-oncogene in normal human adult and fetal tissues. Oncogene 5, 953-62 (1990).
72. Yano, S. et al. Distribution and Function of EGFR in Human Tissue and the Effect of EGFR Tyrosine Kinase Inhibition. Anticancer Research 23, 3639-3650 (2003).
73. Mehner, C. et al. Tumor cell-produced matrix metalloproteinase 9 (MMP-9) drives malignant progression and metastasis of basal-like triple negative breast cancer. Oncotarget 5, 2736-2749 (2014).
74. Huang, S., New, L., Pan, Z., Han, J. & Nemerow, G. R. Urokinase plasminogen activator/urokinase-specific surface receptor expression and matrix invasion by breast cancer cells requires constitutive p38alpha mitogen-activated protein kinase activity. J Biol Chem 275, 12266-12272 (2000).
75. Abi-Habib, R. J. et al. A urokinase-activated recombinant anthrax toxin is selectively cytotoxic to many human tumor cell types. Mol. Cancer Ther. 5, 2556-2562 (2006).
76. Rabideau, A. E. & Pentelute, B. L. Delivery of Non-Native Cargo into Mammalian Cells Using Anthrax Lethal Toxin. ACS Chemical Biology 11, 1490-1501 (2016).
77. Pastan, I., Hassan, R., FitzGerald, D. J. & Kreitman, R. J. Immunotoxin therapy of cancer. Nature Reviews Cancer 6, 559-565 (2006).
78. Yamaizumi, M., Mekada, E., Uchida, T. & Okada, Y. One molecule of diphtheria toxin fragment a introduced into a cell can kill the cell. Cell 15, 245-250 (1978).
79. Nozaki, S. et al. Targeting urokinase-type plasminogen activator and its receptor for cancer therapy. Anti-Cancer Drugs 17, 1109-1117 (2006).
80. Stetler-Stevenson, W. G., Aznavoorian, S. & Liotta, L. A. Tumor Cell Interactions with the Extracellular Matrix During Invasion and Metastasis. Annu. Rev. Cell Biol. 9, 541-573 (1993).

81. Liu, S. et al. Anti-tumor activity of anthrax toxin variants that form a functional translocation pore by intermolecular complementation. Oncotarget 8, 65123-65131 (2017).
82. Liu, S. et al. Solid tumor therapy by selectively targeting stromal endothelial cells. Proc. Natl. Acad. Sci. 113, E4079-E4087 (2016).
83. Mazor, R. et al. Tolerogenic nanoparticles restore the antitumor activity of recombinant immunotoxins by mitigating immunogenicity. Proc. Natl. Acad. Sci. 201717063 (2018). doi:10.1073/pnas.1717063115
84. Kishimoto, T. K. et al. Improving the efficacy and safety of biologic drugs with tolerogenic nanoparticles. Nat. Nanotechnol. 11, 890-899 (2016).
85. Mijalis, A. J. et al. A fully automated flow-based approach for accelerated peptide synthesis. Nat. Chem. Biol. 13, 464-466 (2017).
86. Simon, M. D. et al. Rapid flow-based peptide synthesis. ChemBioChem 15, 713-720 (2014).

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A composition, comprising
   (a) a bacterial effector translocase protein having an N-terminus, a C-terminus and internal amino acids, wherein a first linker is conjugated to a first internal amino acid, wherein the first linker forms a first side chain;
   (b) an antibody wherein the antibody is linked to the bacterial effector translocase protein via the first side chain; and
   (c) a cargo molecule, wherein the bacterial effector translocase protein further comprises a second internal amino acid conjugated to a second linker to form a second side chain, and wherein the cargo molecule is linked to the bacterial effector translocase protein via the second side chain.

2. The composition of claim 1, wherein the antibody is linked to the bacterial effector translocase protein via the first side chain by chemical conjugation.

3. The composition of claim 2, wherein the chemical conjugation comprises sortase-mediated ligation.

4. The composition of claim 1, wherein the antibody is an immunoglobulin G (IgG) antibody.

5. The composition of claim 1, wherein the bacterial effector translocase protein is the anthrax lethal toxin translocase protective antigen (PA).

6. A method of treating cancer in a subject, the method comprising administering to the subject a pharmaceutically acceptable dose of a bacterial effector translocase protein having an N-terminus, a C-terminus and internal amino acids, wherein a first linker is conjugated to a first internal amino acid, wherein the first linker forms a first side chain; an antibody that binds an antigen on the cancer cells, wherein the antibody is linked to the bacterial effector translocase protein via the first side chain; and a cargo molecule, wherein the cargo molecule is a therapeutic anti-cancer molecule, and wherein the cargo molecule is delivered to the cancer cells of the subject to treat the cancer, wherein the bacterial effector translocase protein further comprises a second internal amino acid conjugated to a second linker to form a second side chain, and wherein the cargo molecule is linked to the bacterial effector translocase protein via the second side chain.

7. The method of claim 6, wherein the cargo molecule is selected from the group consisting of: a nucleic acid, a protein, a peptide, and a small molecule.

8. A method of chemically conjugating an antibody to a bacterial effector translocase protein, the method comprising:
   (a) synthesizing a bacterial effector translocase protein comprising an amino acid substitution from a wild-type amino acid to a cysteine residue;
   (b) crosslinking a D-peptide linker comprising an N-terminal tri-glycine to the cysteine residue;
   (c) ligating the bacterial effector translocase protein of (b) to an antibody,
   wherein the antibody comprises heavy chain C-terminal LPSTGG (SEQ ID NO: 59) tags, and wherein the ligation is performed by a sortase.

9. The method of claim 8, wherein the linker is cross-linked to the cysteine residue through a bromoacetamide.

* * * * *